US011655453B2

(12) United States Patent
Beatson et al.

(10) Patent No.: US 11,655,453 B2
(45) Date of Patent: May 23, 2023

(54) EXPANSION OF γδ T CELLS, COMPOSITIONS, AND METHODS OF USE THEREOF

(71) Applicants: King's College London, London (GB); GammaDelta Therapeutics Limited, London (GB)

(72) Inventors: Richard Beatson, London (GB); Adrian Hayday, Kent (GB); Oliver Nussbaumer, London (GB); Richard Woolf, London (GB); Maria Luisa Iannitto, London (GB); Natalie Mount, London (GB)

(73) Assignees: King's College London, London (GB); GammaDelta Therapeutics LTD, London (GB)

( * ) Notice: Subject to any disclaimer, the term of this patent is extended or adjusted under 35 U.S.C. 154(b) by 671 days.

(21) Appl. No.: 16/610,398

(22) PCT Filed: May 3, 2018

(86) PCT No.: PCT/EP2018/061413
§ 371 (c)(1),
(2) Date: Nov. 1, 2019

(87) PCT Pub. No.: WO2018/202808
PCT Pub. Date: Nov. 8, 2018

(65) Prior Publication Data
US 2021/0087528 A1    Mar. 25, 2021

(30) Foreign Application Priority Data

May 3, 2017  (GB) ..................... 1707048

(51) Int. Cl.
*C12N 5/0783* (2010.01)
*A61K 35/17* (2015.01)
*A61K 45/06* (2006.01)

(52) U.S. Cl.
CPC ............ *C12N 5/0636* (2013.01); *A61K 35/17* (2013.01); *A61K 45/06* (2013.01); *C12N 2500/90* (2013.01); *C12N 2501/21* (2013.01); *C12N 2501/2301* (2013.01); *C12N 2501/2302* (2013.01); *C12N 2501/2304* (2013.01); *C12N 2501/2309* (2013.01); *C12N 2501/2312* (2013.01); *C12N 2501/2315* (2013.01); *C12N 2501/2318* (2013.01); *C12N 2501/2321* (2013.01); *C12N 2501/2333* (2013.01)

(58) Field of Classification Search
None
See application file for complete search history.

(56) References Cited

U.S. PATENT DOCUMENTS

2016/0175358 A1* 6/2016 Jakobovits ............. A61K 35/17
                                                    435/372.3
2017/0107490 A1* 4/2017 Maeurer ................ A61K 38/21

FOREIGN PATENT DOCUMENTS

| CN | 106574244 A | 4/2017 |
|---|---|---|
| WO | WO-2012/156958 A2 | 11/2012 |
| WO | WO-2015/18957 A1 | 2/2015 |
| WO | WO-2015/189356 A1 | 12/2015 |
| WO | WO-2016/081518 A2 | 5/2016 |
| WO | WO-2016/166544 A1 | 10/2016 |
| WO | WO-2016164705 A1 | 10/2016 |
| WO | WO-2016/198480 A1 | 12/2016 |
| WO | WO-2017/015427 A1 | 1/2017 |
| WO | WO-2017/072367 A1 | 5/2017 |

OTHER PUBLICATIONS

Clark et al., J of Investigative Dermatology, 2006, vol. 126, pp. 1059-1070 (Year: 2006).*
International Search Report and Written Opinion for International Application No. GB1707048.3 dated Feb. 9, 2018 (6 pages).
Chennupati et al., "Intra- and intercompartmental movement of gammadelta T cells: intestinal intraepithelial and peripheral gammadelta T cells represent exclusive nonoverlapping populations with distinct migration characteristics," J Immunol. 185(9):5160-8 (2010) (11 pages).
Chew et al., "TIGIT Marks Exhausted T Cells, Correlates with Disease Progression, and Serves as a Target for Immune Restoration in HIV and SIV Infection," PLoS Pathog. 12(1):e1005349 (2016) (28 pages).
Chu et al., "Differential effects of IL-2 and IL-15 on the death and survival of activated TCR gamma delta+ intestinal intraepithelial lymphocytes," J Immunol. 162(4):1896-903 (1999) (9 pages).
Eberl et al., "Accumulation of a potent gammadelta T-cell stimulator after deletion of the lytB gene in *Escherichia coli*," Immunology. 106(2):200-11 (2002).
International Preliminary Report on Patentability for International Application No. PCT/EP2018/061413, dated Nov. 5, 2019 (13 pages).
International Search Report and Written Opinion for International Application No. PCT/EP2018/061413, dated Nov. 20, 2018 (23 pages).
Johnston et al., "The immunoreceptor TIGIT regulates antitumor and antiviral CD8(+) T cell effector function," Cancer Cell. 26(6):923-37 (2014).

(Continued)

*Primary Examiner* — Daniel C Gamett
(74) *Attorney, Agent, or Firm* — Sterne, Kessler, Goldstein & Fox P.L.L.C.

(57) ABSTRACT

The present invention provides methods of expanding γδ T cells from a non-haematopoietic tissue source. Further provided are compositions of expanded γδ T cells and methods of using the expanded γδ T cells (e.g., apart of an adoptive T cell therapy).

17 Claims, 52 Drawing Sheets

(56) References Cited

OTHER PUBLICATIONS

Von Lilienfeld-Toal et al., "Activated gammadelta T cells express the natural cytotoxicity receptor natural killer p 44 and show cytotoxic activity against myeloma cells," Clin Exp Immunol. 144(3):528-33 (2006).

Woolf et al., "Potential for innate-like responsiveness of resident T cells in human skin: a new perspective on tissue immune-surveillance," The Lancet. 387:108 (2016) (Abstract only) (1 page).

\* cited by examiner

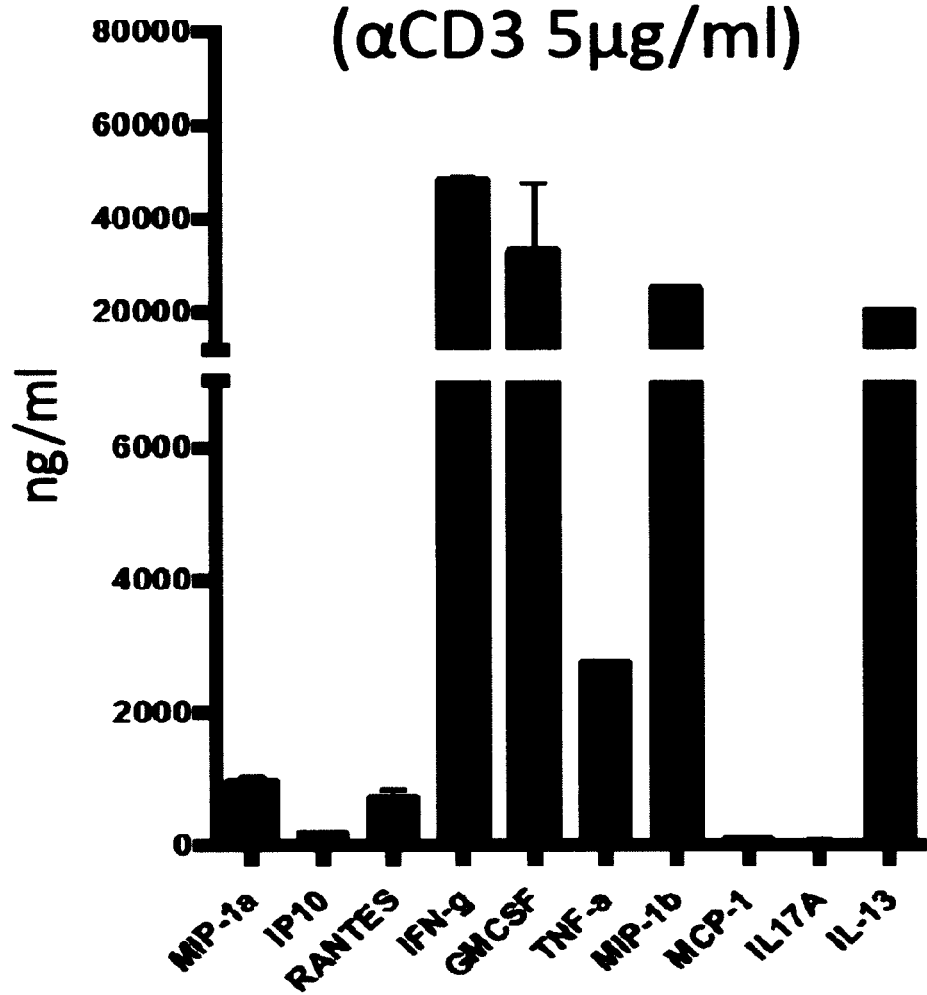

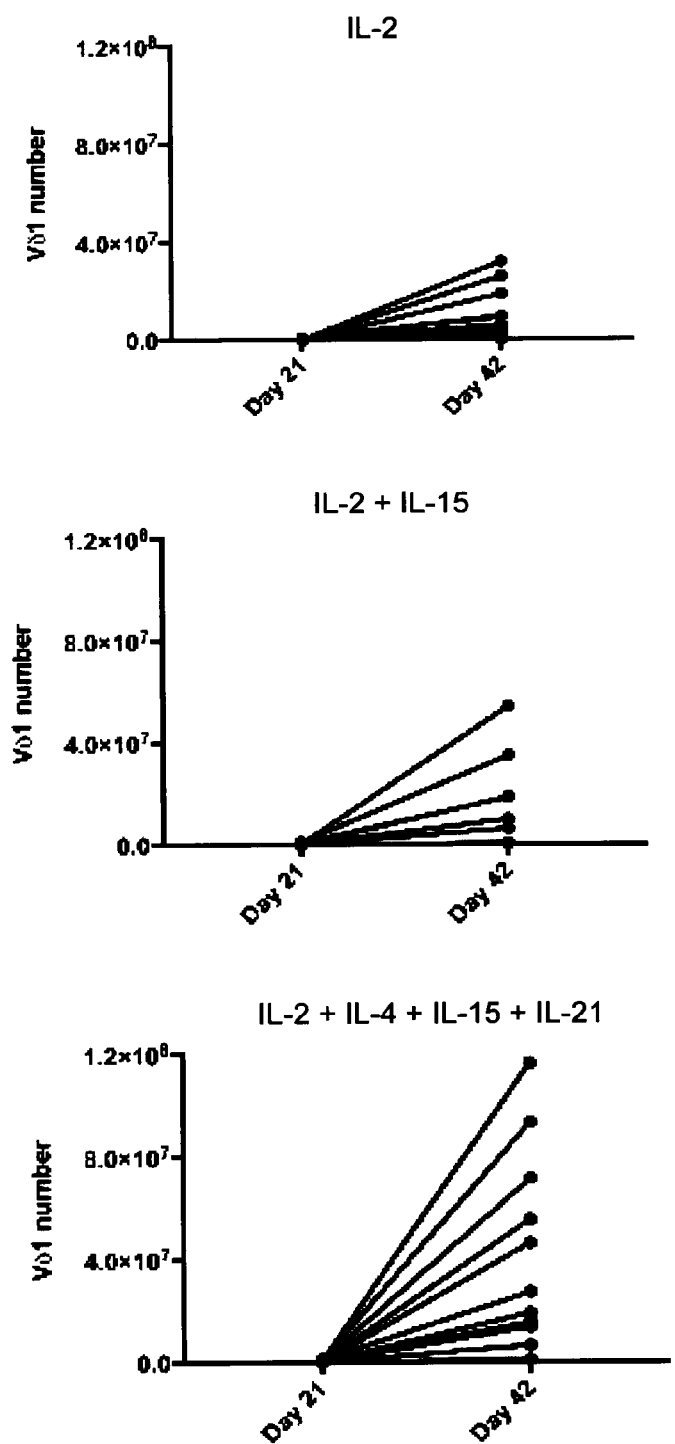

EXPANSION OF γδ T CELLS, COMPOSITIONS, AND METHODS OF USE THEREOF

BACKGROUND

The growing interest in T cell immunotherapy for cancer has focused on the evident capacity of subsets of $CD8^+$ and $CD4^+$ αβ T cells to recognize cancer cells and to mediate host-protective functional potentials, particularly when de-repressed by clinically mediated antagonism of inhibitory pathways exerted by PD-1, CTLA-4, and other receptors. Nonetheless, many questions remain. For example, there seem to be many major clinical scenarios in which the efficacy of such treatments seems poor. There are often profound adverse events, the capacity to predict either efficacy or adverse events is extremely limited, and there is very little explanation of the interactions that allow the host to sense tumor cells ("immunogenicity") that precede the activation of conventional, antigen-specific $CD8^+$ and $CD4^+$ αβ T cell responses.

Gamma delta T cells (γδ T cells) represent a subset of T cells that express on their surface a distinct, defining γδ T-cell receptor (TCR). This TCR is made up of one gamma (γ) and one delta (δ) chain. Human γδ T cells can be broadly classified as one or two types-peripheral blood-resident γδ T cells and non-haematopoietic tissue-resident γδ T cells. Most blood-resident γδ T cells express a Vδ2 TCR, whereas this is less common among tissue-resident γδ T cells, which more frequently use Vδ1 and/or other Vδ chains. Because non-haematopoietic tissue-resident γδ T cells are not easily obtainable in high numbers and no conventional isolation or expansion protocols exist, they have not been well characterized or studied for therapeutic applications. Therefore, there is an unmet need in the field for methods to isolate and expand non-haematopoietic tissue-resident γδ T cells to quantities sufficient to study and potentially adapt as therapies, e.g., as adoptive T cell therapies.

SUMMARY OF THE INVENTION

The present invention provides methods of expanding γδ T cells (e.g., skin-derived γδ T cells and/or non-Vδ2 T cells, e.g., Vδ1 T cells and/or DN T cells) from a non-haematopoietic tissue source (e.g., non-haematopoietic tissue-derived γδ T cells, e.g., non-haematopoietic tissue-derived Vδ1 T cells). Expansion methods include culturing the γδ T cells (e.g., γδ T cells separated from stromal cells of the non-haematopoietic tissue) in the absence of substantial TCR stimulation and/or in the presence of IL-4, IL-15, IL-21, and/or IL-2. Further provided are compositions of expanded γδ T cells (e.g., non-haematopoietic tissue-derived γδ T cells, e.g., non-haematopoietic tissue-derived Vδ1 T cells) and methods of using the expanded γδ T cells (e.g., a part of an adoptive T cell therapy, e.g., for treatment of cancer).

In one aspect, the invention features a method of expanding γδ T cells by (i) providing a population of γδ T cells obtained from a non-haematopoietic tissue; and (ii) culturing the γδ T cells in the presence of IL-2, IL-15, and a factor selected from the group consisting of IL-4, IL-21, IL-6, IL-7, IL-8, IL-9, IL-12, IL-18, IL-33, IGF-1, IL-1β, human platelet lysate (HPL), and stromal cell-derived factor-1 (SDF-1) for at least 5 days to produce an expanded population of γδ T cells. For example, the γδ T cells can be cultured in the presence of IL-2, IL-15, and IL-4; IL-2, IL-15, and IL-21; or IL-2, IL-15, IL-4, and IL-21.

In another aspect, the invention provides a method of expanding γδ T cells by (i) providing a population of γδ T cells obtained from a non-haematopoietic tissue; and (ii) culturing the γδ T cells in the presence of IL-2, IL-4, IL-15, and IL-21 for at least 5 days in an amount effective to produce an expanded population of γδ T cells.

In some embodiments of either of the previous aspects, the γδ T cells are simultaneously exposed to the IL-2, IL-4, IL-15, and IL-21 for at least 5 days. In some embodiments, step (ii) includes culturing the γδ T cells in the absence of exogenous TCR pathway agonists. In some embodiments, the method further includes, after step (i), separating the γδ T cells from non-haematopoietic cells to produce a separated population of γδ T cells, and step (ii) includes: (a) culturing the γδ T cells in the absence of substantial stromal cell contact; (b) culturing the γδ T cells in the absence of substantial tumor cell contact; and/or (c) culturing the γδ T cells in the absence of substantial feeder cell contact.

In another aspect, a method of expanding γδ T cells includes the steps of: (i) providing a non-haematopoietic tissue, the tissue comprising non-haematopoietic cells and γδ T cells; (ii) separating γδ T cells from non-haematopoietic cells to obtain a separated population of γδ T cells; and (iii) culturing the γδ T cells in the presence of IL-2, IL-15, and a factor selected from the group consisting of IL-4, IL-21, IL-6, IL-7, IL-8, IL-9, IL-12, IL-18, IL-33, IGF-1, IL-1β, HPL, and SDF-1 for at least 5 days to produce an expanded population of γδ T cells. In some embodiments, step (ii) includes culturing the γδ T cells in the presence of IL-2, IL-15, IL-4, and/or IL-21 (e.g., IL-2, IL-15, and IL-4; IL-2, IL-15, and IL-21; or IL-2, IL-15, IL-4, and IL-21). In some embodiments, the γδ T cells are simultaneously exposed to the IL-2, IL-15, IL-4, and/or IL-21. In some embodiments, step (iii) includes culturing the γδ T cells in the absence of substantial stromal cell contact with the γδ T cells. In some embodiments, step (iii) includes culturing the γδ T cells in the absence of exogenous TCR pathway agonists.

In another aspect, the invention features a method of expanding γδ T cells, the method including the steps of: (i) providing a population of γδ T cells obtained from a non-haematopoietic tissue; and (ii) culturing the γδ T cells in the presence of IL-2, IL-4, IL-15, and IL-21 for at least 5 days in an amount effective to produce an expanded population of γδ T cells. The γδ T cells can be simultaneously exposed to the IL-2, IL-4, IL-15, and IL-21, e.g., for at least 5 days, or they can be exposed to one or more of the factors prior to exposure to the others. In some embodiments, step (ii) includes culturing the γδ T cells in the presence of human recombinant IL-2, human recombinant IL-4, human recombinant IL-15, and human recombinant IL-21 for at least 5 days in an amount effective to produce an expanded population of γδ T cells. In some embodiments, step (ii) includes culturing the γδ T cells in the absence of exogenous TCR pathway agonists (e.g., anti-CD3), for example, in the absence of substantial TCR pathway activation. In some embodiments, step (ii) includes culturing the γδ T cells in the presence of IL-21 at a concentration from 1 ng/mL to 1,000 ng/mL (e.g., at about 10 ng/mL or about 100 ng/mL). Step (ii) may also include culturing the γδ T cells in the presence of one or more factors selected from the group consisting of IL-6, IL-7, IL-8, IL-9, IL-12, IL-18, IL-33, IGF-1, IL-1β, human platelet lysate (HPL), and stromal cell-derived factor-1 (SDF-1).

In another aspect, provided herein is a method of expanding γδ T cells by the steps of: (i) providing a population of γδ T cells obtained from a non-haematopoietic tissue; and (ii) culturing the γδ T cells in the presence of IL-2 and IL-15 for at least 5 days in an amount effective to produce an expanded population of γδ T cells. In some embodiments of this aspect, the γδ T cells are simultaneously exposed to the IL-2 and the IL-15. Step (ii) may include culturing the γδ T cells in the absence of exogenous TCR pathway agonists or in the absence of substantial TCR pathway activation. In some embodiments, step (ii) includes culturing the γδ T cells in the presence of one or more factors selected from the group consisting of IL-4, IL-21, IL-6, IL-7, IL-8, IL-9, IL-12, IL-18, IL-33, IGF-1, IL-1β, HPL, and SDF-1. In some embodiments, the γδ T cells are cultured in the presence of IL-4 and/or IL-21. In some embodiments, step (ii) includes culturing the γδ T cells in the presence of IL-2, IL-4, IL-15, and IL-21. The IL-21 can be at a concentration from 1 ng/mL to 1,000 ng/mL (e.g., 10 ng/mL or 100 ng/mL).

In yet another aspect, the invention features a method of expanding γδ T cells by the steps of: (i) providing a population of γδ T cells obtained from a non-haematopoietic tissue; and (ii) culturing the γδ T cells in the absence of substantial TCR pathway activation for at least 5 days to produce an expanded population of γδ T cells. In some embodiments, step (ii) includes culturing the γδ T cells in the presence of IL-2 and IL-15. In some instances, the γδ T cells are simultaneously exposed to the IL-4 and the IL-15. In some embodiments, step (ii) includes culturing the γδ T cells in the presence of one or more factors selected from the group consisting of IL-4, IL-21, IL-6, IL-7, IL-8, IL-9, IL-12, IL-18, IL-33, IGF-1, IL-1β, HPL, and SDF-1. For example, the γδ T cells can be cultured in the presence of IL-4, IL-21, or both. In some embodiments, the γδ T cells are cultured in the presence of IL-2, IL-4, IL-15, and IL-21. The IL-21 can be at a concentration from 1 ng/mL to 1,000 ng/mL (e.g., 10 ng/mL or 100 ng/mL).

In some embodiments of any of the preceding aspects, the method further includes, after step (i), separating the γδ T cells from non-haematopoietic cells to produce a separated population of γδ T cells, and step (ii) includes culturing the γδ T cells in the absence of substantial stromal cell contact, in the absence of substantial tumor cell contact, and/or in the absence of substantial feeder cell contact (e.g., irradiated feeder cells, B cells, or antigen-presenting cells).

In another aspect, featured herein is a method of expanding γδ T cells by the steps of: (i) providing a non-haematopoietic tissue, the tissue including non-haematopoietic cells and γδ T cells; (ii) separating γδ T cells from non-haematopoietic cells to obtain a separated population of γδ T cells; and (iii) culturing the γδ T cells in the absence of substantial stromal cell contact with the γδ T cells for at least 5 days to produce an expanded population of γδ T cells. In some embodiments, step (iii) includes culturing the γδ T cells in the absence of exogenous TCR pathway agonists and/or in the absence of substantial TCR pathway activation. In some embodiments, step (iii) includes culturing the γδ T cells in the presence of IL-2 and IL-15. For example, the γδ T cells can be simultaneously exposed to the IL-2 and the IL-15. In some embodiments, step (iii) includes culturing the γδ T cells in the presence of one or more factors selected from the group consisting of IL-4, IL-21, IL-6, IL-7, IL-8, IL-9, IL-12, IL-18, IL-33, IGF-1, IL-1β, HPL, and SDF-1. For example, in some instances, step (iii) includes culturing the γδ T cells in the presence of IL-4, IL-21, or both. In some embodiments, step (iii) includes culturing the γδ T cells in the presence of IL-2, IL-4, IL-15, and IL-21. The IL-21 can be at a concentration from 1 ng/mL to 1,000 ng/mL (e.g., 10 ng/mL or 100 ng/mL).

In another aspect, the invention provides a method of expanding γδ T cells by the steps of: (i) providing a non-haematopoietic tissue, the tissue including non-haematopoietic cells and γδ T cells; (ii) separating γδ T cells from non-haematopoietic cells to obtain a separated population of γδ T cells; and (iii) culturing the γδ T cells in the presence of IL-2 and IL-15 for at least 5 days to produce an expanded population of γδ T cells. In some embodiments, step (iii) includes culturing the γδ T cells in the absence of substantial stromal cell contact with the γδ T cells. In some embodiments, step (iii) includes culturing the γδ T cells in the absence of exogenous TCR pathway agonists or in the absence of substantial TCR pathway activation. In some embodiments, step (iii) includes culturing the γδ T cells in the presence of IL-2 and IL-15. The γδ T cells can be simultaneously exposed to the IL-2 and the IL-15. In some instances, step (iii) includes culturing the γδ T cells in the presence of one or more factors selected from the group consisting of IL-4, IL-21, IL-6, IL-7, IL-8, IL-9, IL-12, IL-18, IL-33, IGF-1, IL-1β, HPL, and SDF-1. For example, the γδ T cells can be cultured in the presence of IL-4 and/or IL-21. In some embodiments, step (iii) includes culturing the γδ T cells in the presence of IL-2, IL-4, IL-15, and IL-21. The IL-21 can be at a concentration from 1 ng/mL to 1,000 ng/mL (e.g., 10 ng/mL or 100 ng/mL).

In yet another aspect, featured herein is a method of expanding γδ T cells by the steps of: (i) providing a non-haematopoietic tissue, the tissue including non-haematopoietic cells and γδ T cells; (ii) separating γδ T cells from non-haematopoietic cells to obtain a separated population of γδ T cells; and (iii) culturing the γδ T cells in the absence of substantial TCR pathway activation for at least 5 days to produce an expanded population of γδ T cells. In some instances, step (iii) includes culturing the γδ T cells in the absence of exogenous TCR pathway agonists and/or in the absence of substantial stromal cell contact with the γδ T cells. In some embodiments, step (iii) includes culturing the γδ T cells in the presence of IL-2 and IL-15. For example, the γδ T cells can be simultaneously exposed to the IL-2 and the IL-15. In some embodiments, step (iii) includes culturing the γδ T cells in the presence of one or more factors selected from the group consisting of IL-4, IL-21, IL-6, IL-7, IL-8, IL-9, IL-12, IL-18, IL-33, IGF-1, IL-1β, HPL, and SDF-1. For example, the γδ T cells can be cultured in the presence of IL-2 and/or IL-21. In some embodiments, step (iii) includes culturing the γδ T cells in the presence of IL-2, IL-4, IL-15, and IL-21. The IL-21 can be at a concentration from 1 ng/mL to 1,000 ng/mL (e.g., 10 ng/mL or 100 ng/mL).

In some embodiments of any of the preceding methods, the step of separating the γδ T cells from non-haematopoietic cells includes culturing the γδ T cells and the non-haematopoietic cells on a scaffold configured to facilitate cell egress from the non-haematopoietic tissue. In some embodiments, the step of separating the γδ T cells from non-haematopoietic cells includes culturing the γδ T cells and the non-haematopoietic cells in the presence of IL-2, IL-15, or both. In some embodiments, a separated population of lymphocytes includes the separated population of γδ T cells, and the separated population of γδ T cells includes a separated population of Vδ1 T cells and/or double negative (DN cells). In some instances, prior to the expansion step, 1-10% of the separated population of lymphocytes are γδ T cells. In some embodiments, prior to the expansion step, 1-10% of the separated population of lymphocytes are Vδ1 T cells. Prior to the expansion step, at least 80% of the separated population of γδ T cells can be Vδ1 T cells, and/or less than 10% of the separated population of γδ T cells can be Vδ2 T cells. In some embodiments, αβ T cells and/or NK cells are removed from the separated population of γδ T cells (e.g., prior to the expansion step).

In some embodiments, prior to the expansion step, the separated population of γδ T cells includes at least 10% $CCR3^+$ cells, at least 10% $CCR4^+$ cells, at least 10% $CCR7^+$ cells, at least 10% $CCR8^+$ cells, or at least 10% $CD103^+$ cells. In some embodiments, prior to the expansion step, the separated population of γδ T cells includes a greater frequency of $CCR3^+$ cells, $CCR4^+$ cells, $CCR7^+$ cells, and/or $CCR8^+$ cells, relative to a reference population (e.g., a reference population of blood-resident Vδ2 T cells). In some embodiments, prior to the expansion step, the separated population of Vδ1 T cells includes a greater frequency of $NKG2D^+$ cells, $CD56^+$ cells, $CD69^+$ cells, and/or $TIM3^+$ cells relative to a reference population (e.g., a reference population of blood-resident Vδ2 T cells).

In some embodiments of any of the preceding aspects, within 14 days of culture during the expansion step, the expanded population of γδ T cells includes at least 20-fold the number of γδ T cells relative to the separated population of γδ T cells prior to the expansion step. Additionally or alternatively, within 21 days of culture during the expansion step, the expanded population of γδ T cells may include at least 50-fold the number of γδ T cells relative to the separated population of γδ T cells prior to expansion. The expanded population of γδ T cells includes an expanded population of Vδ1 T cells. In some embodiments, within 14 days of culture during the expansion step, the expanded population of Vδ1 T cells includes at least 20-fold the number of Vδ1 T cells relative to the separated population of Vδ1 T cells prior to expansion. Additionally or alternatively, within 21 days of culture during the expansion step, the expanded population of Vδ1 T cells includes at least 50-fold the number of Vδ1 T cells relative to the separated population of Vδ1 T cells prior to expansion.

In some embodiments of any of the preceding aspects, the expanded population of γδ T cells expresses CD27. For example, the expanded population of γδ T cells may have a greater median surface expression of CD27 than the separated population of γδ T cells. In some instances, the expanded population of γδ T cells has a median surface expression of CD27 that is at least two-fold relative to the separated population of γδ T cells. Additionally or alternatively, the expanded population of γδ T cells may have a greater frequency of $CD27^+$ cells relative to the separated population of γδ T cells. For example, the expanded population of γδ T cells may have at least a 5% greater frequency of $CD27^+$ cells relative to that of the separated population of γδ T cells. In some embodiments, the expanded population of Vδ1 T cells expresses CD27. In some embodiments, the expanded population of Vδ1 T cells has a greater median surface expression of CD27 than the separated population of Vδ1 T cells. For example, the expanded population of Vδ1 T cells may have a median surface expression of CD27 that is at least two-fold relative to that of the separated population of Vδ1 T cells. Additionally or alternatively, the expanded population of Vδ1 T cells may have a greater frequency of $CD27^+$ cells relative to the separated population of Vδ1 T cells. For example, the expanded population of Vδ1 T cells may have at least a 5% greater frequency of $CD27^+$ cells relative to that of the separated population of Vδ1 T cells.

In some embodiments of any of the preceding aspects, the expanded population of γδ T cells has a lower median surface expression of TIGIT than the separated population of γδ T cells. For example, the expanded population of γδ T cells may have a median surface expression of TIGIT that is at least 50% less than the separated population of γδ T cells. Additionally or alternatively, the expanded population of γδ T cells may have a lower frequency of $TIGIT^+$ cells than the separated population of γδ T cells. For example, the expanded population of γδ T cells may have at least a 20% lower frequency of $TIGIT^+$ cells than the separated population of γδ T cells. In some embodiments, the expanded population of Vδ1 T cells has a lower median surface expression of TIGIT than the separated population of Vδ1 T cells. For example, the expanded population of Vδ1 T cells may have a median surface expression of TIGIT that is at least 50% less than that of the separated population of Vδ1 T cells. Additionally or alternatively, the expanded population of Vδ1 T cells may have a lower frequency of $TIGIT^+$ cells than the separated population of Vδ1 T cells. For example, the expanded population of Vδ1 T cells may have at least a 20% lower frequency of $TIGIT^+$ cells than the separated population of Vδ1 T cells.

In some embodiments of any of the preceding aspects, the expanded population of γδ T cells has a greater surface expression of one or more of the markers selected from the group consisting of CD124, CD215, CD360, CTLA4, CD1b, BTLA, CD39, CD45RA, Fas Ligand, CD25, ICAM-1, CD31, KLRG1, CD30, and CD2, relative to a reference population (e.g., relative to the separated population of γδ T cells, e.g., relative to the separated population of γδ T cells prior to the expansion step). Additionally or alternatively, the expanded population of γδ T cells may have a greater frequency of cells expressing one or more of the markers selected from the group consisting of CD124, CD215, CD360, CTLA4, CD1b, BTLA, CD39, CD45RA, Fas Ligand, CD25, ICAM-1, CD31, KLRG1, CD30, and CD2, relative to a reference population (e.g., relative to the separated population of γδ T cells, e.g., relative to the separated population of γδ T cells prior to the expansion step). In some embodiments, the expanded population of γδ T cells has a lower surface expression of one or more of the markers selected from the group consisting of NKp44, NKp46, ICAM-2, CD70, CD28, CD103, NKp30, LAG3, CCR4, CD69, PD-1, and CD64, relative to a reference population (e.g., relative to the separated population of γδ T cells, e.g., relative to the separated population of γδ T cells prior to the expansion step). Additionally or alternatively, the expanded population of γδ T cells may have a lower frequency of cells expressing one or more of the markers selected from the group consisting of NKp44, NKp46, ICAM-2, CD70, CD28, CD103, NKp30, LAG3, CCR4, CD69, PD-1, and CD64, relative to a reference population (e.g., relative to the separated population of γδ T cells, e.g., relative to the separated population of γδ T cells prior to the expansion step).

In some embodiments, the expanded population of Vδ1 T cells has a greater surface expression of one or more of the markers selected from the group consisting of CD124, CD215, CD360, CTLA4, CD1b, BTLA, CD39, CD45RA, Fas Ligand, CD25, ICAM-1, CD31, KLRG1, CD30, and CD2, relative to a reference population (e.g., relative to the separated population of γδ T cells, e.g., relative to the separated population of γδ T cells prior to the expansion step). In some embodiments, the expanded population of γδ T cells has a greater frequency of cells expressing one or more of the markers selected from the group consisting of CD124, CD215, CD360, CTLA4, CD1b, BTLA, CD39, CD45RA, Fas Ligand, CD25, ICAM-1, CD31, KLRG1, CD30, and CD2, relative to a reference population (e.g., relative to the separated population of γδ T cells, e.g., relative to the separated population of γδ T cells prior to the expansion step). In some embodiments, the expanded population of γδ T cells has a lower surface expression of one or more of the markers selected from the group consisting of NKp44, NKp46, ICAM-2, CD70, CD28, CD103, NKp30, LAG3, CCR4, CD69, PD-1, and CD64, relative to a reference population (e.g., relative to the separated population of γδ T cells, e.g., relative to the separated population of γδ T cells prior to the expansion step). In other embodiments, the expanded population of γδ T cells has a lower frequency of cells expressing one or more of the markers selected from the group consisting of NKp44, NKp46, ICAM-2, CD70, CD28, CD103, NKp30, LAG3, CCR4, CD69, PD-1, and CD64, relative to a reference population (e.g., relative to the separated population of γδ T cells, e.g., relative to the separated population of γδ T cells prior to the expansion step).

In some embodiments of any of the preceding aspects, step (iii) includes culturing the γδ T cells in the absence of substantial stromal cell contact, in the absence of substantial feeder cell contact, and/or in the absence of substantial tumor cell contact. In some embodiments, the non-haematopoietic tissue is not a tumor tissue.

In some embodiments of any of the preceding aspects, the non-haematopoietic tissue is skin (e.g., human skin, e.g., skin obtained by punch biopsy). In other embodiments, the non-haematopoietic tissue is a gut tissue.

In any of the preceding aspects and embodiments, the method of expanding γδ T cells may be carried out in vitro.

In any of the preceding aspects and embodiments, the step of providing a non-haematopoietic tissue may include providing a non-haematopoietic tissue that has been obtained from a subject, e.g. a human or non-human animal subject.

In another aspect, the invention features an expanded γδ T cell obtained by the method of any one of the preceding aspects.

In another aspect, the invention provides a pharmaceutical composition including the expanded γδ T cell of the preceding aspect. In some embodiments, the pharmaceutical composition further includes an additional therapeutic agent selected from the group consisting of an immunotherapeutic agent, a cytotoxic agent, a growth inhibitory agent, a radiation therapy agent, an anti-angiogenic agent, or a combination of two or more agents thereof. In some instances, the additional therapeutic agent is an immunotherapeutic agent (e.g., IL-2, e.g., low dose IL-2, e.g., from $0.3 \times 10^6$ to $3.0 \times 10^6$ IU IL-2 per day, e.g., $1.0 \times 10^6$ IU IL-2 per day).

In another aspect, the invention features a pharmaceutical composition of the preceding aspect for use in a method of treating a subject by adoptive T cell therapy.

In another aspect, the invention features an expanded γδ T cell of any of the preceding aspects for use in a method of treating a subject by adoptive T cell therapy.

In yet another aspect, the invention provides a use of the expanded γδ T cell or the pharmaceutical composition thereof of any of the preceding aspects in the manufacture of a medicament for the treatment of cancer (e.g., a solid tumor), infection (e.g., cytomegalovirus (CMV) infection), or immunopathology in a subject.

In another aspect, the invention provides the expanded γδ T cell or the pharmaceutical composition thereof of any of the preceding aspects for use in a method for the treatment of cancer (e.g., a solid tumor), infection (e.g., cytomegalovirus (CMV) infection), or immunopathology in a subject.

In another aspect, the invention features a method of treating a subject by adoptive T cell therapy by administering a therapeutically effective amount of expanded γδ T cells obtained by the methods of any of the preceding embodiments to subject in need thereof. In some embodiments, the therapeutically effective amount of expanded γδ T cells is less than $10 \times 10^{12}$ cells per dose, or less than $10 \times 10^{12}$ cells over the course of treatment. In some embodiments, the method further includes administering one or more additional therapeutic agent to the subject in need thereof. The additional therapeutic agent may be selected from the group consisting of an immunotherapeutic agent, a cytotoxic agent, a growth inhibitory agent, a radiation therapy agent, an anti-angiogenic agent, or a combination of two or more agents thereof. The additional therapeutic agent may be administered concurrently with, prior to, or after administration of the expanded γδ T cells. In some embodiments, the additional therapeutic agent is an immunotherapeutic agent. In one embodiment, the immunotherapeutic agent is IL-2 (e.g., low dose IL-2, e.g., from $0.3 \times 10^6$ to $3.0 \times 10^6$ IU IL-2 per day, e.g., $1.0 \times 10^6$ IU IL-2 per day). These embodiments apply to any of the preceding, or following, aspects relating to the use of the expanded γδ T cells obtained by the methods disclosed herein (or a pharmaceutical composition including these γδ T cells) in a method treating a subject by adoptive T cell therapy.

In another aspect, the invention features a method of treating a subject by adoptive T cell therapy by administering a therapeutically effective amount of the pharmaceutical composition of any of the preceding aspects to a subject in need thereof.

In some embodiments of any of the preceding aspects, the subject is a human (e.g., a human cancer patient (e.g., a human cancer patient being treated for a solid tumor), or a human cancer patient being treated for an infection (e.g., an infection of a virus, such as CMV)).

In another aspect, the invention features a method of expanding γδ T cells including (i) providing a population of γδ T cells obtained from a non-haematopoietic tissue; and (ii) culturing the γδ T cells in the presence of: (a) IL-2 or IL-9; (b) IL-15; and (c) IL-21 for at least 5 days in an amount effective to produce an expanded population of γδ T cells. In some embodiments, the γδ T cells are cultured in the presence of IL-4 as well in step (ii)

In yet another aspect, the invention features a method of expanding γδ T cells by (i) providing a population of γδ T cells obtained from a non-haematopoietic tissue; and (ii) culturing the γδ T cells in the presence of IL-2, IL-15 and a factor selected from the group consisting of IL-21, stromal cell-derived factor (SDF, e.g., SDF-1), IL-1β, IL-12, IL-18, and IL-33 for at least 5 days to produce an expanded population of γδ T cells. In some embodiments, step (ii) includes culturing the γδ T cells in the absence of exogenous TCR pathway agonists. In some embodiments, step (ii) includes culturing the γδ T cells in serum-free medium. In some embodiments, after step (i), the γδ T cells are separated from non-haematopoietic cells to produce a separated population of γδ T cells. In addition, step (ii) may include culturing the γδ T cells in the absence of substantial stromal cell contact; culturing the γδ T cells in the absence of substantial tumor cell contact; and/or culturing the γδ T cells in the absence of substantial feeder cell contact.

In another aspect, the invention features a method of expanding γδ T cells through the steps of: (i) providing a non-haematopoietic tissue, the tissue including non-haematopoietic cells and γδ T cells; (ii) separating γδ T cells from non-haematopoietic cells to obtain a separated population of γδ T cells; and (iii) culturing the γδ T cells in the presence of IL-2, IL-15, and a factor selected from the group consisting of IL-21, SDF, IL-1β, IL-12, IL-18, and IL-33 for at least 5 days to produce an expanded population of γδ T cells. The γδ T cells can be cultured in the presence of IL-2, IL-15, and IL-21. Additionally or alternatively, the γδ T cells can be cultured in serum-free medium.

In yet another aspect, the invention features an isolated population of γδ T cells having a phenotype of any of the aforementioned expanded populations of γδ T cells. For example, in some embodiments, at least 50% of γδ T cells of the isolated population express CD27 and do not substantially express TIGIT. In some embodiments, at least 50% of γδ T cells of the isolated population express Vδ1.

In another aspect, the invention includes pharmaceutical compositions of the isolated γδ T cells of the preceding aspect.

In another aspect, provided herein are uses of the pharmaceutical compositions described herein.

In another aspect, the invention features a method of treating a subject by adoptive T cell therapy by administering a therapeutically effective amount of expanded γδ T cells described above, an isolated population described above, or a pharmaceutical composition described above, to a subject in need thereof.

Any embodiment disclosed in this application may be combined with any other disclosed embodiment, within each of the aspects of the invention.

BRIEF DESCRIPTION OF THE DRAWINGS

FIG. 1A: Skin resident lymphocytes were isolated using an organotypic cell culture published by Clark, et al (Clark, et al., *Journal of Investigational Dermatology.* 2006. 126(5):1059-70; "the Clark protocol"). Within CD45+ cells, anti-CD3 was used to stain for T cells and anti-CD56 antibody to identify NK cells, CD3-CD56+, respectively. Within CD3+ cells, antibodies against pan γδ T cell receptor were used to identify skin-resident γδ T cells, and anti-CD8α to identify proportions of conventional CD4 and CD8 positive αβ T cells within the CD3+, pan γδ TCR− gate. FIG. 1B shows a summary of these experiments for 7-10 donors using the Clark protocol. Using this protocol, lymphocytes within the human skin are still in contact with the dermal fibroblasts, and were supplemented with either no cytokines or with interleukin-2 (IL-2), interleukin-15 (IL-15), or IL-2 and IL-15, indicating that the use of cytokines does not change the skin-resident lymphocyte composition, with the exception of a slightly larger γδ T cell population when supplementing the culture with IL-15 or IL-2 and IL-15, validating the Clark protocol. Lymphocyte compositions after a 3 week organotypic skin culture are shown using the cytokines indicated as a summary for 4 donors. FIG. 1C: Skin-resident γδ cells include mostly Vδ1-expressing γδ T cells (76.24%±17.3), a small population of Vδ2 T cells (3.06%±6.1) and a population of pan-γδ TCR positive cells that stain negative for Vδ1 or Vδ2, also referred to herein as double negative (DN) γδ T cells (20.7%±13.97). Control staining of the blood of healthy volunteers shows the strong compartmentalization of human γδ T cells, as within the blood the dominant population of γδ T cells expressed the Vδ2 TCR chain. FIG. 1D: Skin-resident γδ T cells show markers previously associated with T cells that have been chronically activated, although these markers are signature indicators of tissue residency rather than necessarily reflecting chronic activation. Histograms show staining of the indicated markers on γδ T cells (filled histogram) versus the appropriate isotype control for each antibody (empty histogram).

FIG. 2A: Skin-resident γδ T cells show strong expression of the activatory and NK cell-associated receptor NKG2D (filled histogram, against isotype represented by the empty histogram). Upon activation using plate-bound recombinant MICA, one of the known ligands for the NKG2D receptors, skin γδ T cells respond without any other stimulation and independent of TCR ligation as the response is abrogated in the presence of blocking NKG2D antibodies. Cells were stimulated for 6 hours in the presence of brefeldin A and 100 units IL-2/mL and were subsequently analyzed for degranulation by staining for CD107a. The production of TNFα and INF-γ was analyzed by permeabilisation after surface staining and subsequent staining of intracellular cytokines. Phorbol 12-myristate 13-acetate (P) in combination with ionomycin (I) was used as a positive control for activating the T cells. FIG. 2B: Skin-resident γδ T cells show a TH1-biased response. γδ T cells were retrieved using the Clark protocol and stimulated with PMA and ionomycin for 6 h in the presence of brefeldin A and stained for intracellular cytokines. γδ T cells freshly isolated from human skin produce TNFα and IFN-γ upon stimulation, but only small or undetectable amounts of cytokines, e.g. IL-4, IL-17A, IL-13, IL-22, that are associated with Th2 or Th-17 cells, whereas conventional CD4+ αβ T cells show a much broader variety of cytokine production. FIG. 2C: Of lymphocytes derived directly from the human skin, varying levels of the NKG2D receptor are expressed by γδ T cells, CD8a+ conventional αβ T cells and NK cells. Among these cells, NK cells respond to exposure to NKG2D ligands alone, but within T cells it is only the γδ T cell population that shows a cytokine response upon stimulation with NKG2D ligands in the absence of any TCR stimulation (see upper row of flow cytometry dot plots). The response can be blocked using soluble blocking anti-NKG2D antibodies indicating that the response is exclusively mediated via the NKG2D receptor. FIG. 2D: Among skin-resident γδ T cells, only Vδ1 and DN γδ T cells show the innate-like potential to be activated by recombinant MICA alone (indicated by an *). Vδ2-expressing T cells found in small numbers within the skin show no such response.

FIG. 3A: Skin-resident lymphocytes were isolated using the Clark protocol. After a 3 week organotypic culture, skin lymphocytes were harvested and separated from any residual skin cells including fibroblasts and put into tissue culture wells at densities of 1 million lymphocytes/mL and supplemented with 100 U/mL of IL-2. After an additional 3 weeks, resident γδ T cells have strongly expanded and were enriched within the skin lymphocyte culture. This strong proliferative phenomenon was exclusive to skin-resident γδ T cells, represented by the majority of Vδ1 T cells which proliferated 127.18-fold on average within 3 weeks, whereas conventional αβ T cells only proliferated 5.21-fold on average; that is over 20-fold less well. FIG. 3B: Skin-resident Vδ1 T cells respond to loss of tissue by strongly up-regulating the marker Ki-67 (indicative of cell cycling) over 14 days (isotype control represented by the empty histogram bordered by a dashed line;

Ki-67 expression at day 0 represented by the empty histogram; Ki-67 expression at day 7 represented by the light grey histogram; Ki-67 expression at day 14 staining represented by the dark grey histogram). Furthermore, skin-resident Vδ1 T cells, which in the majority are negative for the IL-2 receptor alpha (CD25) when in contact with dermal stroma, up-regulate CD25 after segregation from the tissue (isotype control: dashed histogram, day 0 staining: light grey histogram, day 7 staining: dark grey histogram). FIG. 3C: High rates of cell cycling as indicated by median fluorescence intensity (MFI) of Ki-67 are only seen in skin-resident γδ T cells, represented by Vδ1 T cells, and are seen neither in conventional αβ T cells nor in NK cells where the MFI actually decreases over 14 days. FIG. 3D: Skin lymphocytes segregated from stromal cells show a strongly enriched resident γδ T cell population after a 3 week culture. This γδ T cell population contains a majority of Vδ1 positive cells (77.49%±17.04) and pan γδ TCR positive DN T cells (21.46%±16.92). The initial small Vδ2 T cell population seen in freshly harvested skin lymphocytes using the Clark protocol, is decreasing and almost lost (0.6%±1.204) after a 3 week expansion of tissue γδ T cells.

FIG. 4A: Mixed skin lymphocytes were harvested after organotypic culture as in the Clark protocol after 3 weeks. Mixed lymphocytes were then seeded on top of a confluent layer of autologous skin fibroblasts and in a transwell to control for the presence of soluble inhibitors produced by fibroblasts. After 14 days, fold-wise expansions calculated via absolute cell numbers present were measured for γδ T cells and conventional αβ T cells. Skin-resident γδ T cells showed a strong proliferative response when separated from tissue and in the presence of fibroblasts, but only when not in direct cellular contact with autologous fibroblasts. Conventional αβ T cells did not show such a response in any condition tested. FIG. 4B: Mixed lymphocytes obtained from organotypic culture were seeded onto a monolayer of autologous fibroblasts (light grey histograms) or seeded into empty wells (dark grey histograms) supplemented with IL-2 and cultured for 7 days. Skin-resident Vδ1 T cells (left panels) as well as pan γδ TCR+, DN T cells (right panels) remained quiescent in the direct presence of fibroblasts but showed strong activation when segregated from dermal organotypic culture and no presence of fibroblasts as indicated by up-regulated expression (MFI) of CD25, the Th-1 associated transcription factor T-bet, and the cell cycling marker Ki-67 (dashed, empty histograms represent the according isotype control).

FIG. 5A: Skin-resident γδ T cells were allowed to expand for 14 days after separation from the organotypic cell culture. γδ T cells were then negatively sorted using flow cytometry by excluding all conventional T cells stained with a pan αβ TCR monoclonal antibody. 150,000 sorted γδ T cells were then seeded into a 96 flat well culture plate in duplicate and left in culture with neither cytokine supplementation nor supplementation with any activating ligand for 24 hours. Supernatants were harvested and analyzed for cytokines produced using the Affymetrix LUMINEX®-based cytokine array. FIG. 5B: Negatively sorted γδ T cells were also seeded onto cancer cell lines seeded 1 day before at a concentration of 10,000 cells per well. As a control, negatively sorted conventional skin αβ T cells were used. T cells were seeded at effector: target ratios indicated in the presence and absence of blocking NKG2D antibody in the presence of IL-2 at 100 U/mL. Skin-resident γδ T cells showed superior killing, as shown by caspase cleaved epithelial specific cytokeratin 18 (CK18) release measured via ELISA, of malignant cell lines over conventional αβ T cells. The cytotoxicity was at least partially mediated via the NKG2D receptor, as shown by its reduction in cultures containing an antibody that blocks the NKG2D receptor.

FIG. 6A: An adaption of the Clark protocol allowed for the isolation of gut-resident lymphocytes. Mixed gut lymphocytes contain a large population of tissue-resident γδ T cells usually including mostly Vδ1 T cells, but also contain Vδ2 and double negative γδ T cells. FIG. 6B: γδ T cells isolated from gut organotypic culture show similar responses to skin-derived γδ T cells as they upregulate Ki-67 over time once they are segregated from gut stroma. FIG. 6C: Gut-derived γδ T cells respond to innate-like stimuli such as recombinant MICA by producing IFN-γ and by degranulation, as measured by CD107a up-regulation. FIG. 6D: γδ T cells isolated from gut organotypic culture show similar responses to skin-derived γδ T cells and expand over time in cell culture as seen by the overall enrichment in lymphocyte cultures that lack contact with the gut stroma.

FIG. 7A: Skin-derived γδ T cells stain positive for the skin homing chemokine receptors CCR4 and CCR8. FIG. 7B: The expression levels are different on expanded γδ T cells derived from the skin or blood, respectively.

FIG. 10A: Skin-derived Vδ1 T cells express high CD69, and TIM3, and low CD28. Furthermore they show high expression of the activation marker NKG2D. This phenotype is sustained by skin-derived Vδ1 T cells during expansion in vitro. By contrast, Vδ1 T cells derived from human blood lack these signs of activation, do not express CD69 or TIM3. Compared to skin-derived Vδ1 T cells, NKG2D expression on blood-derived Vδ1 T cells is much lower, whereas blood-derived Vδ1 T cells express the co-stimulatory molecule CD28. FIG. 10B: Only skin-derived Vδ1 T cells are reactive to NKG2D ligands such as recombinant MICA in the absence of any other stimulus, such as a ligand for the T cell receptor. Blood-derived Vδ1 or Vδ2 T cells did not show such responsiveness to innate-like stimuli. Cells were seeded into 96 well plates with recombinant MICA or anti-CD3 antibodies or both as indicated. Cells were cultured over 6 h in IL-2 100 U/mL and BFA for the last 4 hours followed by surface antigen staining, permeabilisation and intracellular staining for IFN-γ.

FIGS. 16A and 16B show the production of cytokines in skin derived Vδ1 T cells after TCR stimulation with PMA/Ionomycin (FIG. 16A) or anti-CD3 (FIG. 16B). Following isolation and expansion, skin derived Vδ1 T cells were purified using Fluorescence Activated Cell Sorting (FACS). 150.000 Vδ1 T cells were seeded into a 96 well flat bottom plate in duplicates for three donors and either stimulated with plate bound anti CD3 (5 μg/mL) or PMA/Ionomycin for 24 hours. Supernatants were analyzed for absolute amounts of indicated cytokines using the LUMINEX® platform.

FIGS. 17A-17H show results of expansion conditions. FIGS. 17A and 17B show representative flow cytometry plots and gating schemes for separated lymphocytes (after 21 days of separation culture; FIG. 17A) and lymphocytes that have been expanded in the presence of IL-2, IL-4, IL-15, and IL-21 for 20 days (FIG. 17B). FIG. 17C shows fold expansion of Vδ1 T cells under various conditions, normalized to Vδ1 T cell expansion as a result of IL-2 (100 U/mL) and IL-15 (10 ng/mL). FIG. 17D shows the fold expansion, relative to the separated population, as a result of treatment with IL-2+IL-15, IL2+IL-15+IL-4, IL-2+IL-15+L-21, and IL-2+L-15+L-4+L-21. FIG. 17E shows absolute Vδ1+ T cell numbers on day 21 (pre-expansion) and on day 42 (post expansion). Expansions were carried out in 100 U/ml IL-2, 100 U/ml IL-2+10 ng/ml IL-15, or 100 U/ml IL-2+5 ng/ml IL-4+10 ng/ml IL-15+100 ng/ml IL-21 as indicated. (n=8-17). FIG. 17F shows mean (plus SEM) Vδ1+ T cell numbers for each condition at both time points. ** p=0.001. Student's unpaired t-test. (n=8-17). FIG. 17G shows Vδ1+ T cell expansion using different concentrations of IL-21, normalized to expansion using 100 U/mL IL-2, 5 ng/ml IL-4 and 10 ng/ml IL-15 alone (n=3). FIG. 17H shows Vδ1+ T cell expansion using 100 U/ml IL-2+5 ng/ml IL-4+10 ng/ml IL-15+10 ng/ml IL-21, normalised to expansion with IL-2 alone.

FIG. 18A shows fold expression of CD27 (by MFI) under various conditions, normalized to CD27 expression as a result of IL-2 (100 U/mL) and IL-15 (10 ng/mL). FIG. 18B shows CD27 MFI, relative to the separated population, as a result of treatment with IL-2+IL-15, IL2+IL-15+IL-4, IL-2+IL-15+IL-21, and IL-2+IL-15+IL-4+IL-21. FIG. 18C shows Vδ1+ CD27 expression using different concentrations of IL-21, normalised to expansion using 100 U/mL IL-2, 5 ng/ml IL-4, and 10 ng/ml IL-15 alone, as assessed by flow cytometry (n=3). FIG. 18D shows Vδ1+ CD27 expression using 100 U/ml IL-2+5 ng/ml IL-4+10 ng/ml IL-15+10 ng/ml IL-21, normalised to expansion with IL-2 alone, as assessed by flow cytometry. (n=4).

FIG. 19 shows fold expression of TIGIT (by MFI) under various conditions, normalized to TIGIT expression resulting from IL-2 and IL-15 treatment.

FIG. 22A shows that initial isolated cultures contain relatively low numbers (<10%) of desired tissue-derived γδ T cells. In contrast FIGS. 22B-22D show that after expansion, the resulting cell population is heavily enriched for tissue-derived γδ T cells.

DETAILED DESCRIPTION

I. Introduction

Figure 1A:
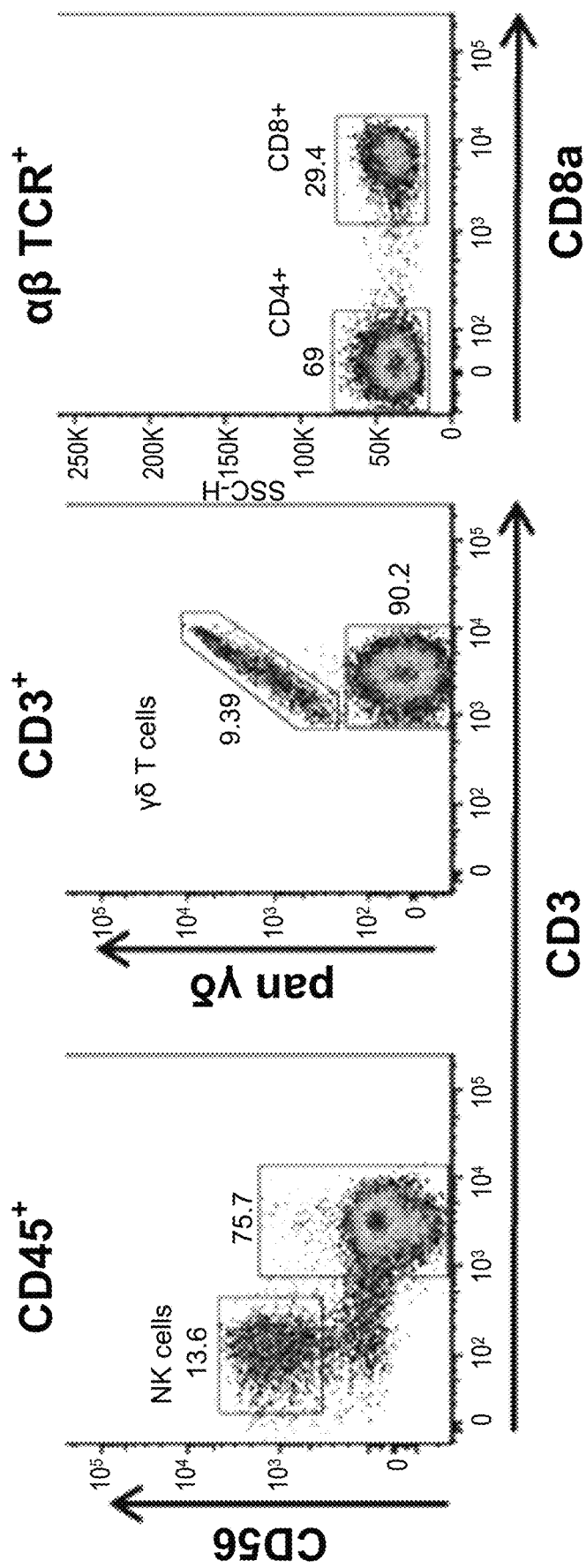
FIGS. 1A-1D show that the human skin includes a notable population of resident γδ T cells.
Figure 1B:
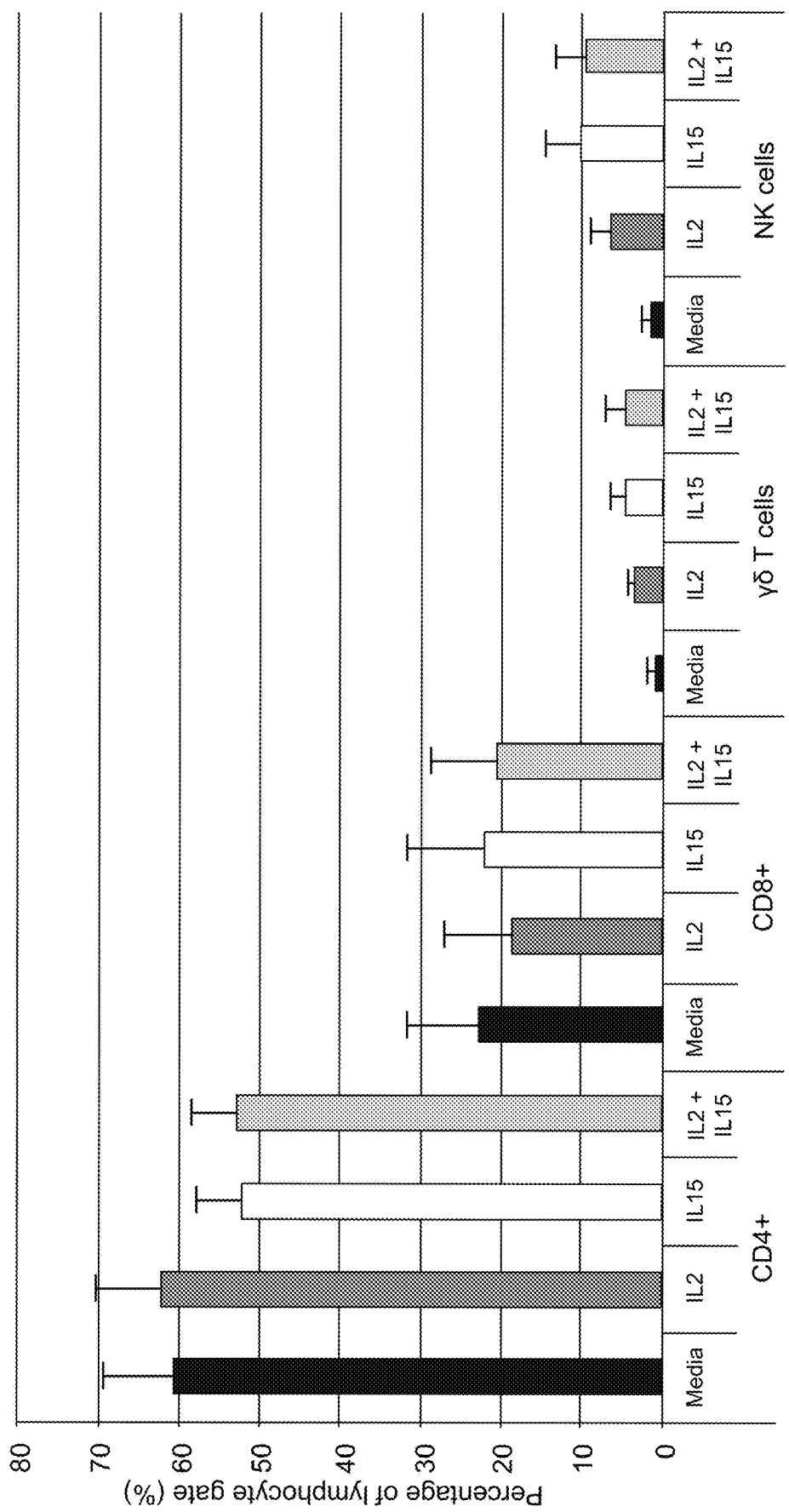

Provided herein are methods of expanding γδ T cells (e.g., skin-derived γδ T cells and/or non-Vδ2 T cells, e.g., Vδ1 T cells and/or double negative T cells) from a non-haematopoietic tissue source (e.g., non-haematopoietic tissue-derived γδ T cells, e.g., non-haematopoietic tissue-derived Vδ1 T cells). Expansion methods include culturing the γδ T cells (e.g., γδ T cells separated from stromal cells of the non-haematopoietic tissue) in the absence of substantial TCR stimulation and/or in the presence of interleukin-4 (IL-4), interleukin-15 (IL-15), interleukin-21 (IL-21), and/or interleukin-2 (IL-2). Further provided are compositions of expanded γδ T cells (e.g., skin-derived γδ T cells and/or non-Vδ2 T cells, e.g., Vδ1 T cells and/or DN T cells) and methods of using the expanded γδ T cells (e.g., a part of an adoptive T cell therapy, e.g., for treatment of cancer).

II. Definitions

It is to be understood that aspects and embodiments of the invention described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se. In some instances, "about" encompass variations of +20%, in some instances +10%, in some instances +5%, in some instances +1%, or in some instances +0.1% from the specified value, as such variations are appropriate to perform the disclosed methods.

As used herein, the terms "substantial" and "substantially" refer to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. When describing a physical scenario, such as receptor/ligand interaction or cell/cell contact, the scenario is substantial if its functional result is detectable by conventional means available to the person performing the method. For example, "substantial TCR activation" refers to a detectable level of TCR activation among a population of cells (e.g., a statistically significant degree of TCR activation). In some embodiments, a TCR is substantially activated upon exposure to up to 0.1%, up to 0.5%, up to 1%, up to 5%, up to 10%, up to 20%, up to 30%, or up to 40% of the $EC_{50}$ of the TCR pathway agonist (e.g., an antibody, e.g., anti-CD3, or a lectin) on the respective cell population. Likewise, "substantial cell contact" (e.g., substantial feeder cell contact, substantial stromal cell contact, or substantial tumor cell contact) refers to a degree of cell-to-cell contact able to induce a detectable change in the expanding cell (e.g., to reduce expansion). In some instances, substantial cell contact occurs when a contaminating cell type (e.g., a feeder cell, a stromal cell, or a tumor cell) is present in the culture compartment at a concentration of up to 0.1%, up to 0.5%, up to 1%, up to 5%, up to 10%, or up to 20% by number relative to the expanding cell population. A "substantial number" of cells or "substantial amount" of agent likewise refer to the number or amount required to induce a substantial effect, as defined above.

As used herein, "non-haematopoietic cells" include stromal cells and epithelial cells. Stromal cells are non-haematopoietic connective tissue cells of any organ and support the function of the parenchymal cells of that organ. Examples of stromal cells include fibroblasts, pericytes, mesenchymal cells, keratinocytes, endothelial cells, and non-hematological tumor cells. Epithelial cells are non-haematopoietic cells that line the cavities and surfaces of blood vessels and organs throughout the body. They are normally squamous, columnar, or cuboidal in shape and can be arranged as a single layer of cells, or as layers of two or more cells.

As used herein, "non-haematopoietic tissue-resident γδ T cells," "non-haematopoietic tissue-derived," and "non-haematopoietic tissue-native γδ T cells" refer to γδ T cells that were present in a non-haematopoietic tissue at the time the tissue is explanted. Non-haematopoietic tissue-resident γδ T cells may be obtained from any suitable human or non-human animal non-haematopoietic tissue. Non-haematopoietic tissue is a tissue other than blood or bone marrow. In some embodiments, the γδ T cells are not obtained from particular types of samples of biological fluids, such as blood or synovial fluid. Examples of such suitable human or non-human animal non-haematopoietic tissues include skin or a portion thereof (e.g., dermis or epidermis), the gastrointestinal tract (e.g. gastrointestinal epithelium, colon, small intestine, stomach, appendix, cecum, or rectum), mammary gland tissue, lung (preferably wherein the tissue is not obtained by bronchoalveolar lavage), prostate, liver, and pancreas. In some embodiments, non-haematopoietic tissue-resident γδ T cells can be derived from a lymphoid tissue, such as thymus, spleen, or tonsil. The γδ T cells may also be resident in human cancer tissues, e.g. breast and prostate. In some embodiments, the γδ T cells are not obtained from human cancer tissue. Non-haematopoietic tissue samples may be obtained by standard techniques e.g., by explant (e.g., biopsy). Non-haematopoietic tissue-resident γδ T cells include non-Vδ2 T cells, e.g., Vδ1 T cells, double negative (DN) T cells, Vδ3 T cells, and Vδ5 T cells.

As used herein, "IL-2" refers to native or recombinant IL-2 or a variant thereof that acts as an agonist for one or more IL-2 receptor (IL-2R) subunits (e.g., mutants, muteins, analogues, subunits, receptor complexes, fragments, isoforms, and peptidomimetics thereof). Such agents can support proliferation of an IL-2-dependent cell line, CTLL-2 (33; American Type Culture Collection (ATCC®) TIB 214). Mature human IL-2 occurs as a 133 amino acid sequence (less the signal peptide, consisting of an additional 20 N-terminal amino acids), as described in Fujita, et al. *Cell* 1986. 46.3:401-407. An IL-2 mutein is a polypeptide wherein specific substitutions to the interleukin-2 protein have been made while retaining the ability to bind IL-2R, such as those described in US 2014/0046026. The IL-2 muteins can be characterized by amino acid insertions, deletions, substitutions and modifications at one or more sites in or at the other residues of the native IL-2 polypeptide chain. In accordance with this disclosure any such insertions, deletions, substitutions and modifications result in an IL-2 mutein that retains the IL-2RP binding activity. Exemplary muteins can include substitutions of 1, 2, 3, 4, 5, 6, 7, 8, 9, 10 or more amino acids.

Nucleic acid encoding human IL-2 can be obtained by conventional procedures such as polymerase chain reaction (PCR). The amino acid sequence of human IL-2 (Gene ID 3558) is found in Genbank under accession locator NP_000577.2 GI: 28178861. The murine (*Mus musculus*) IL-2 amino acid sequence (Gene ID 16183) is found in Genbank under accession locator NP_032392.1 GI: 7110653.

IL-2 can also refer to IL-2 derived from a variety of mammalian species, including, for example, human, simian, bovine, porcine, equine, and murine. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring IL-2 variants are also encompassed by the invention. Examples of such variants are proteins that result from alternate mRNA splicing events or from proteolytic cleavage of the IL-2 protein, wherein the IL-2 binding property is retained. Alternate splicing of mRNA may yield a truncated but biologically active IL-2 protein. Variations attributable to proteolysis include, for example, differences in the N- or C-termini upon expression in different types of host cells, due to proteolytic removal of one or more terminal amino acids from the IL-2 protein (generally from 1-10 amino acids). In some embodiments, the terminus or interior of the protein can be modified to alter its physical properties, for example, with a chemical group such as polyethylene glycol (Yang, et al. *Cancer* 1995. 76: 687-694). In some embodiments, the terminus or interior of the protein can be modified with additional amino acids (Clark-Lewis, et al. *PNAS* 1993. 90:3574-3577).

As used herein, "IL-15" refers to native or recombinant IL-15 or a variant thereof that acts as an agonist for one or more IL-15 receptor (IL-15R) subunits (e.g., mutants, muteins, analogues, subunits, receptor complexes, fragments, isoforms, and peptidomimetics thereof). IL-15, like IL-2, is a known T-cell growth factor that can support proliferation of an IL-2-dependent cell line, CTLL-2. IL-15 was first reported by Grabstein, et al. (Grabstein, et al. *Science* 1994. 264.5161: 965-969) as a 114-amino acid mature protein. The term "IL-15," as used herein, means native or recombinant IL-15 and muteins, analogs, subunits thereof, or complexes thereof (e.g., receptor complexes, e.g., sushi peptides, as described in WO 2007/046006), and each of which can stimulate proliferation of CTLL-2 cells. In the CTLL-2 proliferation assays, supernatants of cells transfected with recombinantly expressed precursor and in-frame fusions of mature forms of IL-15 can induce CTLL-2 cell proliferation.

Human IL-15 can be obtained according to the procedures described by Grabstein, et al. (Grabstein, et al. *Science* 1994. 264.5161: 965-969) or by conventional procedures such as polymerase chain reaction (PCR). A deposit of human IL-15 cDNA was made with the ATCC® on Feb. 19, 1993 and assigned accession number 69245.

The amino acid sequence of human IL-15 (Gene ID 3600) is found in Genbank under accession locator NP000576.1 GI: 10835153 (isoform 1) and NP_751915.1 GI: 26787986 (isoform 2). The murine (*Mus musculus*) IL-15 amino acid sequence (Gene ID 16168) is found in Genbank under accession locator NP_001241676.1 GI: 363000984.

IL-15 can also refer to IL-15 derived from a variety of mammalian species, including, for example, human, simian, bovine, porcine, equine, and murine. An IL-15 "mutein" or "variant", as referred to herein, is a polypeptide substantially homologous to a sequence of a native mammalian IL-15 but that has an amino acid sequence different from a native mammalian IL-15 polypeptide because of an amino acid deletion, insertion or substitution. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring IL-15 variants are also encompassed by the invention. Examples of such variants are proteins that result from alternate mRNA splicing events or from proteolytic cleavage of the IL-15 protein, wherein the IL-15 binding property is retained. Alternate splicing of mRNA may yield a truncated but biologically active IL-15 protein. Variations attributable to proteolysis include, for example, differences in the N- or C-termini upon expression in different types of host cells, due to proteolytic removal of one or more terminal amino acids from the IL-15 protein (generally from 1-10 amino acids). In some embodiments, the terminus of the protein can be modified to alter its physical properties, for example, with a chemical group such as polyethylene glycol (Yang, et al. *Cancer* 1995. 76:687-694). In some embodiments, the terminus or interior of the protein can be modified with additional amino acids (Clark-Lewis, et al. *PNAS* 1993. 90:3574-3577).

As used herein, "IL-4" refers to native or recombinant IL-4 or a variant thereof that acts as an agonist for one or more IL-4 receptor (IL-4R) subunits (e.g., mutants, muteins, analogues, subunits, receptor complexes, fragments, isoforms, and peptidomimetics thereof). Such agents can support differentiation of naïve helper T cells (Th0 cells) to Th2 cells. Mature human IL-4 occurs as a 129 amino acid sequence (less the signal peptide, consisting of an additional 24 N-terminal amino acids). An IL-4 mutein is a polypeptide wherein specific substitutions to the interleukin-4 protein have been made while retaining the ability to bind IL-4Rα, such as those described in U.S. Pat. No. 6,313,272. The IL-4 muteins can be characterized by amino acid insertions, deletions, substitutions and modifications at one or more sites in or at the other residues of the native IL-4 polypeptide chain. In accordance with this disclosure any such insertions, deletions, substitutions and modifications result in an IL-4 mutein that retains the IL-2Rα binding activity. Exemplary muteins can include substitutions of 1, 2, 3, 4, 5, 6, 7, 8, 9, 10 or more amino acids.

Nucleic acid encoding human IL-4 can be obtained by conventional procedures such as polymerase chain reaction (PCR). The amino acid sequence of human IL-4 (Gene ID 3565) is found in Genbank under accession locator NG_023252. The murine (*Mus musculus*) IL-4 amino acid sequence (Gene ID 16189) is found in Genbank under accession locator NC_000077.6.

IL-4 can also refer to IL-4 derived from a variety of mammalian species, including, for example, human, simian, bovine, porcine, equine, and murine. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring IL-4 variants are also encompassed by the invention. Examples of such variants are proteins that result from alternate mRNA splicing events or from proteolytic cleavage of the IL-4 protein, wherein the IL-4 binding property is retained. Alternate splicing of mRNA may yield a truncated but biologically active IL-4 protein. Variations attributable to proteolysis include, for example, differences in the N- or C-termini upon expression in different types of host cells, due to proteolytic removal of one or more terminal amino acids from the IL-4 protein (generally from 1-10 amino acids). In some embodiments, the terminus of the protein can be modified to alter its physical properties, for example, with a chemical group such as polyethylene glycol (Yang, et al. *Cancer* 1995. 76:687-694). In some embodiments, the terminus or interior of the protein can be modified with additional amino acids (Clark-Lewis, et al. *PNAS* 1993. 90:3574-3577).

As used herein, "I-21" refers to native or recombinant IL-21 or a variant thereof that acts as an agonist for one or more IL-21 receptor (IL-21R) subunits (e.g., mutants, muteins, analogues, subunits, receptor complexes, fragments, isoforms, and peptidomimetics thereof). Such agents can support proliferation of natural killer (NK) and cytotoxic (CD8$^+$) T cells. Mature human IL-21 occurs as a 133 amino acid sequence (less the signal peptide, consisting of an additional 22 N-terminal amino acids). An IL-21 mutein is a polypeptide wherein specific substitutions to the interleukin-21 protein have been made while retaining the ability to bind IL-21Rα, such as those described in U.S. Pat. No. 9,388,241. The IL-21 muteins can be characterized by amino acid insertions, deletions, substitutions and modifications at one or more sites in or at the other residues of the native IL-21 polypeptide chain. In accordance with this disclosure any such insertions, deletions, substitutions and modifications result in an IL-21 mutein that retains the IL-21R binding activity. Exemplary muteins can include substitutions of 1, 2, 3, 4, 5, 6, 7, 8, 9, 10 or more amino acids.

Nucleic acid encoding human IL-21 can be obtained by conventional procedures such as polymerase chain reaction (PCR). The amino acid sequence of human IL-21 (Gene ID 59067) is found in Genbank under accession locator NC_000004.12. The murine (*Mus musculus*) IL-21 amino acid sequence (Gene ID 60505) is found in Genbank under accession locator NC_000069.6.

IL-21 can also refer to IL-21 derived from a variety of mammalian species, including, for example, human, simian, bovine, porcine, equine, and murine. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring IL-21 variants are also encompassed by the invention. Examples of such variants are proteins that result from alternate mRNA splicing events or from proteolytic cleavage of the IL-21 protein, wherein the IL-21 binding property is retained. Alternate splicing of mRNA may yield a truncated but biologically active IL-21 protein. Variations attributable to proteolysis include, for example, differences in the N- or C-termini upon expression in different types of host cells, due to proteolytic removal of one or more terminal amino acids from the IL-21 protein (generally from 1-10 amino acids). In some embodiments, the terminus of the protein can be modified to alter its physical properties, for example, with a chemical group such as polyethylene glycol (Yang, et al. *Cancer* 1995. 76:687-694). In some embodiments, the terminus or interior of the protein can be modified with additional amino acids (Clark-Lewis, et al. *PNAS* 1993. 90:3574-3577).

As used herein, "IL-9" refers to native or recombinant IL-9 or a variant thereof that acts as an agonist for one or more IL-9 receptor (IL-9R) subunits (e.g., mutants, muteins, analogues, subunits, receptor complexes, fragments, isoforms, and peptidomimetics thereof). Mature human IL-9 occurs as a 144 amino acid sequence. An IL-9 mutein is a polypeptide wherein specific substitutions to the interleukin-9 protein have been made while retaining the ability to bind IL-9R. IL-9 muteins can be characterized by amino acid insertions, deletions, substitutions and modifications at one or more sites in or at the other residues of the native IL-9 polypeptide chain. In accordance with this disclosure any such insertions, deletions, substitutions and modifications result in an IL-9 mutein that retains the IL-9R binding activity. Exemplary muteins can include substitutions of 1, 2, 3, 4, 5, 6, 7, 8, 9, 10 or more amino acids.

Nucleic acid encoding human IL-9 can be obtained by conventional procedures such as polymerase chain reaction (PCR). The amino acid sequence of human IL-9 is given by UniProtKB P15248.

IL-9 can also refer to IL-9 derived from a variety of mammalian species, including, for example, human, simian, bovine, porcine, equine, and murine. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring IL-9 variants are also encompassed by the invention. Examples of such variants are proteins that result from alternate mRNA splicing events or from proteolytic cleavage of the IL-9 protein, wherein the IL-9 binding property is retained. Alternate splicing of mRNA may yield a truncated but biologically active IL-9 protein. Variations attributable to proteolysis include, for example, differences in the N- or C-termini upon expression in different types of host cells, due to proteolytic removal of one or more terminal amino acids from the IL-9 protein (generally from 1-10 amino acids). In some embodiments, the terminus of the protein can be modified to alter its physical properties, for example, with a chemical group such as polyethylene glycol (Yang, et al. *Cancer* 1995. 76:687-694). In some embodiments, the terminus or interior of the protein can be modified with additional amino acids (Clark-Lewis, et al. *PNAS* 1993. 90:3574-3577).

Any one or more of the above factors may be included in an expansion protocol in an amount effective to produce an expanded population of γδ T cells. As used herein, the phrase "in an amount effective to" refers to an amount that induces a detectable result (e.g., a number of cells having a statistically significant increased number relative to its starting population, e.g., at a p<0.05). In instances in which multiple factors are present at once, an effective amount refers to the composite effect of all factors (e.g., the composite effect of IL-2 and IL-15, or the composite effect of IL-2 or IL-9, IL-4, IL-15, and IL-21).

"T cell receptor (TCR) pathway agonists" or "agents that activate the TCR pathway" refer to compounds that induce proliferation or other consequences of activation of T cells, such as αβ T cells and/or blood-resident γδ T cells, through TCR signaling. T cell signaling modulators function by sequential activation of the Src-related protein tyrosine kinases (PTKs), Lck and Fyn, and zeta-chain (TCR) associated protein kinase of 70 kDa (ZAP70). These PTKs lead to phosphorylation of polypeptides including linker activator for T cells (LAT), which leads to downstream stimulation through extracellular signal regulated kinase (ERK), c-Jun N-terminal kinase (JNK), and nuclear factor of activated T-cells (NFAT). Co-stimulation, for example through CD28 and CD45, can enhance phosphorylation and enhance TCR signaling pathways. Thus, any agent that targets a part of the TCR or co-stimulatory pathway can activate T cell signaling. TCR pathway agonists include antibodies (e.g., monoclonal antibodies, e.g., anti-TCR Vδ1, anti-TCR δTCS-1, anti-TCR PAN γδ, and anti-CD3), lectins (e.g., plant lectins, e.g., Concanavalin A, lectins from *Phaseolus vulgaris* (PHA-P), *Phytolacca Americana, Triticum vulgaris, Lens culinaris, Glycine max, Maackia amurensis, Pisum sativum*, and *Sambucus nigra*), synthetic phosphoantigens (e.g., BrHPP (bromohydrin pyrophosphate), 2M3B1PP (2-methyl-3-butenyl-1-pyrophosphate), HMBPP ((E)-4-Hydroxy-3-methyl-but-2-enyl pyrophosphate), or IPP (isopentenyl pyrophosphate)), and N-bisphosphonates (e.g., zoledronate). TCR pathway agonists include co-receptor agonists, including antibodies (e.g., monoclonal antibodies, e.g., anti CD2, anti-CD6, anti-CD9, anti-CD28, anti-CD43, anti-CD94, anti-CD160, anti-SLAM, anti-NKGD2, anti-2B4, anti-HLA-A, anti-HLA-b, anti-HLA-C, and anti-ICAM-3) and proteins (e.g., recombinant proteins, e.g., recombinant human proteins, e.g., CD7L, CD26, CD27L, CD30L, CD40L, OX40L, 4-1BBL, ICAM-1, fibronectin, hydrocortisone, and variants thereof, e.g., Fc-fusion proteins, e.g., CD27L-Fc). TCR pathway agonists may be soluble or membrane bound and may, for example, be presented on cells, such as artificial antigen presenting cells (aAPCs), as is the case for MHC or HLA complexes. Suitable aAPCs for activating T cell signaling are known in the art. Suitable methods of activating T cells by exogenously adding TCR pathway agonists are well known in the art and summarized in FIG. 1 of Deniger, et al. (Deniger, et al. *Frontiers in Immunology*. 2014. 5(636):1-10).

"Exogenous TCR pathway agonists" refer to TCR pathway agonists that do not originate from the non-haematopoietic tissue or donor thereof (i.e., they are exogenously added). Thus, it will be understood that in some embodiments of the invention, a TCR pathway agonist may be present in the culture as residual material from the non-haematopoietic tissue (e.g., soluble fibronectin or cell-bound ICAM-1). In some embodiments, a residual TCR pathway agonist is of a negligible concentration and does not substantially activate the T cells.

As used herein, a "synthetic scaffold," "scaffold," and "grid" are used interchangeably and refer to a non-native three-dimensional structure suitable to support cell growth. An explant may be adhered to a synthetic scaffold to facilitate lymphocyte egress from the explant onto the scaffold. Synthetic scaffolds may be constructed from natural and/or synthetic materials such as polymers (e.g., natural or synthetic polymers, e.g., poly vinyl pyrolidones, polymethylmethacrylate, methyl cellulose, polystyrene, polypropylene, polyurethane), ceramics (e.g., tricalcium phosphate, calcium aluminate, calcium hydroxyapatite), or metals (tantalum, titanium, platinum and metals in the same element group as platinum, niobium, hafnium, tungsten, and combinations of alloys thereof). Biological factors (e.g., collagens (e.g., collagen I or collagen II), fibronectins, laminins, integrins, angiogenic factors, anti-inflammatory factors, glycosaminoglycans, vitrogens, antibodies and fragments thereof, cytokines (e.g., IL-2 or IL-15, and combinations thereof) may be coated onto the scaffold surface or encapsulated within the scaffold material to enhance cell adhesion, migration, survival, or proliferation, according to methods known in the art. This and other methods can be used to isolate lymphocytes from a number of other non-haematopoietic tissue types, e.g. gut, prostate and breast. An exemplary synthetic scaffold contemplated for use as part of the present invention include that used in the Clark protocol.

As used herein, the terms "separation," "separated," or to "separate" refer to the act of breaking or prohibiting physical contact between distinct cell populations (e.g., separation of haematopoietic cells (e.g., lymphocytes) from non-haematopoietic cells). Separation may be performed, e.g., by forcefully pipetting a mixed population of cells to break inter-membrane associations, or by inducing "crawl-out" of a population of cells from, e.g., a tissue matrix, by culturing with, e.g., chemokines or cytokines, as described by Carrasco, et al. (Carrasco A. et al *Journal of Immunological Methods* 2013. 389(1-2):29-37). Separation may be maintained during culture using a transwell culture system or by similar culture methods that prevent physical contact between distinct cell populations.

As used herein, a "separated population of γδ cells" refers to a population of haematopoietic cells including γδ cells that has been separated from its non-haematopoietic tissue of origin such that it is out of substantial contact with non-haematopoietic cells (e.g., according to any of the separation protocols described herein). Likewise, a "separated population of Vδ1 T cells" refers to a population of haematopoietic cells including Vδ1 T cells that has been separated from its non-haematopoietic tissue of origin such that it is out of substantial contact with non-haematopoietic cells (e.g., according to any of the separation protocols described herein). Thus, in these instances, the separation refers to the separation of haematopoietic cells (e.g., lymphocytes) from non-haematopoietic cells (e.g., stromal cells and/or epithelial cells).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, an "expansion step" refers to a phase of culture that occurs after separation, in which the number of a particular γδ T cell increases by cell division. It will be understood that cell division may occur during the separation phase, while the γδ T cells are in contact with stromal cells, but the expansion step does not start until separation is complete. Thus, when a separated cell population is characterized at a point "prior to the expansion step," it is meant the point in time after the separation culture and before the expansion culture.

As used herein, an "expanded population of γδ cells" refers to a population of haematopoietic cells including γδ T cells that has been cultured in a condition and for a duration that has induced the expansion of γδ cells, i.e., increased γδ cell number. Likewise, an "expanded population of Vδ1 T cells," as used herein, refers to a population of haematopoietic cells including Vδ1 T cells that has been cultured in a condition and for a duration that has induced the expansion of Vδ1 T cells, i.e., increased Vδ1 cell number.

As used herein, a "feeder cell" refers to any exogenous cell added to a culture to provide cell-to-cell surface contact to the non-haematopoietic tissue-derived cells. Feeder cells can be primary cells (e.g., derived from a tissue) or a derived from a cell line. Feeder cells can be live or irradiated, and include tumor cells, fibroblasts, B cells, and other antigen presenting cells.

The term "marker" herein to refers to a DNA, RNA, protein, carbohydrate, glycolipid, or cell-based molecular marker, the expression or presence of which in a patient's sample can be detected by standard methods (or methods disclosed herein).

A cell or population of cells that "expresses" a marker of interest is one in which mRNA encoding the protein, or the protein itself, including fragments thereof, is determined to be present in the cell or the population. Expression of a marker can be detected by various means. For example, in some embodiments, expression of a marker refers to a surface density of the marker on a cell. Mean fluorescence intensity (MFI), for example, as used as a readout of flow cytometry, is representative of the density of a marker on a population of cells. A person of skill in the art will understand that MFI values are dependent on staining parameters (e.g., concentration, duration, and temperature) and fluorochrome composition. However, MFI can be quantitative when considered in the context of appropriate controls.

For instance, a population of cells can be said to express a marker if the MFI of an antibody to that marker is significantly higher than the MFI of an appropriate isotype control antibody on the same population of cells, stained under equivalent conditions. Additionally or alternatively, a population of cells can be said to express a marker on a cell-by-cell basis using a positive and negative gate according to conventional flow cytometry analytical methods (e.g., by setting the gate according to isotype or "fluorescence-minus-one" (FMO) controls). By this metric, a population can be said to "express" a marker if the number of cells detected positive for the marker is significantly higher than background (e.g., by gating on an isotype control).

As used herein, when a population's expression is stated as a percentage of positive cells and that percentage is compared to a corresponding percentage of positive cells of a reference population, the percentage difference is a percentage of the parent population of each respective population. For example, if a marker is expressed on 10% of the cells of population A, and the same marker is expressed on 1% of the cells of population B, then population A is said to have a 9% greater frequency of marker-positive cells than population B (i.e., 10%-1%, not 10%÷1%). When a frequency is multiplied through by the number of cells in the parent population, the difference in absolute number of cells is calculated. In the example given above, if there are 100 cells in population A, and 10 cells in population B, then population A has 100-fold the number of cells relative to population B, i.e., (10%×100)÷(1%×10).

An expression level of a marker may be a nucleic acid expression level (e.g., a DNA expression level or an RNA expression level, e.g., an mRNA expression level). Any suitable method of determining a nucleic acid expression level may be used. In some embodiments, the nucleic acid expression level is determined using qPCR, rtPCR, RNA-seq, multiplex qPCR or RT-qPCR, microarray analysis, serial analysis of gene expression (SAGE), MassARRAY technique, in situ hybridization (e.g., FISH), or combinations thereof.

As used herein, a "reference population" of cells refers to a population of cells corresponding to the cells of interest, against which a phenotype of the cells of interest are measured. For example, a level of expression of a marker on a separated population of non-haematopoietic tissue-derived γδ cells may be compared to the level of expression of the same marker on a haematopoietic tissue-derived γδ T cell (e.g., a blood-resident γδ cell, e.g., a blood-resident γδ cell derived from the same donor or a different donor) or a non-haematopoietic tissue-derived γδ T cell expanded under different conditions (e.g., in the presence of substantial TCR activation, in the presence of an exogenous TCR activation agent (e.g., anti-CD3), or in substantial contact with stromal cells (e.g., fibroblasts)). A population may also be compared to itself at an earlier state. For example, a reference population can be a separated cell population prior to its expansion. In this case, the expanded population is compared to its own composition prior to the expansion step, i.e., its past composition, in this case, is the reference population.

"Cancer" refers to the abnormal proliferation of malignant cancer cells and includes leukemias, such as acute myeloid leukemia (AML), chronic myeloid leukemia (CML), acute lymphoblastic leukemia (ALL) and chronic lymphocytic leukemia (CLL), lymphomas, such as Hodgkin lymphoma, non-Hodgkin lymphoma and multiple myeloma, and solid cancers such as sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, esophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer.

Cancer cells within cancer patient may be immunologically distinct from normal somatic cells in the individual (e.g., the cancerous tumor may be immunogenic). For example, the cancer cells may be capable of eliciting a systemic immune response in the cancer patient against one or more antigens expressed by the cancer cells. The antigens that elicit the immune response may be tumor antigens or may be shared by normal cells. A patient with cancer may display at least one identifiable sign, symptom, or laboratory finding that is sufficient to make a diagnosis of cancer in accordance with clinical standards known in the art. Examples of such clinical standards can be found in textbooks of medicine such as Harrison's Principles of Internal Medicine (Longo D L, Fauci A S, Kasper D L, Hauser S L, Jameson J, Loscalzo J. eds. 18e. New York, N.Y.: McGraw-Hill; 2012). In some instances, a diagnosis of a cancer in an individual may include identification of a particular cell type (e.g. a cancer cell) in a sample of a body fluid or tissue obtained from the individual.

As used herein, a "solid tumor" is any cancer of body tissue other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

A patient, subject, or individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. a marmoset or baboon), an ape (e.g. a gorilla, chimpanzee, orangutan or gibbon), or a human.

In some embodiments, the patient, subject, or individual is a human. In other preferred embodiments, non-human mammals, especially mammals that are conventionally used as models for demonstrating therapeutic efficacy in humans (e.g. murine, primate, porcine, canine, or rabbit) may be employed.

As used herein, "treatment" (and grammatical variations thereof such as "treat" or "treating") refers to clinical intervention, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment as a prophylactic measure (i.e. prophylaxis) is also included. For example, a patient, subject, or individual susceptible to or at risk of the occurrence or re-occurrence of cancer may be treated as described herein. Such treatment may prevent or delay the occurrence or re-occurrence of cancer in the patient, subject, or individual.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens. Reducing immune suppression in cancerous tumors in an individual may improve the capacity of the individual to resist cancer growth, in particular growth of a cancer already present the subject and/or decrease the propensity for cancer growth in the individual.

In some embodiments, expanded γδ T cells (e.g., non-haematopoietic tissue-derived γδ T cells, e.g., non-haematopoietic tissue-derived Vδ1 T cells) are administered to delay development of a disease or to slow the progression of a disease or disorder.

As used herein, "administering" is meant a method of giving a dosage of a therapy (e.g., an adoptive T cell therapy comprising, e.g., non-haematopoietic tissue-derived γδ T cells) or a composition (e.g., a pharmaceutical composition, e.g., a pharmaceutical composition including non-haematopoietic tissue-derived γδ T cells) to a patient. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, intravitreally (e.g., by intravitreal injection), by eye drop, orally, topically, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the therapeutic agent or composition being administered and the severity of the condition, disease, or disorder being treated).

A "therapeutically effective amount" refers to an amount of a therapeutic agent to treat or prevent a disease or disorder in a mammal. In the case of cancers, the therapeutically effective amount of the therapeutic agent (e.g., a non-haematopoietic tissue-derived γδ T) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), response rates (e.g., complete response (CR) and partial response (PR)), duration of response, and/or quality of life.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s). For example, in some embodiments, a non-haematopoietic tissue-derived γδ T cell and IL-2 may be administered concurrently.

The term "pharmaceutical composition" refers to a preparation which is in such form as to permit the biological activity of one or more active ingredients contained therein to be effective, and which contains no additional components which are unacceptably toxic to a patient to which the formulation would be administered.

III. Methods of Separating and Expanding γδ T Cells

The invention provides methods for isolating and expanding γδ T cells (e.g., skin-derived γδ T cells and/or non-Vδ2 T cells, e.g., Vδ1 T cells and/or DN T cells) from any human or non-human animal non-haematopoietic tissue that can be or has been removed from a patient. In some embodiments, the non-haematopoietic tissue from which the γδ T cells are derived and expanded is skin (e.g., human skin), which can be obtained by methods known in the art. In some embodiments, the skin is obtained by punch biopsy. Alternatively, the methods of isolation and expansion of γδ T cells provided herein can be applied to the gastrointestinal tract (e.g., colon), mammary gland, lung, prostate, liver, spleen, and pancreas. The γδ T cells may also be resident in human cancer tissues, e.g., tumors of the breast or prostate. In some embodiments, the γδ T cells may be from human cancer tissues (e.g., solid tumor tissues). In other embodiments, the γδ T cells may be from non-haematopoietic tissue other than human cancer tissue (e.g., a tissue without a substantial number of tumor cells). For example, the γδ T cells may be from a region of skin (e.g., healthy skin) separate from a nearby or adjacent cancer tissue.

The γδ T cells that are dominant in the blood are primarily Vδ2 T cells, while the γδ T cells that are dominant in the non-haematopoietic tissues are primarily Vδ1 T cells, such that Vδ1 T cells comprise about 70-80% of the non-haematopoietic tissue-resident γδ T cell population. However, some Vδ2 T cells are also found in non-haematopoietic tissues, e.g. in the gut, where they can comprise about 10-20% of γδ T cells (FIG. 6). Some γδ T cells that are resident in non-haematopoietic tissues express neither Vδ1 nor Vδ2 TCR and we have named them double negative (DN) γδ T cells. These DN γδ T cells are likely to be mostly Vδ3-expressing with a minority of Vδ5-expressing T cells. Therefore, the γδ T cells that are ordinarily resident in non-haematopoietic tissues and that are expanded by the method of the invention are preferably non-Vδ2 T cells, e.g. Vδ1 T cells, with the inclusion of a smaller amount of DN γδ T cells.

It will be appreciated by a skilled artisan that certain non-haematopoietic tissue can be highly vascularized and, in practice, a sample of non-haematopoietic tissue is vulnerable to contaminated with peripheral blood-resident cells. To avoid or minimize such contamination, care can be taken to ensure peripheral blood is omitted from isolation and expansion cultures, according to methods known in the art, such as through thoroughly washing the tissue in a suitable buffer to remove blood-resident cells. For example, in some embodiments, a population of γδ T cells isolated from lung tissue is not obtained by bronchoalveolar lavage.

Separation of Non-Haematopoietic Tissue-Resident γδ T Cells from Non-Haematopoietic Tissue In some embodiments, a critical step is the deliberate separation, e.g., after some days or weeks of culture, of non-haematopoietic tissue-resident T cells (e.g., within a mixed lymphocyte population, which may for example comprise as cells, natural killer (NK) cells, B cells, and γδ2 and non-γδ2 T cells) away from the non-haematopoietic cells (e.g. stromal cells, particularly fibroblasts) of the tissue from which the T cells were obtained. This permits the preferential and rapid expansion over the following days and weeks of non-haematopoietic tissue-derived Vδ1 T cells and DN γδ T cells.

The invention provides methods involving separation of γδ T cells (e.g., non-Vδ2 T cells, e.g., Vδ1 T cells and/or DN T cells) from a non-haematopoietic tissue (e.g., skin, e.g., skin obtained by punch biopsy). In one embodiment, separation of the γδ T cells from non-haematopoietic cells comprises culturing the γδ T cells and the non-haematopoietic cells on a synthetic scaffold configured to facilitate cell egress from the non-haematopoietic tissue. Any scaffold suitable for lymphocyte separation from a solid tissue can be used. Synthetic scaffolds may be constructed from natural and/or synthetic materials such as polymers (e.g., natural or synthetic polymers, e.g., poly vinyl pyrolidones, polymethylmethacrylate, methyl cellulose, polystyrene, polypropylene, polyurethane), ceramics (e.g., tricalcium phosphate, calcium aluminate, calcium hydroxyapatite), or metals (tantalum, titanium, platinum and metals in the same element group as platinum, niobium, hafnium, tungsten, and combinations of alloys thereof). Biological factors (e.g., collagens (e.g., collagen I or collagen II), fibronectins, laminins, integrins, angiogenic factors, anti-inflammatory factors, glycosaminoglycans, vitrogens, antibodies and fragments thereof, cytokines (e.g., IL-2 or IL-15 and combinations thereof), chemokines, and/or chemoattractants may be coated onto the scaffold surface or encapsulated within the scaffold material to enhance cell adhesion, migration, survival, or proliferation, according to methods known in the art. In some embodiments, the synthetic scaffold is a Cellfoam scaffold as described in the Clark protocol. Alternatively, other methods can be used to isolate lymphocytes from a number of other non-haematopoietic tissue types, e.g., by enzyme-based degradation of extracellular matrix components (e.g., collagenase).

A separation culture may be carried out for any duration from 1 hour (e.g., in the case of a simple digestion) to up to 42 days (in the case of a scaffold culture). In instances in which the separation step is performed on a scaffold, the culture may be carried out for at least 5 days (e.g., at least 6 days, at least 7 days, at least 8 days, at least 9 days, at least 10 days, at least 12 days, at least 14 days, at least 16 days, at least 18 days, at least 20 days, at least 21 days, at least 24 days, at least 28 days, at least 30 days, at least 35 days, or at least 40 days, e.g., between 7 and 14 days, between 14 and 21 days, or between 21 and 35 days, e.g., about 14 days or about 21 days).

During separation of γδ T cells (e.g., skin-derived γδ T cells and/or non-Vδ2 T cells, e.g., Vδ1 T cells and/or DN T cells), the a non-haematopoietic tissue and cells derived therefrom may be cultured in the presence of biological factors to enhance egress from the tissue or to promote viability of one or more subpopulations of cells. In some embodiments, the separation culture includes IL-2, e.g., IL-2 at a concentration of at least 10 IU/mL (e.g., from 10 IU/mL to 1,000 IU/mL, from 20 IU/mL to 800 IU/mL, from 25 IU/mL to 750 IU/mL, from 30 IU/mL to 700 IU/mL, from 40 IU/mL to 600 IU/mL, from 50 IU/mL to 500 IU/mL, from 75 IU/mL to 250 IU/mL, or from 100 IU/mL to 200 IU/mL, e.g., from 10 IU/mL to 20 IU/mL, from 20 IU/mL to 30 IU/mL, from 30 IU/mL to 40 IU/mL, from 40 IU/mL to 50 IU/mL, from 50 IU/mL to 75 IU/mL, from 75 IU/mL to 100 IU/mL, from 100 IU/mL to 150 IU/mL, from 150 IU/mL to 200 IU/mL, from 200 IU/mL to 500 IU/mL, or from 500 IU/mL to 1,000 IU/mL). In some embodiments, the separation culture includes IL-2 at a concentration of about 100 IU/mL. Additionally or alternatively, the separation culture may include IL-15, e.g., IL-15 at a concentration of at least 0.1 ng/mL (e.g., from 0.1 ng/mL to 10,000 ng/mL, from 1.0 ng/mL to 1,000 ng/mL, from 5 ng/mL to 800 ng/mL, from 10 ng/mL to 750 ng/mL, from 20 ng/mL to 500 ng/mL, from 50 ng/mL to 400 ng/mL, or from 100 ng/mL to 250 ng/mL, e.g., from 0.1 ng/mL to 1.0 ng/mL, from 1.0 ng/mL to 5.0 ng/mL, from 5.0 ng/mL to 10 ng/mL, from 10 ng/mL to 20 ng/mL, from 20 ng/mL to 50 ng/mL, from 50 ng/mL to 100 ng/mL, from 100 ng/mL to 200 ng/mL, from 200 ng/mL to 500 ng/mL, or from 500 ng/mL to 1,000 ng/mL). In some embodiments, the separation culture includes IL-15 at a concentration of about 20 ng/mL.

In some embodiments, the separation of the γδ T cells from the non-haematopoietic tissue includes culture in the presence of both IL-2 and IL-15, each at any of the concentration listed above. In some cases, the concentration of IL-2 is about 100 IU/mL, and the concentration of IL-15 is 20 ng/mL.

The γδ T cells (e.g., skin-derived γδ T cells and/or non-Vδ2 T cells, e.g., Vδ1 T cells and/or DN T cells) may be cultured in the absence of IL-6, IL-23, and IL-1β, or in the presence of low concentrations of these cytokines (e.g. less than 20 ng/mL), as the addition of this combination of cytokines can act to reduce proliferation of non-haematopoietic tissue-resident γδ T cells (e.g., skin-derived γδ T cells and/or non-Vδ2 T cells, e.g., Vδ1 T cells and/or DN T cells).

Upon separation from the non-haematopoietic tissue (e.g., skin), the γδ T cells will generally be part of a larger population of lymphocytes containing, for example, αβ T cells, B cells, and natural killer (NK) cells. In some embodiments, 1%-10% of the separated population of lymphocytes are γδ T cells prior to expansion (e.g., 1-10% of the separated population of skin-derived lymphocytes are γδ T cells prior to expansion). In most cases, the γδ T cell population (e.g., skin-derived γδ T cell population) will include a large population of Vδ1 T cells. In some embodiments, 1-10% of the separated population of lymphocytes (e.g., skin-derived lymphocytes) are Vδ1 T cells prior to expansion (e.g., Vδ1 T cells may represent over 50%, over 60%, over 70%, over 80%, or over 90% of the population of a separated population γδ T cells prior to expansion). In some instances, less than 10% of the separated population of γδ T cells are Vδ2 T cells prior to expansion (e.g., less than 10% of the separated population of skin-derived γδ T cells are Vδ2 T cells prior to expansion).

Non-Vδ1 T cells or non-DN T cells, such as Vδ2 T cells, αβ T cells, B cells, or NK cells, may be removed from the separated population of the γδ T cells (e.g., prior to, during, or after expansion).

Prior to expansion, separated γδ T cells (e.g., γδ T cells separated from skin, e.g., Vδ1 T cells separated from skin) have a distinct phenotype from corresponding haematopoietic tissue-derived cells (e.g., blood-derived γδ T cells, e.g., blood-derived Vδ2 T cells). For example, the separated population of γδ T cells may express a higher level of CCR3, CCR4, CCR7, CCR8, or CD103 than a reference population, e.g., a TCR activated population of non-haematopoietic tissue-resident γδ T cells or a corresponding population of haematopoietic tissue-derived cells (e.g., blood-derived γδ T cells, e.g., blood-derived Vδ2 T cells). In some embodiments, the separated population of γδ T cells includes at least 5%, 10%, 15%, 20%, 25%, 30%, 40%, 50%, 60%, 70%, 80%, 90% or more CCR3$^+$ cells; at least 5%, 10%, 15%, 20%, 25%, 30%, 40%, 50%, 60%, 70%, 80%, 90% or more CCR4$^+$ cells; at least 5%, 10%, 15%, 20%, 25%, 30%, 40%, 50%, 60%, 70%, 80%, 90% or more CCR7$^+$ cells; at least 5%, 10%, 15%, 20%, 25%, 30%, 40%, 50%, 60%, 70%, 80%, 90% or more CCR8$^+$ cells; and/or at least 5%, 10%, 15%, 20%, 25%, 30%, 40%, 50%, 60%, 70%, 80%, 90% or more CD103$^+$ cells. The separated population of γδ T cells may express one or more, two or more, three or more, four or more, five or more, or all six of CCR3, CCR4, CCR7, CCR8, or CD103.

In some embodiments, the separated population of γδ T cells (e.g., skin-derived γδ T cells, e.g., skin-derived Vδ1 T cells) expresses a higher level of NKGD2, CD56, CD69, and/or TIM3 than a reference population, e.g., a TCR activated population of non-haematopoietic tissue-resident γδ T cells or a corresponding population of haematopoietic tissue-derived cells (e.g., blood-derived γδ T cells, e.g., blood-derived Vδ2 T cells). In some embodiments, the separated population of γδ T cells includes at least 5%, 10%, 15%, 20%, 25%, 30%, 40%, 50%, 60%, 70%, 80%, 90% or more NKGD2$^+$ cells; at least 5%, 10%, 15%, 20%, 25%, 30%, 40%, 50%, 60%, 70%, 80%, 90% or more CD56$^+$ cells; at least 5%, 10%, 15%, 20%, 25%, 30%, 40%, 50%, 60%, 70%, 80%, 90% or more CD69$^+$ cells; and/or at least 5%, 10%, 15%, 20%, 25%, 30%, 40%, 50%, 60%, 70%, 80%, 90% or more TIM3$^+$ cells. The separated population of γδ T cells may express one or more, two or more, three or more, four or more, or all five of NKGD2, CD56, CD69, and/or TIM3.

The separated population of non-haematopoietic tissue-derived γδ T cells (e.g., skin-derived γδ T cells, e.g., skin-derived Vδ1 T cells) can also be characterized by function. Functional assays known in the art and illustrated in Example 3 can be performed to determine the functional differences between any non-haematopoietic tissue-derived cell of the invention (e.g., a separated population of γδ T cells, e.g., skin-derived Vδ1 T cells, or an expanded population of γδ T cells, e.g., skin-derived Vδ1 T cells) and a reference cell (e.g., a TCR activated population of non-haematopoietic tissue-resident γδ T cells or a corresponding population of haematopoietic tissue-derived cells, e.g., blood-derived γδ T cells, e.g., blood-derived Vδ2 T cells). In some embodiments, a separated population of non-haematopoietic tissue-derived γδ T cells (e.g., a separated population of γδ T cells not in contact with substantial TCR pathway activation) secretes a higher level of IL-13 than a reference population (e.g., a TCR activated population of non-haematopoietic tissue-resident γδ T cells, e.g., an anti-CD3 activated population of non-haematopoietic tissue-resident γδ T cells). For instance, a separated population of non-haematopoietic tissue-derived γδ T cells (e.g., skin-derived γδ T cells and/or non-Vδ2 T cells, e.g., Vδ1 T cells and/or DN T cells) may secrete 1.1-fold, 1.2-fold, 1.3-fold, 1.4-fold, 1.5-fold, 2-fold, 3-fold, 4-fold, 5-fold, 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, or greater the concentration of IL-13 relative to a reference population of cells (e.g., a TCR activated population of non-haematopoietic tissue-resident γδ T cells, e.g., an anti-CD3 activated population of non-haematopoietic tissue-resident γδ T cells). Similarly, the number or frequency of non-haematopoietic tissue-derived γδ T cells in the separated population that secrete IL-13 may be greater relative to a reference population of cells (e.g., a TCR activated population of non-haematopoietic tissue-resident γδ T cells, e.g., an anti-CD3 activated population of non-haematopoietic tissue-resident γδ T cells). For example, the frequency of IL-13 secreting cells within the separated population of γδ T cells (e.g., the frequency of IL-13 secreting cells within the separated population of Vδ1 T cells) may be greater than a reference population of cells (a TCR activated population of non-haematopoietic tissue-resident γδ T cells, e.g., an anti-CD3 activated population of non-haematopoietic tissue-resident γδ T cells). In some embodiments, the frequency of IL-13 secreting cells within the separated population of γδ T cells (e.g., the frequency of IL-13 secreting cells within the separated population of DN T cells or Vδ1 T cells of the invention) is at least 1% greater, at least 2% greater, at least 3% greater, at least 4% greater, at least 5% greater, at least 6% greater, at least 7% greater, at least 8% greater, at least 9% greater, at least 10% greater, at least 20% greater, at least 30% greater, at least 40% greater, at least 50% greater, at least 60% greater, at least 70% greater, at least 80% greater, at least 90% greater, or up to 100% greater than a reference population of cells (a TCR activated population of non-haematopoietic tissue-resident γδ T cells, e.g., an anti-CD3 activated population of non-haematopoietic tissue-resident γδ T cells).

Expansion of Non-Haematopoietic Tissue-Resident γδ T Cells

The invention features methods of expanding non-haematopoietic tissue-resident γδ T cells (e.g., skin-derived γδ T cells and/or non-Vδ2 T cells, e.g., Vδ1 T cells and/or DN T cells). These methods may be carried out in vitro. In some embodiments, the non-haematopoietic tissue-resident γδ T cells are expanded from a population of γδ T cells that has been separated from non-haematopoietic tissue according to methods described above. In general, non-haematopoietic tissue-resident γδ T cells are capable of spontaneously expanding upon removal of physical contact with stromal cells (e.g., skin fibroblasts). Thus, the scaffold-based culture methods described above can be used to induce such separation, resulting in de-repression of the γδ T cells to trigger expansion. Accordingly, in some embodiments, no substantial TCR pathway activation is present during the expansion step (e.g., no exogenous TCR pathway activators are included in the culture). Further, the invention provides methods of expanding non-haematopoietic tissue-resident γδ T cells, wherein the methods do not involve contact with feeder cells, tumor cells, and/or antigen-presenting cells.

The inventors of the present invention have developed expansion protocols involving culturing non-haematopoietic tissue-resident γδ T cells in the presence of effective cocktails of biological factors to support efficient γδ T cell expansion. In one embodiment, the present invention provides a method of expanding γδ T cells by providing a population of γδ T cells obtained from a non-haematopoietic tissue (e.g., a separated population of non-haematopoietic tissue-derived γδ T cells, e.g., a population separated according to the methods described herein) and culturing the γδ T cells in the presence of IL-2, IL-4, IL-15, and/or IL-21. These cytokines or analogues thereof can be cultured with the cells for a duration (e.g., at least 5 days, at least 6 days, at least 7 days, at least 8 days, at least 9 days, at least 10 days, at least 11 days, at least 12 days, at least 13 days, at least 14 days, at least 21 days, at least 28 days, or longer, e.g., from 5 days to 40 days, from 7 days to 35 days, from 14 days 28 days, or about 21 days) in an amount effective to produce an expanded population of γδ T cells.

In some embodiments, the amount of IL-2 effective to produce an expanded population of γδ T cells is from 1 IU/mL to 2,000 IU/mL (e.g., from 5 IU/mL to 1,000 IU/mL, from 10 IU/mL to 500 IU/mL, from 20 IU/mL to 400 IU/mL, from 50 IU/mL to 250 IU/mL, or about 100 IU/mL, e.g., from 5 IU/mL to 10 IU/mL, from 10 IU/mL to 20 IU/mL, from 20 IU/mL to 30 IU/mL, from 30 IU/mL to 40 IU/mL, from 40 IU/mL to 50 IU/mL, from 50 IU/mL to 60 IU/mL, from 60 IU/mL to 70 IU/mL, from 70 IU/mL to 80 IU/mL, from 80 IU/mL to 90 IU/mL, from 90 IU/mL to 100 IU/mL, from 100 IU/mL to 120 IU/mL, from 120 IU/mL to 140 IU/mL, from 140 IU/mL to 150 IU/mL, from 150 IU/mL to 175 IU/mL, from 175 IU/mL to 200 IU/mL, from 200 IU/mL to 300 IU/mL, from 300 IU/mL to 400 IU/mL, from 400 IU/mL to 500 IU/mL, from 500 IU/mL to 1,000 IU/mL, from 1,000 IU/mL to 1,500 IU/mL, from 1,500 IU/mL to 2,000 IU/mL, or greater). In some embodiments, the amount of IL-2 effective to produce an expanded population of γδ T cells is about 100 IU/mL.

In some embodiments, the amount of IL-4 effective to produce an expanded population of γδ T cells (e.g., skin-derived γδ T cells and/or non-Vδ2 T cells, e.g., Vδ1 T cells and/or DN T cells) is at least 0.1 ng/mL (e.g., from 0.1 ng/mL to 10,000 ng/mL, from 1.0 ng/mL to 1,000 ng/mL, from 5 ng/mL to 800 ng/mL, from 10 ng/mL to 750 ng/mL, from 20 ng/mL to 500 ng/mL, from 50 ng/mL to 400 ng/mL, or from 100 ng/mL to 250 ng/mL, e.g., from 0.1 ng/mL to 1.0 ng/mL, from 1.0 ng/mL to 5.0 ng/mL, from 5.0 ng/mL to 10 ng/mL, from 10 ng/mL to 20 ng/mL, from 20 ng/mL to 50 ng/mL, from 50 ng/mL to 100 ng/mL, from 100 ng/mL to 200 ng/mL, from 200 ng/mL to 500 ng/mL, or from 500 ng/mL to 1,000 ng/mL). In some embodiments, the amount of IL-4 effective to produce an expanded population of γδ T cells is about 5 ng/mL.

In some embodiments, the amount of IL-15 effective to produce an expanded population of γδ T cells (e.g., skin-derived γδ T cells and/or non-Vδ2 T cells, e.g., Vδ1 T cells and/or DN T cells) is at least 0.1 ng/mL (e.g., from 0.1 ng/mL to 10,000 ng/mL, from 1.0 ng/mL to 1,000 ng/mL, from 5 ng/mL to 800 ng/mL, from 10 ng/mL to 750 ng/mL, from 20 ng/mL to 500 ng/mL, from 50 ng/mL to 400 ng/mL, or from 100 ng/mL to 250 ng/mL, e.g., from 0.1 ng/mL to 1.0 ng/mL, from 1.0 ng/mL to 5.0 ng/mL, from 5.0 ng/mL to 10 ng/mL, from 10 ng/mL to 20 ng/mL, from 20 ng/mL to 50 ng/mL, from 50 ng/mL to 100 ng/mL, from 100 ng/mL to 200 ng/mL, from 200 ng/mL to 500 ng/mL, or from 500 ng/mL to 1,000 ng/mL). In some embodiments, the amount of IL-15 effective to produce an expanded population of γδ T cells is about 10 ng/mL.

In some embodiments, the amount of IL-21 effective to produce an expanded population of γδ T cells (e.g., skin-derived γδ T cells and/or non-Vδ2 T cells, e.g., Vδ1 T cells and/or DN T cells) is at least 0.1 ng/mL (e.g., from 0.1 ng/mL to 10,000 ng/mL, from 1.0 ng/mL to 1,000 ng/mL, from 5 ng/mL to 800 ng/mL, from 10 ng/mL to 750 ng/mL, from 20 ng/mL to 500 ng/mL, from 50 ng/mL to 400 ng/mL, or from 100 ng/mL to 250 ng/mL, e.g., from 0.1 ng/mL to 1.0 ng/mL, from 1.0 ng/mL to 5.0 ng/mL, from 5.0 ng/mL to 10 ng/mL, from 10 ng/mL to 20 ng/mL, from 20 ng/mL to 50 ng/mL, from 50 ng/mL to 100 ng/mL, from 100 ng/mL to 200 ng/mL, from 200 ng/mL to 500 ng/mL, or from 500 ng/mL to 1,000 ng/mL). In some embodiments, the amount of IL-21 effective to produce an expanded population of γδ T cells is about 10 ng/mL. In other embodiments, the amount of IL-21 effective to produce an expanded population of γδ T cells is about 10 ng/mL.

Substitution or addition of other factors in the expansion culture of non-haematopoietic tissue-resident γδ T cells is also provided herein. For example, in some embodiments, any one or more factors selected from the group consisting of IL-6, IL-7, IL-8, IL-9, IL-12, IL-18, IL-33, IGF-1, IL-1β, human platelet lysate (HPL), and stromal cell-derived factor-1 (SDF-1) is include in addition to, or in substitution of, any one of IL-2, IL-4, IL-15, and IL-21. Suitable concentrations for each of these factors are provided in Example 3, at Table 2.

It will be understood that the amount of each of the above cytokines required to produce an expanded population of γδ T cells will depend of the concentrations of one or more of the other cytokines. For example, if the concentration of IL-2 is increased or decreased, the concentration of IL-15 may be accordingly decreased or increased, respectively. As noted above, the amount effective to produce an expanded population refers herein to composite effect of all factors on cell expansion.

In some embodiments, the γδ T cells are simultaneously exposed to each of the factors (e.g., the γδ T cells are simultaneously exposed to the IL-2, IL-4, IL-15, and IL-21, e.g., for at least 5 days). In other instances, the γδ T cells are exposed to certain factors prior to culture with other factors. For instance, the expansion culture can be gradually supplied with additional factors over the course of expansion, or, alternatively, the γδ T cells can be transferred from a culture of one factor or group of factors to another.

In some embodiments, the γδ T cells are expanded in culture for a period of several hours (e.g., about 2, 3, 4, 5, 6, 7, 8, 9, 10, 15, 18, or 21 hours) to about 35 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 days). In one embodiment, the γδ T cells are expanded for a period of 14 to 21 days. Thus, including a separation culture period (e.g., of 1 to 40 days, e.g., 14 to 21 days), the separation and expansion steps, in some embodiments, can last between 28 and 56 days, or about 41 days.

Methods of expansion provide an expanded population of γδ T cells that is greater in number than a reference population. In some embodiments, the expanded population of γδ T cells is greater in number than the separated population of γδ T cells prior to the expansion step (e.g., at least 2-fold in number, at least 3-fold in number, at least 4-fold in number, at least 5-fold in number, at least 6-fold in number, at least 7-fold in number, at least 8-fold in number, at least 9-fold in number, at least 10-fold in number, at least 15-fold in number, at least 20-fold in number, at least 25-fold in number, at least 30-fold in number, at least 35-fold in number, at least 40-fold in number, at least 50-fold in number, at least 60-fold in number, at least 70-fold in number, at least 80-fold in number, at least 90-fold in number, at least 100-fold in number, at least 200-fold in number, at least 300-fold in number, at least 400-fold in number, at least 500-fold in number, at least 600-fold in number, at least 700-fold in number, at least 800-fold in number, at least 900-fold in number, at least 1,000-fold in number at least 5,000-fold in number, at least 10,000-fold in number, or more relative to the separated population of γδ T cells prior to the expansion step).

Thus, the invention provides a means to produce large populations of non-haematopoietic tissue-derived γδ T cells (e.g., skin-derived γδ T cells and/or non-Vδ2 T cells, e.g., Vδ1 T cells and/or DN T cells) at high rates (e.g., by removing stromal cell contact and/or TCR stimulation, or by culturing in the presence of an effective amount of factors). In some embodiments, the expansion step described herein expands the γδ T cells at a low population doubling time, which is given by the following equation:

$$\text{Doubling Time} = \frac{\text{duration} * \log(2)}{\log(\text{final Concentration}) - \log(\text{Initial Concentration})}$$

Given the information provided herein, e.g., in Example 3, below, a skilled artisan will recognize that the invention provides methods of expanding non-haematopoietic tissue-derived γδ T cells (e.g., skin-derived γδ T cells and/or non-Vδ2 T cells, e.g., Vδ1 T cells and/or DN T cells) at a population doubling time of less than 5 days (e.g., less than 4.5 days, less than 4.0 days, less than 3.9 days, less than 3.8 days, less than 3.7 days, less than 3.6 days, less than 3.5 days, less than 3.4 days, less than 3.3 days, less than 3.2 days, less than 3.1 days, less than 3.0 days, less than 2.9 days, less than 2.8 days, less than 2.7 days, less than 2.6 days, less than 2.5 days, less than 2.4 days, less than 2.3 days, less than 2.2 days, less than 2.1 days, less than 2.0 days, less than 46 hours, less than 42 hours, less than 38 hours, less than 35 hours, less than 32 hours).

In some embodiments, within 7 days of culture, the expanded population of γδ T cells (e.g., the expanded population of Vδ1 T cells and/or DN T cells) comprises at least 10-fold the number of γδ T cells relative to the separated population of γδ T cells prior to expansion (e.g., at least 20-fold, at least 30-fold, at least 40-fold, at least 50-fold, at least 60-fold, at least 70-fold, at least 80-fold, at least 90-fold, at least 100-fold, at least 150-fold, at least 200-fold, at least 300-fold, at least 400-fold, at least 500-fold, at least 600-fold, at least 700-fold, at least 800-fold, at least 900-fold, at least 1,000-fold, at least 2,000-fold, at least 3,000-fold, at least 4,000-fold, at least 5,000-fold, at least 6,000-fold, at least 7,000-fold, or at least 8,000-fold the number of γδ T cells relative to the separated population of γδ T cells prior to expansion).

In some embodiments, within 14 days of culture, the expanded population of γδ T cells (e.g., the expanded population of Vδ1 T cells and/or DN T cells) comprises at least 20-fold the number of γδ T cells relative to the separated population of γδ T cells prior to expansion (e.g., at least 30-fold, at least 40-fold, at least 50-fold, at least 60-fold, at least 70-fold, at least 80-fold, at least 90-fold, at least 100-fold, at least 150-fold, at least 200-fold, at least 300-fold, at least 400-fold, at least 500-fold, at least 600-fold, at least 700-fold, at least 800-fold, at least 900-fold, at least 1,000-fold, at least 2,000-fold, at least 3,000-fold, at least 4,000-fold, at least 5,000-fold, at least 6,000-fold, at least 7,000-fold, at least 8,000-fold, at least 9,000-fold, or at least 10,000-fold the number of γδ T cells relative to the separated population of γδ T cells prior to expansion). In some embodiments, within 21 days of culture, the expanded population of γδ T cells (e.g., the expanded population of Vδ1 T cells and/or DN T cells) comprises at least 50-fold the number of γδ T cells relative to the separated population of γδ T cells prior to expansion (e.g., at least 60-fold, at least 70-fold, at least 80-fold, at least 90-fold, at least 100-fold, at least 150-fold, at least 200-fold, at least 300-fold, at least 400-fold, at least 500-fold, at least 600-fold, at least 700-fold, at least 800-fold, at least 900-fold, at least 1,000-fold, at least 2,000-fold, at least 3,000-fold, at least 4,000-fold, at least 5,000-fold, at least 6,000-fold, at least 7,000-fold, at least 8,000-fold, at least 9,000-fold, or least 10,000-fold the number of γδ T cells relative to the separated population of γδ T cells prior to expansion). In some embodiments, within 28 days of culture, the expanded population of γδ T cells (e.g., the expanded population of Vδ1 T cells and/or DN T cells) comprises at least 100-fold the number of γδ T cells relative to the separated population of γδ T cells prior to expansion (e.g., at least 110-fold, at least 120-fold, at least 130-fold, at least 140-fold, at least 150-fold, at least 200-fold, at least 300-fold, at least 400-fold, at least 500-fold, at least 600-fold, at least 700-fold, at least 800-fold, at least 900-fold, at least 1,000-fold, at least 2,000-fold, at least 3,000-fold, at least 4,000-fold, at least 5,000-fold, at least 6,000-fold, at least 7,000-fold, at least 8,000-fold, at least 9,000-fold, at least 10,000-fold, at least 12,000-fold, or at least 15,000-fold the number of γδ T cells relative to the separated population of γδ T cells prior to expansion).

Non-haematopoietic tissue-derived γδ T cells (e.g., skin-derived γδ T cells and/or non-Vδ2 T cells, e.g., Vδ1 T cells and/or DN T cells) expanded by the methods provided herein can have a phenotype well-suited for anti-tumor efficacy. In some embodiments, the expanded population of γδ T cells (e.g., skin-derived Vδ1 T cells) has a greater mean expression of CD27 than a reference population (e.g., the separated population of γδ T cells prior to the expansion step). In some embodiments, the expanded population of γδ T cells has a mean expression of CD27 that is at least 2-fold relative to the separated population of γδ T cells (e.g., at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 40-fold, at least 50-fold, at least 60-fold, at least 70-fold, at least 80-fold, at least 90-fold, at least 100-fold, at least 150-fold, at least 200-fold, at least 300-fold, at least 400-fold, at least 500-fold, at least 600-fold, at least 700-fold, at least 800-fold, at least 900-fold, at least 1,000-fold, at least 5,000-fold, at least 10,000-fold, at least 20,000-fold, or more, relative to the separated population of γδ T cells).

A distinct portion of the expanded population of γδ T cells (e.g., skin-derived γδ T cells and/or non-Vδ2 T cells, e.g., Vδ1 T cells and/or DN T cells) may upregulate CD27, while another portion is $CD27^{low}$ or $CD27^-$. In this case, the frequency of $CD27^+$ cells in the expanded population relative to the separated population of γδ T cells may be greater. For example, the expanded population of γδ T cells may have at least a 5% greater frequency of $CD27^+$ cells relative to that of the separated population of γδ T cells prior to expansion (e.g., at least a 10%, at least a 15%, at least a 20%, at least a 25%, at least a 30%, at least a 35%, at least a 40%, at least a 45%, at least a 50%, at least a 60%, at least a 70%, at least an 80%, at least a 90%, or up to 100% greater frequency of $CD27^+$ cells relative to that of the separated population of γδ T cells prior to expansion). In some embodiments, the number of $CD27^+$ cells in the expanded population relative to the separated population of γδ T cells may be increased. For example, the expanded population of γδ T cells may have at least 2-fold the number of $CD27^+$ cells relative to the separated population of γδ T cells prior to expansion (e.g., at least a 10%, at least a 15%, at least a 20%, at least a 25%, at least a 30%, at least a 35%, at least a 40%, at least a 45%, at least a 50%, at least a 60%, at least a 70%, at least an 80%, at least a 90%, or up to 100% greater frequency of $CD27^+$ cells relative to that of the separated population of γδ T cells prior to expansion).

Methods of expansion as provided herein, in some embodiments, yield an expanded population non-haematopoietic tissue-derived γδ T cells (e.g., skin-derived γδ T cells and/or non-Vδ2 T cells, e.g., Vδ1 T cells and/or DN T cells) having a low expression of TIGIT, relative to a reference population (e.g., the separated population of γδ T cells prior to the expansion step). In some embodiments, the expanded population of γδ T cells has a lower mean expression of TIGIT than a reference population (e.g., the separated population of γδ T cells prior to the expansion step). In some embodiments, the expanded population of γδ T cells has a mean expression of TIGIT that is at least 10% less than the separated population of γδ T cells (e.g., at least 20% less, at least 30% less, at least 40% less, at least 50% less, at least 60% less, at least 70% less, at least 80% less, at least 90% less, or up to 100% less than the separated population of γδ T cells).

A distinct portion of the expanded population of γδ T cells (e.g., skin-derived γδ T cells and/or non-Vδ2 T cells, e.g., Vδ1 T cells and/or DN T cells) may express TIGIT, e.g., high levels of TIGIT, while another portion is $TIGIT^{low}$ or $TIGIT^-$. In this case, the frequency of $TIGIT^+$ cells in the expanded population relative to the separated population of γδ T cells may be lower. For example, the expanded population of γδ T cells may have at least a 5% lower frequency of $TIGIT^+$ cells relative to that of the separated population of γδ T cells prior to expansion (e.g., at least a 10%, at least a 15%, at least a 20%, at least a 25%, at least a 30%, at least a 35%, at least a 40%, at least a 45%, at least a 50%, at least a 60%, at least a 70%, at least an 80%, at least a 90%, or up to 100% lower frequency of TIGIT cells relative to that of the separated population of γδ T cells prior to expansion). In some embodiments, the number of $TIGIT^+$ cells in the expanded population relative to the separated population of γδ T cells prior to expansion may be lower. For example, the expanded population of γδ T cells may have at least 10% fewer $TIGIT^+$ cells relative to the number of $TIGIT^+$ cells in the separated population of γδ T cells prior to expansion (e.g., at least a 10%, at least a 15%, at least a 20%, at least a 25%, at least a 30%, at least a 35%, at least a 40%, at least a 45%, at least a 50%, at least a 60%, at least a 70%, at least an 80%, at least a 90%, or up to 100% fewer $TIGIT^+$ cells relative to the number of $TIGIT^+$ cells in the separated population of γδ T cells prior to expansion).

In some embodiments, the expanded population of γδ T cells (e.g., skin-derived γδ T cells or non-Vδ2 T cells, e.g., Vδ1 T cells and/or DN T cells) has a high number or frequency of $CD27^+$ cells and a low frequency of $TIGIT^+$ cells. In some embodiments, the expanded population of γδ T cells has a high frequency of $CD27^+TIGIT^-$ cells relative to a reference population (e.g., relative to a separated population of γδ T cells prior to expansion). For instance, the expanded population of γδ T cells may have at least a 5% greater frequency of $CD27^+ TIGIT^-$ cells relative to that of the separated population of γδ T cells prior to expansion (e.g., at least a 10%, at least a 15%, at least a 20%, at least a 25%, at least a 30%, at least a 35%, at least a 40%, at least a 45%, at least a 50%, at least a 60%, at least a 70%, at least an 80%, at least a 90%, or up to 100% greater frequency of $CD27^+ TIGIT^-$ cells relative to that of the separated population of γδ T cells prior to expansion). In some embodiments, the number of $CD27^+ TIGIT^-$ cells in the expanded population relative to the separated population of γδ T cells may be increased. For example, the expanded population of γδ T cells may have at least 2-fold the number of $CD27^+ TIGIT^-$ cells relative to the separated population of γδ T cells prior to expansion (e.g., at least a 10%, at least a 15%, at least a 20%, at least a 25%, at least a 30%, at least a 35%, at least a 40%, at least a 45%, at least a 50%, at least a 60%, at least a 70%, at least an 80%, at least a 90%, or up to 100% greater frequency of CD27$^+$TIGIT$^-$ cells relative to that of the separated population of γδ T cells prior to expansion).

In some instances, the mean expression of TIGIT on a population of CD27$^+$ γδ T cells in an expanded population of γδ T cells (e.g., skin-derived γδ T cells and/or non-Vδ2 T cells, e.g., Vδ1 T cells and/or DN T cells) is low relative to a reference population. In some embodiments, the expanded population of CD27$^+$ γδ T cells has a lower mean expression of TIGIT than a reference population (e.g., the separated population of CD27$^+$ γδ T cells prior to the expansion step). In some embodiments, the expanded population of CD27$^+$ γδ T cells has a mean expression of TIGIT that is at least 10% less than the separated population of CD27$^+$ γδ T cells (e.g., at least 20% less, at least 30% less, at least 40% less, at least 50% less, at least 60% less, at least 70% less, at least 80% less, at least 90% less, or up to 100% less than the separated population of CD27$^+$ γδ T cells).

Additionally or alternatively, the median expression of CD27 on a population of TIGIT$^-$ γδ T cells in an expanded population of γδ T cells (e.g., skin-derived γδ T cells and/or non-Vδ2 T cells, e.g., Vδ1 T cells and/or DN T cells) is high relative to a reference population. For example, the expanded population of TIGIT$^-$ γδ T cells may have at least a 5% greater frequency of CD27$^+$ cells relative to that of the separated population of TIGIT$^-$ γδ T cells prior to expansion (e.g., at least a 10%, at least a 15%, at least a 20%, at least a 25%, at least a 30%, at least a 35%, at least a 40%, at least a 45%, at least a 50%, at least a 60%, at least a 70%, at least an 80%, at least a 90%, or up to 100% greater frequency of CD27$^+$ cells relative to that of the separated population of TIGIT$^-$ γδ T cells prior to expansion). In some embodiments, the number of CD27$^+$ cells in the expanded population relative to the separated population of TIGIT$^-$ γδ T cells may be increased. For example, the expanded population of TIGIT$^-$ γδ T cells may have at least 2-fold the number of CD27$^+$ cells relative to the separated population of TIGIT$^-$ γδ T cells prior to expansion (e.g., at least a 10%, at least a 15%, at least a 20%, at least a 25%, at least a 30%, at least a 35%, at least a 40%, at least a 45%, at least a 50%, at least a 60%, at least a 70%, at least an 80%, at least a 90%, or up to 100% greater frequency of CD27$^+$ cells relative to that of the separated population of TIGIT$^-$ γδ T cells prior to expansion).

An increase or decrease in expression of other markers can be additionally or alternatively used to characterize one or more expanded populations of non-haematopoietic tissue-derived γδ T cells (e.g., skin-derived γδ T cells and/or non-Vδ2 T cells, e.g., Vδ1 T cells and/or DN T cells), including CD124, CD215, CD360, CTLA4, CD1b, BTLA, CD39, CD45RA, Fas Ligand, CD25, ICAM-1, CD31, KLRG1, CD30, CD2, NKp44, NKp46, ICAM-2, CD70, CD28, CD103, NKp30, LAG3, CCR4, CD69, PD-1, and CD64. In some instances, the expanded population of γδ T cells (e.g., skin-derived γδ T cells and/or non-Vδ2 T cells, e.g., Vδ1 T cells and/or DN T cells) has a greater mean expression of one or more of the markers selected from the group consisting of CD124, CD215, CD360, CTLA4, CD1b, BTLA, CD39, CD45RA, Fas Ligand, CD25, ICAM-1, CD31, KLRG1, CD30, and CD2, relative to the separated population of γδ T cells, e.g., prior to expansion. Additionally or alternatively, the expanded population of γδ T cells (e.g., skin-derived γδ T cells and/or non-Vδ2 T cells, e.g., Vδ1 T cells and/or DN T cells) may have a greater frequency of cells expressing one or more of the markers selected from the group consisting of CD124, CD215, CD360, CTLA4, CD1b, BTLA, CD39, CD45RA, Fas Ligand, CD25, ICAM-1, CD31, KLRG1, CD30, and CD2, relative to the separated population of γδ T cells. In some embodiments, the expanded population of γδ T cells (e.g., skin-derived γδ T cells and/or non-Vδ2 T cells, e.g., Vδ1 T cells and/or DN T cells) has a lower mean expression of one or more of the markers selected from the group consisting of NKp44, NKp46, ICAM-2, CD70, CD28, CD103, NKp30, LAG3, CCR4, CD69, PD-1, and CD64, relative to the separated population of γδ T cells. The expanded population may similarly have a lower frequency of cells expressing one or more of the markers selected from the group consisting of NKp44, NKp46, ICAM-2, CD70, CD28, CD103, NKp30, LAG3, CCR4, CD69, PD-1, and CD64, relative to the separated population of γδ T cells.

A non-haematopoietic tissue-resident γδ T cell produced by the method of the invention may thus have one or more of the following properties: (i) displays the phenotype CD69$^{high}$, TIM3$^{high}$ and CD28$^{low/absent}$; (ii) upregulates of one or more of CCR3, CD39, CD11b, and CD9; (iii) produces IFN-γ in response to an NKG2D ligand in the absence of TCR agonists; (iv) produces IL-13 in the absence of TCR agonists; (v) produces one or more of IFN-γ, TNF-α and GM-CSF in response to TCR activation; (vi) produces no or substantially no IL-17 in response to TCR activation; (vii) grows in culture medium containing IL-2 without additional growth factors; (viii) displays a cytotoxic T cell response in the absence of TCR agonists; and/or (ix) displays selective cytotoxicity for tumor cells over normal cells.

In some instances, a non-haematopoietic tissue-resident γδ T cell produced by the method of the invention produces IL-13 in the absence of TCR agonists and/or produces IFN-γ in response to an NKG2D ligand in the absence of TCR agonists.

Numerous basal culture media suitable for use in the proliferation of γδ T cells are available, in particular complete media, such as AIM-V, Iscoves medium and RPMI-1640 (Life Technologies). The medium may be supplemented with other media factors, such as serum, serum proteins and selective agents, such as antibiotics. For example, in some embodiments, RPMI-1640 medium containing 2 mM glutamine, 10% FBS, 10 mM HEPES, pH 7.2, 1% penicillin-streptomycin, sodium pyruvate (1 mM; Life Technologies), non-essential amino acids (e.g. 100 μM Gly, Ala, Asn, Asp, Glu, Pro and Ser; 1×MEM non-essential amino acids Life Technologies), and 10 μl/L β-mercaptoethanol. Conveniently, cells are cultured at 37° C. in a humidified atmosphere containing 5% CO$_2$ in a suitable culture medium.

The γδ T cells may be cultured as described herein in any suitable system, including stirred tank fermenters, airlift fermenters, roller bottles, culture bags or dishes, and other bioreactors, in particular hollow fiber bioreactors. The use of such systems is well-known in the art. General methods and techniques for culture of lymphocytes are well-known in the art.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected.

IV. Pharmaceutical Compositions and Methods of Treatment

The γδ T cells obtained by the method of the invention may be used as a medicament, for example for adoptive T cell therapy. This involves the transfer of γδ T cells obtained by the method of the invention into a patient. The therapy may be autologous, i.e., the γδ T cells may be transferred back into the same patient from which they were obtained, or the therapy may be allogeneic, i.e., the γδ T cells from one person may be transferred into a different patient. In instances involving allogeneic transfer, the γδ T cells may be substantially free of αβ T cells. For example, αβ T cells may be depleted from the γδ T cell population, e.g., after expansion, using any suitable means known in the art (e.g., by negative selection, e.g., using magnetic beads). A method of treatment may include; providing a sample of non-haematopoietic tissue obtained from a donor individual; culturing the γδ T cells from the sample as described above to produce an expanded population; and administering the expanded population of γδ T cells to a recipient individual.

The patient or subject to be treated is preferably a human cancer patient (e.g., a human cancer patient being treated for a solid tumor) or a virus-infected patient (e.g., a CMV-infected or HIV infected patient). In some instances, the patient has and/or is being treated for a solid tumor.

Because they are normally resident in non-haematopoietic tissues, tissue-resident Vδ1 T and DN γδ T cells are also more likely to home to and be retained within tumor masses than their systemic blood-resident counterparts and adoptive transfer of these cells is likely to be more effective at targeting solid tumors and potentially other non-haematopoietic tissue-associated immunopathologies.

As γδ T cells are non-MHC restricted, they do not recognize a host into which they are transferred as foreign, which means that they are less likely to cause graft-versus-host disease. This means that they can be used "off the shelf" and transferred into any recipient, e.g., for allogeneic adoptive T cell therapy.

Non-haematopoietic tissue-resident γδ T cells obtained by methods of the invention express NKG2D and respond to a NKG2D ligand (e.g. MICA), which is strongly associated with malignancy. They also express a cytotoxic profile in the absence of any activation and are therefore likely to be effective at killing tumor cells. For example, the non-haematopoietic tissue-resident γδ T cells obtained as described herein may express one or more, preferably all of IFN-γ, TNF-α, GM-CSF, CCL4, IL-13, Granulysin, Granzyme A and B, and Perforin in the absence of any activation. IL-17A may not be expressed.

The findings reported herein therefore provide compelling evidence for the practicality and suitability for the clinical application of the non-haematopoietic tissue-resident γδ T cells obtained by the method of the invention as an "off-the-shelf" immunotherapeutic reagent. These cells possess innate-like killing, have no MHC restriction and display improved homing to and/or retention within tumors than do other T cells.

In some embodiments, a method of treatment of an individual with a tumor in a non-haematopoietic tissue may include; providing a sample of said non-haematopoietic tissue obtained from a donor individual, culturing the γδ T cells from the sample as described above to produce an expanded population, and; administering the expanded population of γδ T cells to the individual with the tumor.

Pharmaceutical compositions may include expanded non-haematopoietic tissue-resident γδ T cells as described herein in combination with one or more pharmaceutically or physiologically acceptable carrier, diluents, or excipients. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Cryopreservation solutions which may be used in the pharmaceutical compositions of the invention include, for example, DMSO. Compositions can be formulated, e.g., for intravenous administration.

In one embodiment, the pharmaceutical composition is substantially free of, e.g., there are no detectable levels of a contaminant, e.g., of endotoxin or *mycoplasma*.

In some instances, a therapeutically effective amount of expanded γδ T cells obtained by the any of the methods described above can be administered in a therapeutically effective amount to a subject (e.g., for treatment of cancer, e.g. for treatment of a solid tumor). In some cases, the therapeutically effective amount of expanded γδ T cells (e.g., skin-derived γδ T cells and/or non-Vδ2 T cells, e.g., Vδ1 T cells and/or DN T cells) is less than $10 \times 10^{12}$ cells per dose (e.g., less than $9 \times 10^{12}$ cells per dose, less than $8 \times 10^{12}$ cells per dose, less than $7 \times 10^{12}$ cells per dose, less than $6 \times 10^{12}$ cells per dose, less than $5 \times 10^{12}$ cells per dose, less than $4 \times 10^{12}$ cells per dose, less than $3 \times 10^{12}$ cells per dose, less than $2 \times 10^{12}$ cells per dose, less than $1 \times 10^{12}$ cells per dose, less than $9 \times 10^{11}$ cells per dose, less than $8 \times 10^{11}$ cells per dose, less than $7 \times 10^{11}$ cells per dose, less than $6 \times 10^{11}$ cells per dose, less than $5 \times 10^{11}$ cells per dose, less than $4 \times 10^{11}$ cells per dose, less than $3 \times 10^{11}$ cells per dose, less than $2 \times 10^{11}$ cells per dose, less than $1 \times 10^{11}$ cells per dose, less than $9 \times 10^{10}$ cells per dose, less than $7.5 \times 10^{10}$ cells per dose, less than $5 \times 10^{10}$ cells per dose, less than $2.5 \times 10^{10}$ cells per dose, less than $1 \times 10^{10}$ cells per dose, less than $7.5 \times 10^{9}$ cells per dose, less than $5 \times 10^{9}$ cells per dose, less than $2.5 \times 10^{9}$ cells per dose, less than $1 \times 10^{9}$ cells per dose, less than $7.5 \times 10^{8}$ cells per dose, less than $5 \times 10^{8}$ cells per dose, less than $2.5 \times 10^{8}$ cells per dose, less than $1 \times 10^{8}$ cells per dose, less than $7.5 \times 10^{7}$ cells per dose, less than $5 \times 10^{7}$ cells per dose, less than $2.5 \times 10^{7}$ cells per dose, less than $1 \times 10^{07}$ cells per dose, less than $7.5 \times 10^{6}$ cells per dose, less than $5 \times 10^{6}$ cells per dose, less than $2.5 \times 10^{6}$ cells per dose, less than $1 \times 10^{6}$ cells per dose, less than $7.5 \times 10^{5}$ cells per dose, less than $5 \times 10^{5}$ cells per dose, less than $2.5 \times 10^{5}$ cells per dose, or less than $1 \times 10^{5}$ cells per dose).

In some embodiments, the therapeutically effective amount of expanded γδ T cells (e.g., skin-derived γδ T cells and/or non-Vδ2 T cells, e.g., Vδ1 T cells and/or DN T cells) is less than $10 \times 10^{12}$ cells over the course of treatment (e.g., less than $9 \times 10^{12}$ cells, less than $8 \times 10^{12}$ cells, less than $7 \times 10^{12}$ cells, less than $6 \times 10^{12}$ cells, less than $5 \times 10^{12}$ cells, less than $4 \times 10^{12}$ cells, less than $3 \times 10^{12}$ cells, less than $2 \times 10^{12}$ cells, less than $1 \times 10^{12}$ cells, less than $9 \times 10^{11}$ cells, less than $8 \times 10^{11}$ cells, less than $7 \times 10^{11}$ cells, less than $6 \times 10^{11}$ cells, less than $5 \times 10^{11}$ cells, less than $4 \times 10^{11}$ cells, less than $3 \times 10^{11}$ cells, less than $2 \times 10^{11}$ cells, less than $1 \times 10^{11}$ cells, less than $9 \times 10^{10}$ cells, less than $7.5 \times 10^{10}$ cells, less than $5 \times 10^{10}$ cells, less than $2.5 \times 10^{10}$ cells, less than $1 \times 10^{10}$ cells, less than $7.5 \times 10^{9}$ cells, less than $5 \times 10^{9}$ cells, less than $2.5 \times 10^{9}$ cells, less than $1 \times 10^{9}$ cells, less than $7.5 \times 10^{8}$ cells, less than $5 \times 10^{8}$ cells, less than $2.5 \times 10^{8}$ cells, less than $1 \times 10^{8}$ cells, less than $7.5 \times 10^{7}$ cells, less than $5 \times 10^{7}$ cells, less than $2.5 \times 10^{7}$ cells, less than $1 \times 10^{7}$ cells, less than $7.5 \times 10^{6}$ cells, less than $5 \times 10^{6}$ cells, less than $2.5 \times 10^{6}$ cells, less than 1×10$^6$ cells, less than 7.5×10$^5$ cells, less than 5×10$^5$ cells, less than 2.5×10$^5$ cells, or less than 1×10$^5$ cells over the course of treatment).

In some embodiments, a dose of expanded non-haematopoietic tissue-resident γδ T cells as described herein comprises about 1×10$^6$, 1.1×10$^6$, 2×10$^6$, 3.6×10$^6$, 5×10$^6$, 1×10$^7$, 1.8×10$^7$, 2×10$^7$, 5×10$^7$, 1×10$^8$, 2×10$^8$, or 5×10$^8$ cells/kg. In some embodiments, a dose of expanded non-haematopoietic tissue-resident γδ T cells (e.g., skin-derived γδ T cells and/or non-Vδ2 T cells, e.g., Vδ1 T cells and/or DN T cells) comprises at least about 1×10$^6$, 1.1×10$^6$, 2×10$^6$, 3.6×10$^6$, 5×10$^6$, 1×10$^7$, 1.8×10$^7$, 2×10$^7$, 5×10$^7$, 1×10, 2×10$^8$, or 5×10$^8$ cells/kg. In some embodiments, a dose of expanded non-haematopoietic tissue-resident γδ T cells (e.g., skin-derived γδ T cells and/or non-Vδ2 T cells, e.g., Vδ1 T cells and/or DN T cells) comprises up to about 1×10$^6$, 1.1×10$^6$, 2×10$^6$, 3.6×10$^6$, 5×10$^6$, 1×10$^7$, 1.8×10$^7$, 2×10$^7$, 5×10$^7$, 1×10$^8$, 2×10$^8$, or 5×10$^8$ cells/kg. In some embodiments, a dose of expanded non-haematopoietic tissue-resident γδ T cells (e.g., skin-derived γδ T cells and/or non-Vδ2 T cells, e.g., Vδ1 T cells and/or DN T cells) comprises about 1.1×10$^6$-1.8×10$^7$ cells/kg. In some embodiments, a dose of expanded non-haematopoietic tissue-resident γδ T cells (e.g., skin-derived γδ T cells and/or non-Vδ2 T cells, e.g., Vδ1 T cells and/or DN T cells) comprises about 1×10$^7$, 2×10$^7$, 5×10$^7$, 1×10$^8$, 2×10$^8$, 5×10$^8$, 1×10$^9$, 2×10$^9$, or 5×10$^9$ cells. In some embodiments, a dose of expanded non-haematopoietic tissue-resident γδ T cells (e.g., skin-derived γδ T cells and/or non-Vδ2 T cells, e.g., Vδ1 T cells and/or DN T cells) comprises at least about 1×10$^7$, 2×10$^7$, 5×10$^7$, 1×10$^8$, 2×10$^8$, 5×10$^8$, 1×10$^9$, 2×10$^9$, or 5×10$^9$ cells. In some embodiments, a dose of expanded non-haematopoietic tissue-resident γδ T cells (e.g., skin-derived γδ T cells and/or non-Vδ2 T cells, e.g., Vδ1 T cells and/or DN T cells) comprises up to about 1×10$^7$, 2×10$^7$, 5×10$^7$, 1×10$^8$, 2×10$^8$, 5×10$^8$, 1×10$^9$, 2×10$^9$, or 5×10$^9$ cells.

In one embodiment, the subject is administered 10$^4$ to 10$^6$ expanded non-haematopoietic tissue-resident γδ T cells (e.g., skin-derived γδ T cells and/or non-Vδ2 T cells, e.g., Vδ1 T cells and/or DN T cells) per kg body weight of the subject. In one embodiment, the subject receives an initial administration of a population of non-haematopoietic tissue-resident γδ T cells (e.g., an initial administration of 10$^4$ to 10$^6$ γδ T cells per kg body weight of the subject, e.g., 10$^4$ to 10$^5$ γδ T cells per kg body weight of the subject), and one or more (e.g., 2, 3, 4, or 5) subsequent administrations of expanded non-haematopoietic tissue-resident γδ T cells (e.g., one or more subsequent administration of 10$^4$ to 10$^6$ expanded non-haematopoietic tissue-resident γδ T cells per kg body weight of the subject, e.g., 10$^4$ to 10$^5$ expanded non-haematopoietic tissue-resident γδ T cells per kg body weight of the subject). In one embodiment, the one or more subsequent administrations are administered less than 15 days, e.g., 14, 13, 12, 11, 10, 9, 8, 7, 6, 5, 4, 3, or 2 days after the previous administration, e.g., less than 4, 3, or 2 days after the previous administration. In one embodiment, the subject receives a total of about 10$^6$ γδ T cells per kg body weight of the subject over the course of at least three administrations of a population of γδ T cells, e.g., the subject receives an initial dose of 1×10$^5$ γδ T cells, a second administration of 3×10$^5$ γδ T cells, and a third administration of 6×10$^5$ γδ T cells, and, e.g., each administration is administered less than 4, 3, or 2 days after the previous administration.

The non-haematopoietic tissue-resident γδ T cells obtained by the method of the invention may also be used for CAR-T therapy. This involves the generation of engineered T cell receptors (TCRs) to re-program the T cell with a new specificity, e.g. the specificity of a monoclonal antibody. The engineered TCR may make the T cells specific for malignant cells and therefore useful for cancer immunotherapy. For example, the T cells may recognize cancer cells expressing a tumor antigen, such as a tumor associated antigen that is not expressed by normal somatic cells from the subject tissue. Thus, the CAR-modified T cells may be used for adoptive T cell therapy of, for example, cancer patients.

The use of blood-resident γδ T cells for CAR has been described. However, non-haematopoietic tissue-resident γδ T cells obtained by the method of the invention are likely to be particularly good vehicles for CAR-T approaches, as they can be transduced with chimeric antigen-specific TCRs while retaining their innate-like capabilities of recognizing transformed cells, and are likely to have better tumor penetration and retention capabilities than either blood-resident γδ T cells or conventional, systemic αβ T cells. Furthermore, their lack of MHC dependent antigen presentation reduces the potential for graft-versus-host disease and permits them to target tumors expressing low levels of MHC. Likewise, their non-reliance upon conventional co-stimulation, for example via engagement of CD28 enhances the targeting of tumors expressing low levels of ligands for co-stimulatory receptors.

In some embodiments, one or more additional therapeutic agents can be administered to the subject. The additional therapeutic agent may be selected from the group consisting of an immunotherapeutic agent, a cytotoxic agent, a growth inhibitory agent, a radiation therapy agent, an anti-angiogenic agent, or a combination of two or more agents thereof. The additional therapeutic agent may be administered concurrently with, prior to, or after administration of the expanded γδ T cells. The additional therapeutic agent may be an immunotherapeutic agent, which may act on a target within the subject's body (e.g., the subject's own immune system) and/or on the transferred γδ T cells.

The administration of the compositions may be carried out in any convenient manner. The compositions described herein may be administered to a patient transarterially, subcutaneously, intradermally, intratumorally, intranodally, intramedullary, intramuscularly, by intravenous injection, or intraperitoneally, e.g., by intradermal or subcutaneous injection. The compositions of non-haematopoietic tissue-resident γδ T cells may be injected directly into a tumor, lymph node, or site of infection.

EXAMPLES

In most adults, Vδ2 cells comprise at steady-state only a small and highly variable component of blood T cells (0.01-5%), but the cells expand rapidly, transiently reaching up to ~25% of CD3$^+$ cells, following challenge by a broad spectrum of agents, including numerous bacteria and parasites. A major basis for this response is the Vδ2 TCR-mediated recognition of low molecular weight "phospho-moieties", including hydroxyl-methyl but-2-enyl pyrophosphate (HMBPP), an intermediate in a critical microbial pathway of synthesis of cholesterol and of other lipids that are used to modify proteins, e.g. by geranylation or farnesylation. In primates, this synthesis occurs via the mevalonate pathway, one intermediate of which, isopentenyl pyrophosphate (IPP), is expressed at very high levels in virus-infected and transformed cells, and is also a target of Vδ2 TCR-mediated recognition.

In addition, most Vδ2 T cells express high levels of the NKG2D receptor that can activate or co-stimulate (together with the T cell receptor (TCR)) the cells' cytolytic potentials upon engaging NKG2D ligands, e.g. MICA, MICB, and ULBP. Those ligands are host proteins that are upregulated when cells are exposed to agents such as oxidative or osmotic stress or ultraviolet light. These agents promote hyper-active signaling of the epidermal growth factor receptor (EGFR) pathway, which is also commonly dysregulated in human solid tumors.

The capacity of Vδ2 T cells to detect transformed cells using their TCRs and/or NKG2D, together with their powerful cytolytic capabilities, and an overt potential to present antigens to CD8⁺ T cells, have collectively provoked the view that Vδ2 T cells might be clinically exploited to deliver cancer immunotherapy. This may be achieved by the cells' adoptive transfer, in which regard the failure of γδ T cells to be restricted by MHC significantly and beneficially limits the potential for graft-versus-host disease (GvHD). In order to achieve this, blood-resident Vγ9Vδ2 γδ T cells can be expanded ex vivo by addition of cytokines such as interleukin-2 (IL-2), together with exogenous TCR-activating agents such as phospho-moieties (e.g., BrHPP), or together with clinically-approved bisphosphonates (e.g., zoledronic acid), which inhibit farnesyl pyrophosphate synthase in the mevalonate pathway, thereby inducing accumulation of the TCR-activating moiety, IPP. However, chronic activation of Vγ9Vδ2 cells via agents such as BrHPP can lead progressively to cellular exhaustion and diminished potential for cytotoxicity.

Alternatively, the patients' own γδ T cells may be activated in situ using either pharmacologically modified forms of HMBPP, or clinically-approved aminobisphosphonates. By these approaches, over 250 cancer patients have been treated, seemingly safely, but with only rare incidences of complete remission. One major concern regarding the cells' limited clinical efficacy is their tendency to become irreparably exhausted by chronic antigen exposure. A second major concern is their seeming inefficiency at homing to solid tumors and the tissues harboring those tumors.

Chimeric antigen receptor T cell (CAR-T) therapy is showing promise in the clinic for B cell malignancies. However, with regard to treating solid tumors, the performance of CAR-T cells has to date been below expectations showing less effectiveness at inducing complete tumor responses and high incident rates of off-tumor cytotoxicity. As for peripheral blood γδ T cells, a major obstacle to the success of CAR-T approaches for solid tumors is the likely inefficiency of systemic CAR-T cells to migrate to the sites of malignancy and to reside there in a functionally efficacious state. Additionally, being based on conventional αβ T cells, CAR-T cells have to overcome immunosuppressive signals in the tumor microenvironment, e.g. those transmitted via the PD1 receptor.

There may be advantages associated with using γδ T cells for CAR-T approaches, because they can be transduced with tumor-reactive chimeric antigen specific TCRs, while retaining their innate capabilities of recognizing transformed cells using receptors such as NKG2D. Thus they may simultaneously bring to bear upon tumors adaptive (TCR) and innate (NKG2D)-mediated effects. However, there remains the issue of the seeming inefficiency of human blood γδ T cells at homing to tumors within solid tissues and therein being maintained in an active form. This consideration has provoked a more detailed consideration of γδ T cells that are ordinarily resident in non-haematopoietic tissues.

Such T cells migrate to non-haematopoietic tissues as part of their development and as such are distinct from those T cells, e.g., tissue-resident TCRαβ memory T cells (TRM cells) that infiltrate the tissue after systemic priming. Tissue-resident γδ T cells are most well studied in mice, where they have been shown to be prevalent in skin, gut, and reproductive tissues, among other sites. Many such cells have been shown to harbor innate-like functional potentials whereby they can respond to challenges through activation of the NKG2D receptor. The inventors have recently obtained data demonstrating that human skin and intestine likewise harbor large compartments of non-haematopoietic tissue-resident γδ T cells with innate-like activities. The study of malignancies, inflammation, atopy, allergy, and other pathologies that form within non-haematopoietic tissues has largely failed to consider the potential impact of these innate-like human T cells that reside within the tissues in which pathological lesions occur.

Human γδ T cells resident within non-haematopoietic tissues are much less well studied because their localization renders the cells harder to sample, and because there has been no established means of culturing them. This subtype comprises a diversity of cells with non-MHC-restricted cytolytic potential, which, because they do not express Vδ2-containing TCRs, are wholly unreactive to low molecular weight phospho-moieties. Although few precise TCR-specificities are known for such cells, available data suggest that the cells are reactive to self-antigens, such as Endothelial Protein C Receptor (EPCR), which is over-expressed by cytomegalovirus (CMV)-infected cells and by many solid tumors. Non-haematopoietic tissue-associated γδ T cells also commonly express NKG2D. Given these properties, and the cells' physiologic residence within non-haematopoietic tissues such as the skin and gut, the adoptive transfer of such cells to cancer patients might be considerably more effective at targeting solid tumors and potentially other immunopathologies.

To exploit non-Vδ2 cells for immunotherapy requires either a means to expand the cells in situ or to harvest them and expand them ex vivo prior to re-infusion. The latter approach has been adopted because there are no known TCR-activating agents that have the proven capacity to expand large numbers of non-Vδ2 T cells in situ. To overcome the challenge of limited availability of non-haematopoietic tissues, some researchers have attempted to expand the very small numbers of non-Vδ2 T cells from the blood wherein Vδ2-expressing cells are the dominant subset, making the assumption that these cells are equivalent to tissue-resident non-Vδ2 T cells. The small numbers of non-Vδ2 T cells found in the blood expand substantially during active CMV infection, show superior reactivity toward CMV by comparison to Vδ2 T cells, and seem able to protect the human fetus in cases of CMV infection in utero. Additionally, CMV-reactive non-Vδ2 γδ T cells seemingly protect transplant patients from CMV re-activation during immunosuppression, and via cross reactivity to transformed cells, decrease the risk of secondary malignancies. Similarly, there are data suggesting that γδ T cells play beneficial roles in controlling HIV infection, in which instance non-Vδ2 γδ T cells are expanded in the blood relative to Vδ2 T cells.

Blood resident non-Vδ2 cells have been expanded ex vivo by addition of exogenous agents that either directly activate TCR signaling, e.g., by using an agent such as an anti-CD3 antibody, pan γδ-TCR-specific antibody or phytohemagglutinin (PHA), or by co-culturing stimulated non-Vδ2 T cells with artificial antigen presenting cells (aAPC), wherein direct contact between the γδ T cells and the aAPC is required for non-Vδ2 T cell expansion ex vivo. Alternatively, cells have been expanded by promoting NKG2D receptor signaling by use of immobilized recombinant MICA (an NKG2D ligand), for example as was used to sustain the proliferation of γδ T cell cultures ex vivo from epithelia cancer-infiltrating lymphocytes (TILs). In sum, the current methods of expansion ex vivo of Vδ2-expressing blood γδ T cells or of non-Vδ2 blood γδ T cells require addition of agents, invariably promoting activation of the TCR and/or NKG2D receptors together with supplementary cytokines, such as IL-2. This combination of receptor-activating signals and cytokines reflects the standard approach to culturing and expanding T cells, broadly adopted by the community. To date, no method has been described to substantially expand γδ T cells resident in non-haematopoietic tissue. Such a method is described herein.

As part of a phenotypic and functional characterization of human non-haematopoietic tissue-resident γδ T cells (e.g., skin γδ T cells), the present inventors have isolated a distinct and large population of γδ T cells normally resident within non-haematopoietic tissues and with unique properties relative to αβ T cells and blood-resident γδ T cells. The inventors have found that the cells show strong, TCR-independent, innate-like responses to NKG2D-ligands and to cytokines. Whereas efforts at expansion of primary αβ T cells have commonly employed co-culturing with other supporting cells as a source of beneficial growth factors, the present inventors have shown unexpectedly that the γδ T cells resident in skin and other non-haematopoietic tissues are profoundly and specifically suppressed by co-culturing these cells in contact with autologous dermal fibroblasts and potentially other stromal components, such as keratinocytes and endothelial cells. Relief of such interactions permits the cells to be rapidly expanded in large quantities for potential clinical applications.

Furthermore, in contrast to efforts to date to expand blood- and tumor-derived γδ T cells, the present inventors have shown that such non-haematopoietic tissue-resident γδ T cells can be expanded without deliberate addition of any exogenous agents that activate their TCR or NKG2D signaling pathways.

Disclosed herein is a novel means to effectively and reproducibly isolate and expand γδ T cells from human or non-human animal non-haematopoietic tissue, such as skin and intestine. The expansion is promoted by disrupting the contact of non-haematopoietic tissue-derived non-Vδ2 T cells with autologous fibroblasts and potentially other stromal components, and is sustained by culture with IL-2, IL-15, IL-4, and/or IL-21.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1. Analytical Methods

Unless otherwise stated, the following methods were utilized to generate the results of the subsequent examples.

Flow Cytometry

Flow cytometry was performed using the following antibody-fluorochrome conjugates: Ki-67-BV421, CD3-BVδ10, Vδ1-PeVio770, TIM-3-PE, CD9-PE, CCR3-BV421, and CD39-BV421. Samples were also stained for viability using eFluor770NIR. Commercial antibodies were purchased from Biolegend or Miltenyi. Viability dye (near IR) was from eBioscience. Ki-67 staining was performed on cells fixed and permeabilized using the Foxp3 staining buffer set (eBioscience). Once each experiment was finished, the cell population was washed in PBS and split in half. Cells were stained with eFluor770 NIR for viability and washed, followed by staining with TrueStain (Biolegend) to avoid unspecific binding of staining antibodies. Half of the sample was stained for the indicated surface markers, and the other half was stained for lineage markers only (CD3, Vδ1) and with the equivalent isotype control for the surface markers used. The matched mouse isotype antibody conjugated to the same fluorochrome was used at the same concentration. Isotype controls bind to no known human antigen and therefor indicate unspecific binding or false positives. Histograms are shown in comparison to its corresponding isotype control or, where indicated, FMO (FIGS. 1D, 2A, 3B, 4B, 6B, 7A, and 11-13). Data summaries indicate the percentage of cells that stained positive for the indicated marker compared and thus at a level higher than the isotype. Flow cytometry data analysis was performed on FlowJo (Version 10.1).

RNA Sequencing

Vδ1 T cells from human skin and human blood Vδ1 T cells (after T cell receptor initiated expansion) were sorted (FACS), centrifuged and the cell pellet re-suspended in RLT buffer. RNA was prepared using the RNA-Micro-plus kit (QIAGEN). RNA libraries were generated using the KAPA Stranded RNA-seq Kit with RiboErase (HMR) (KAPA BIOSYSTEMS). Paired-end sequencing on HiSeq 2500 (Illumina) using rapid run chemistry (read length: 100 bp). 101 base-pair paired-end reads were aligned and quantified using RSEM (v.2.11) with Bowtie2. Reads were aligned to the human transcriptome, the count values have been log 2 transformed and quantile normalized.

Cytokine Quantification

Vδ1 T cells from human skin were stimulated with PMA and ionomycin or plate bound anti-CD3 mAb (OKT3, 5 μg/ml) for 24 hours. Supernatants were taken afterwards and analyzed using ProcartaPlex Human Cytokine & Chemokine Panel 1A (34 plex) from eBioscience. Assays were analyzed using a Luminex FlexMap3D (Luminex Corp). Data was analyzed in Microsoft Excel, the mean of 3 donors (run in duplicates) is shown. Error bars indicate standard deviation.

Co-Culture with Fibroblasts

For each separation culture, two petri dishes (100×25 mm, Corning) were scratched at several places using a scalpel. Minced skin pieces were placed on scratches. After 5 to 10 minutes of drying in the air, the skin pieces normally stuck to the dish and 10 mL of Skin-T media was added. Media were changed once a week and primary fibroblasts were harvested following treatment with ACCUTASE® (Life Technologies) after 3 weeks of growth. Fibroblasts were seeded in either 48 well wells at $1 \times 10^4$ or into the bottom chamber of 24 well plates at $2 \times 10^4$ in the case of transwell experiments. After 2 to 3 days, fibroblasts reached confluence and co-culture experiments were started using RPMI and the cytokines indicated adding $2 \times 10^5$ mixed skin lymphocytes in the case of 48 well plates, or $3 \times 10^5$ lymphocytes in the case of 24 well plates, bottom wells as well as transwells.

Expansion of Blood Derived γδ T Cells

Blood derived γδ T cells within PBMCs can only be expanded if stimulated with TCR ligands (in the case of Vδ2, e.g. IPP, HMBPP, bisphosphonates) or antibody supplementation to either cross-link the TCR receptor (mAbs) or the TCR associated kinase CD3. The same effect of TCR cross-linking can also be achieved using, lectins such as PHA. In the absence of addition of such TCR stimulating agents, the γδ T cells in PBMCs survive for several days but fail to expand and remain in their initial composition of T cell subsets with minor variations.

Blood from healthy volunteers was used to isolate PBMCs by layering whole blood onto Ficoll followed by centrifugation at 400 g for 20 minutes to separate red blood cells, blood plasma, and white lymphocytes/monocytes. White blood cells were carefully harvested through a stripett and washed four times in cold PBS. Cells were resuspended in RPMI-1640 medium (Life Technologies) with 10% heat-inactivated foetal bovine serum (Life Technologies), L-glutamine (292 µg/ml; Life Technologies), penicillin (100 units/ml; Life Technologies), streptomycin (100 µg/ml; Life Technologies), N-2-hydroxyethylpiperazine-N-2-ethane sulfonic acid (HEPES; 0.01 M; Life Technologies), sodium pyruvate (1 mM; Life Technologies), minimal essential media (MEM) non-essential amino acids (1×; Life Technologies) at a density of $1\times10^6$ per mL and supplemented with IL-2 (100 IU/ml). Cells were transferred into a 24 well plate that was coated with pan γδ TCR monoclonal antibody (20 µg/ml, clone B1, Biolegend) 90 minutes prior to cell transfer. Cells were grown for 14 days, media changed ever 2-3 days and fresh cytokines added. Upon reaching confluence, cells were split 1:1. Under these conditions, after 14 days, the original minor population of γδ T cells is normally highly activated through their TCR (as indicated by upregulation if CD69 and CD25) and largely enriched consisting of mainly Vδ2 T cells but also Vδ1 T cells (up to 30% of all γδ T cells). Vδ1 T cells can subsequently be isolated using FACS for functional or phenotypic (e.g., genetic) analysis.

Example 2. Isolation of Non-Haematopoietic Tissue-Resident γδ T Cells from Skin and Gut A three-dimensional skin explant protocol was established using the Clark protocol. Cellfoam Matrices (Cytomatrix Pty Ltd, Victoria, Australia) or equivalent having dimensions of 9 mm×9 mm×1.5 mm, were autoclaved and incubated in a solution of 100 mg/ml rat tail collagen I (BD Biosciences) in PBS for 30 minutes at room temperature, followed by one rinse in PBS. Samples of adult human skin were obtained within 3-6 hours of cutaneous surgery. Subcutaneous fat was removed and the remaining skin tissue was minced into fragments measuring approximately 1 mm×1 mm. Approximately five skin fragments/explants were placed and pressed down onto the surface of each matrix. Each matrix was placed into a separate well of a 24-well plate (Corning) containing 2 ml of Skin-T media (Iscove's Modified Dulbecco's Medium (IMDM; Life Technologies) with 10% heat-inactivated fetal bovine serum (Life Technologies), L-glutamine (292 µg/ml; Life Technologies), penicillin (100 units/ml; Life Technologies), streptomycin (100 µg/ml; Life Technologies), N-2-hydroxyethylpiperazine-N-2-ethane sulfonic acid (HEPES; 0.01 M; Life Technologies), sodium pyruvate (1 mM; Life Technologies), minimal essential media (MEM) non-essential amino acids (1×; Life Technologies) and 3.5 µl/L 2-mercaptoethanol (Life Technologies). For the first 7 days of culture Amphotericin (2.5 µg/ml; Life Technologies) was added to the media. Media were refreshed three times per week by aspirating the upper 1 mL of media from each well and adding 1 ml of fresh medium. Human recombinant IL-2 (100 IU/mL; PROLEUKIN®; Novartis Pharmaceutical UK Ltd) and human recombinant IL-15 (20 ng/ml; Biolegend) were added at the initiation of culture and on each media refresh until the isolation of lymphocytes after 21-35 days, as indicated in Table 1. Up to 96 wells (four 24-well plates) were set up in culture for each donor.

To isolate the lymphocytes, the matrices and media were transferred to a 50 ml centrifuge tube (Corning) containing 10 ml Hanks Balanced Salt Solution (HBSS; Life Technologies) with 0.01 mM HEPES (up to 12 matrices/tube). The matrices were rinsed with the cell suspension using a 10 ml pipette, and the cell suspension was passed through a 70 µm filter (BD Biosciences) into a fresh 50 ml centrifuge tube. The rinsing of the matrices was repeated two additional times. The media from the culture well was also aspirated and passed through a 70 µm filter into a fresh 50 ml centrifuge tube. The wells were washed two further times with 1 ml of 0.01 mM HEPES/HBSS and passed through a 70 µm filter. Cells were subsequently isolated by centrifugation (1600 rpm for 15 minutes). The pellet was re-suspended in Skin-T media. The final cell pellet was re-suspended in Skin-T media for subsequent flow cytometry analysis or functional studies. When cell counts were required, lymphocytes were counted at this stage by either; (1) trypan blue stain (0.4%) (Life Technologies) and haemocytometer, or (2) CASY® Model TT cell counter and analyzer (Roche). Results from an exemplary study are shown in Table 1, below.

TABLE 1

Isolated lymphocyte yields per donor.

| Duration of culture | Total Lymphocytes | Number of Scaffolds | Lymphocytes/ Scaffold |
|---|---|---|---|
| 35 days | $23.5 \times 10^6$ | 72 | $3.26 \times 10^5$ |
| 32 days | $38.87 \times 10^6$ | 96 | $4.04 \times 10^5$ |
| 21 days | $29.9 \times 10^6$ | 96 | $3.11 \times 10^5$ |
| 21 days | $18.0 \times 10^6$ | 72 | $2.50 \times 10^5$ |
| 23 days | $16.0 \times 10^6$ | 72 | $2.22 \times 10^5$ |
| 28 days | $10.7 \times 10^6$ | 23 | $4.65 \times 10^5$ |
| 25 days | $88.0 \times 10^6$ | 120 | $7.33 \times 10^5$ |
| 22 days | $20.0 \times 10^6$ | 39 | $5.12 \times 10^5$ |
| 21 days | $4.1 \times 10^6$ | 42 | $0.97 \times 10^5$ |
| 23 days | $31.4 \times 10^6$ | 96 | $3.27 \times 10^5$ |
| 23 days | $15.21 \times 10^6$ | 72 | $2.11 \times 10^5$ |
| 26 days | $43.0 \times 10^6$ | 144 | $2.99 \times 10^5$ |
| 32 days | $44.5 \times 10^6$ | 96 | $4.64 \times 10^5$ |
| 24 days | $72.4 \times 10^6$ | 96 | $7.54 \times 10^5$ |
| 22 days | $46.0 \times 10^6$ | 96 | $4.79 \times 10^5$ |
| Averages: | | | |
| 25 days | $33.4 \times 10^6$ | 82 | $3.91 \times 10^5$ |

Because primary gut samples were more prone to contamination, acquired biopsies were first washed in IMDM containing 10% FCS, penicillin (500 U/mL), streptomycin (500 µg/mL), gentamicin (100 µg/mL), Amphotericin B (12.5 µg/mL), and Metronidazole (5 µg/mL) twice before minced and placed on scaffolds. Gut scaffold cultures were grown in Gut-T Media (IMDM, 10% FCS, penicillin 100 U/mL, streptomycin 100 µg/mL, gentamicin 20 µg/mL, Metronidazole 1 µg/mL). For the first week of growth we also used Amphotericin B 2.5 µg/mL, similar to the skin. The media contained IL-2 (100 IU/ml) and IL-15 (20 ng/ml) and was changed three times per week. Because the gut structure was more loose than skin, lymphocytes were harvested after one week.

Example 3. Characterization of
Non-Haematopoietic Tissue-Resident γδ T Cells

Figure 1C:
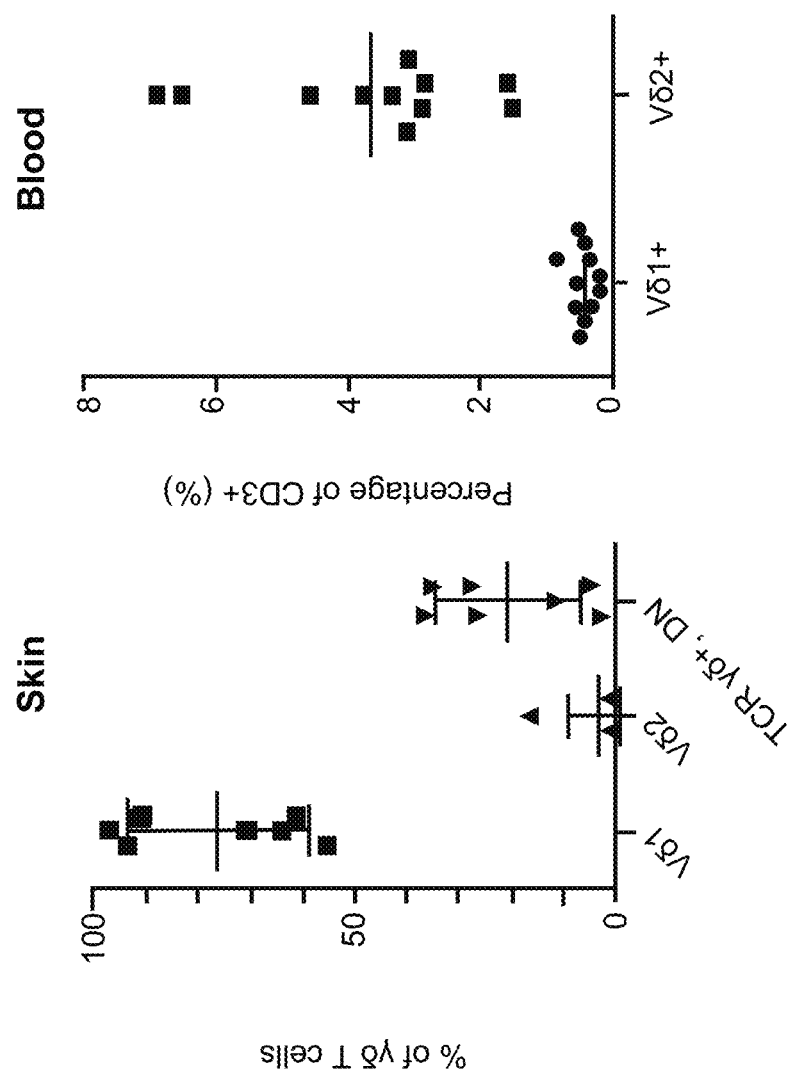
Figure 3A:
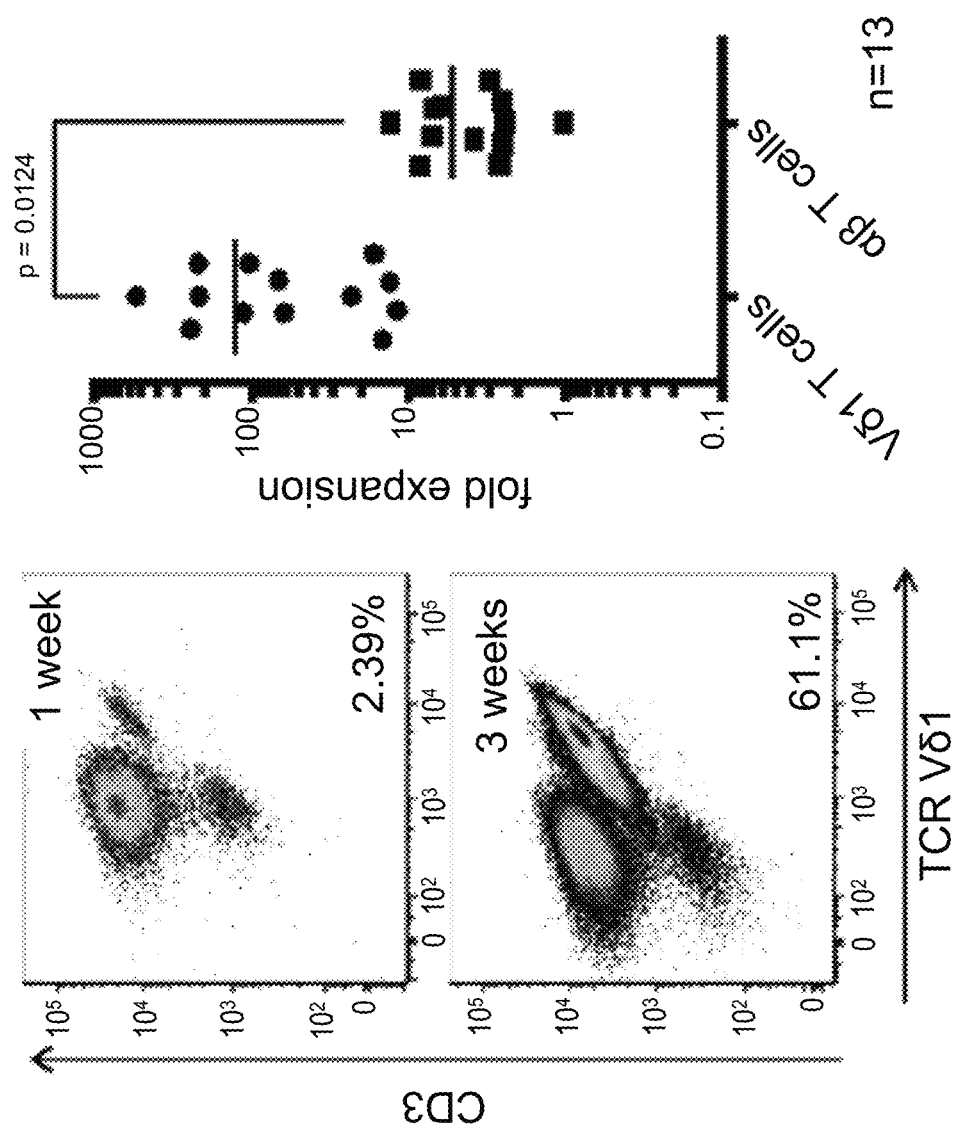
FIGS. 3A-3D show that skin-resident γδ T cells exclusively respond to segregation from the dermal stroma with strong activation and proliferation.
Figure 3B:
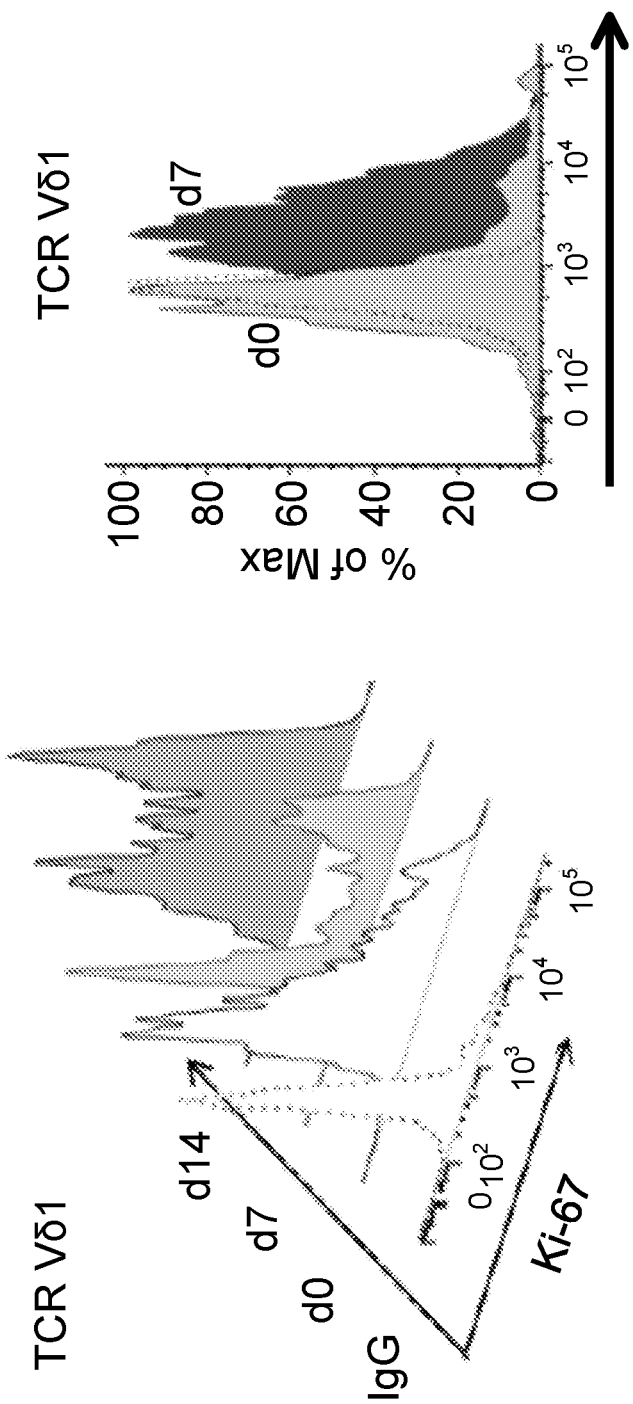
Figure 3C:
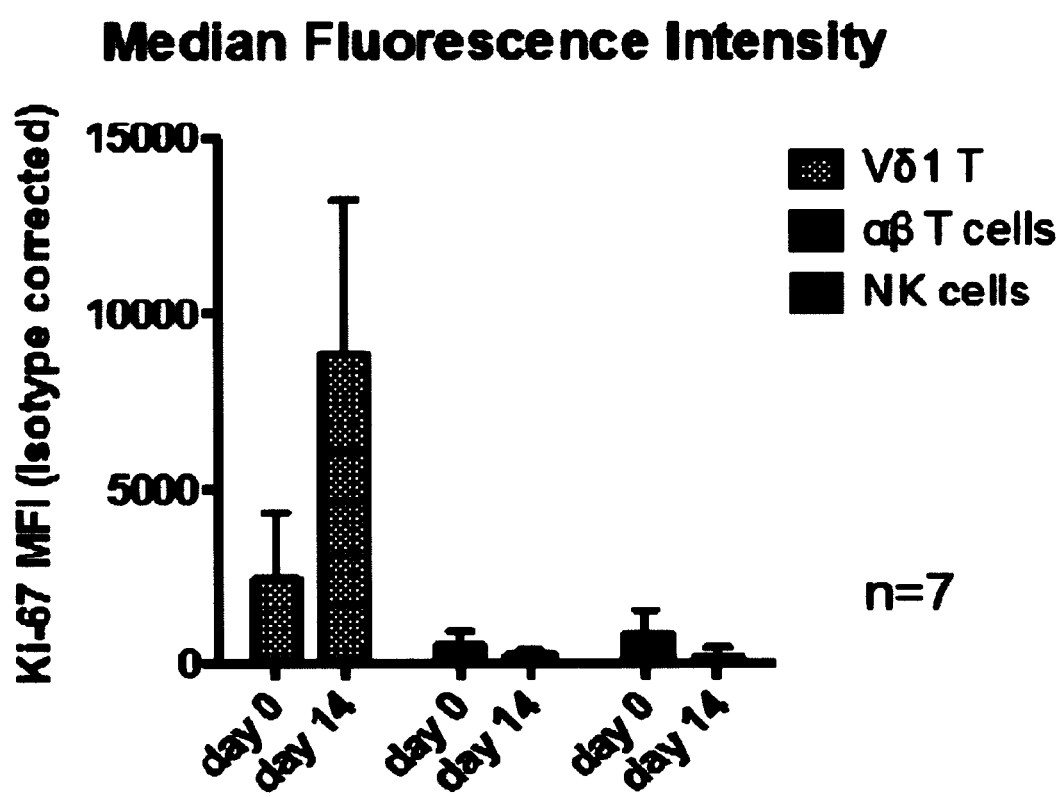
Figure 3D:
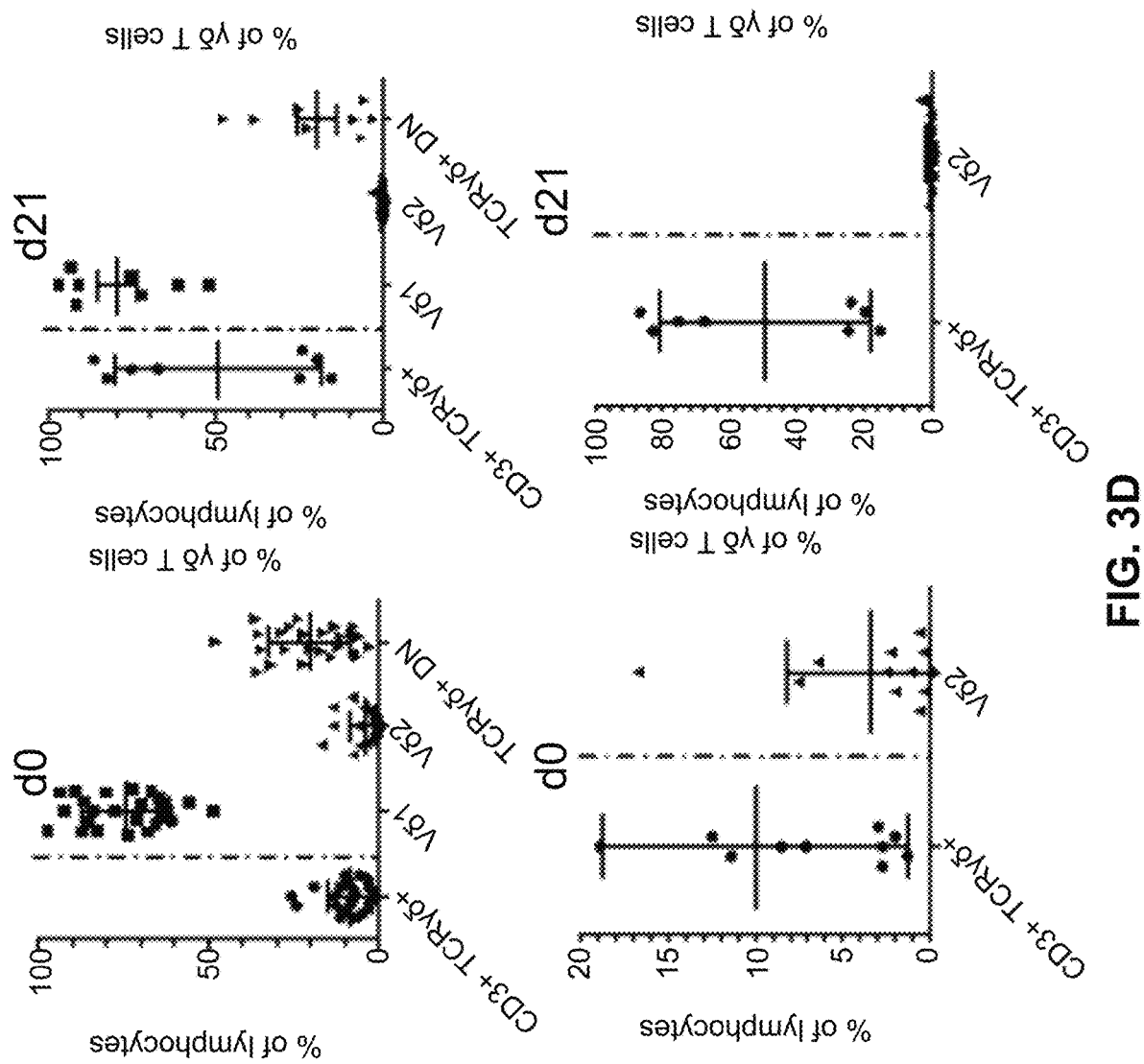

Human γδ T Cells are Abundant in the Skin, Predominantly Vδ2−, and Participate in the Human Lymphoid Stress Surveillance Response FIGS. 1A-1D show that the human skin comprises a notable population of resident γδ T cells. Using the Clark protocol, we used human residual skin samples supplemented with IL-2 and IL-15 to enable the outgrowth of tissue resident lymphocytes over the course of three weeks. The average yield was 240,000 lymphocytes per scaffold. Consistent with previous reports, distinct skin-resident lymphocyte subsets were identified, and the majority of cells expressed a conventional αβ TCR, mostly of the tissue resident "TRM" type. Overall, 59.9% (±8.6%) of CD45+ cells were CD4+, and 18.3% (±2.8%) CD8+ αβ T cells with an NK cell fraction of 8.7% (±3.6%). Additionally, we found a substantial population of γδ T cells (mean 8.513% of CD45+ cells, ±6.564%) in our donors (FIGS. 1A and 3D). This lymphocyte profile was highly reproducible in approximately 100 donors after organotypic culture, and was comparable with freshly digested skin samples, differing only in a slightly increased γδ population, but of practical utility, offering much larger and purer lymphocyte populations compared to standard tissue digestion protocols. In accordance with the literature regarding tissue compartmentalization of human γδ T cells based on their TCR delta chain, most human skin γδ T cells expressed a Vδ1 TCR chain paired with various γ chains identified by flow cytometry. This stands in contrast to the majority of peripheral blood γδ T cells, which show a single specific TCR heterodimer of a Vδ2 chain linked to Vγ9 and were virtually absent in human skin samples. However, it is important to note that a subset expressed neither Vδ1 TCR nor Vδ2 TCR, which are referred to herein as double negative γδ T cells (DN γδ T cells; FIG. 1C).

Figure 1D:
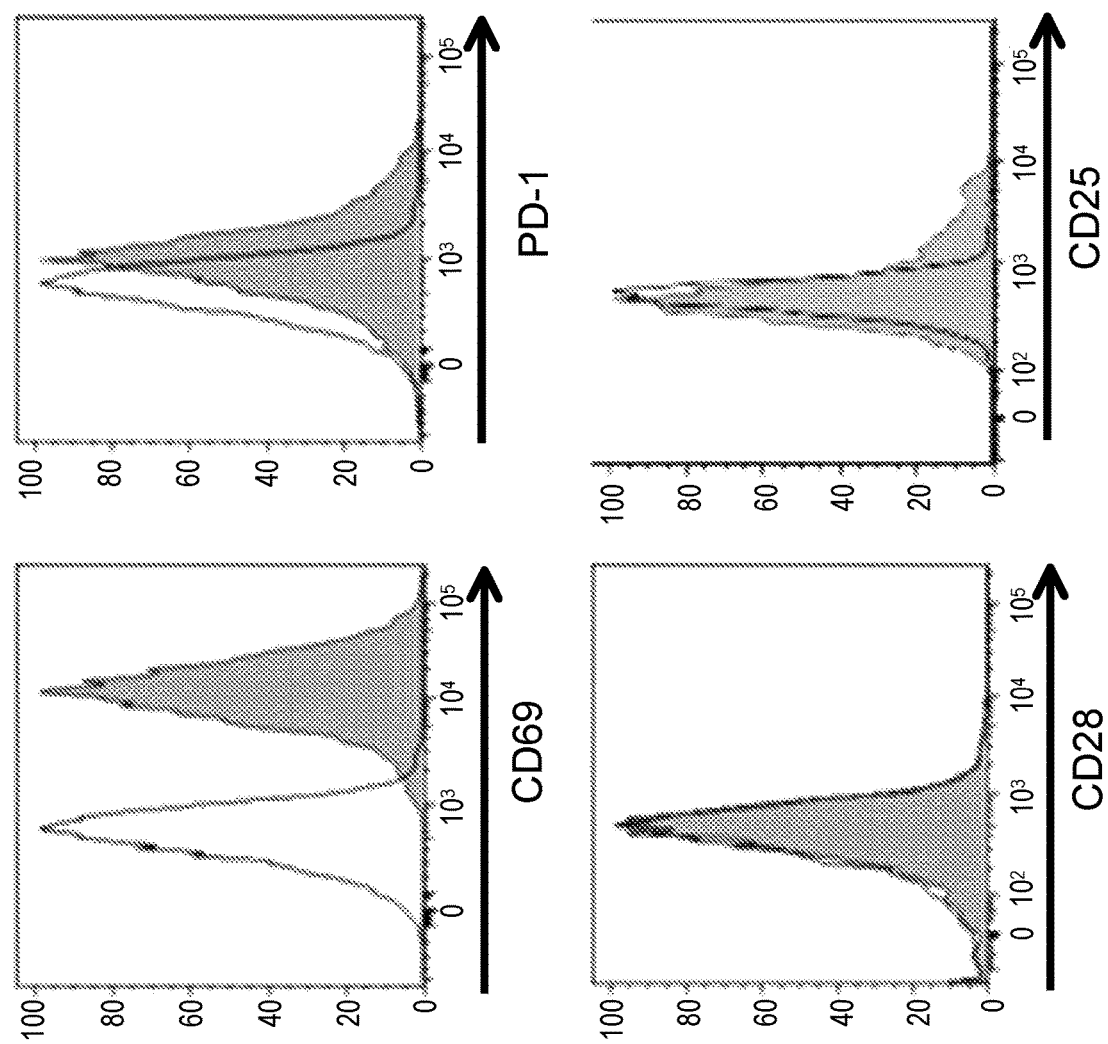
Figure 2A:
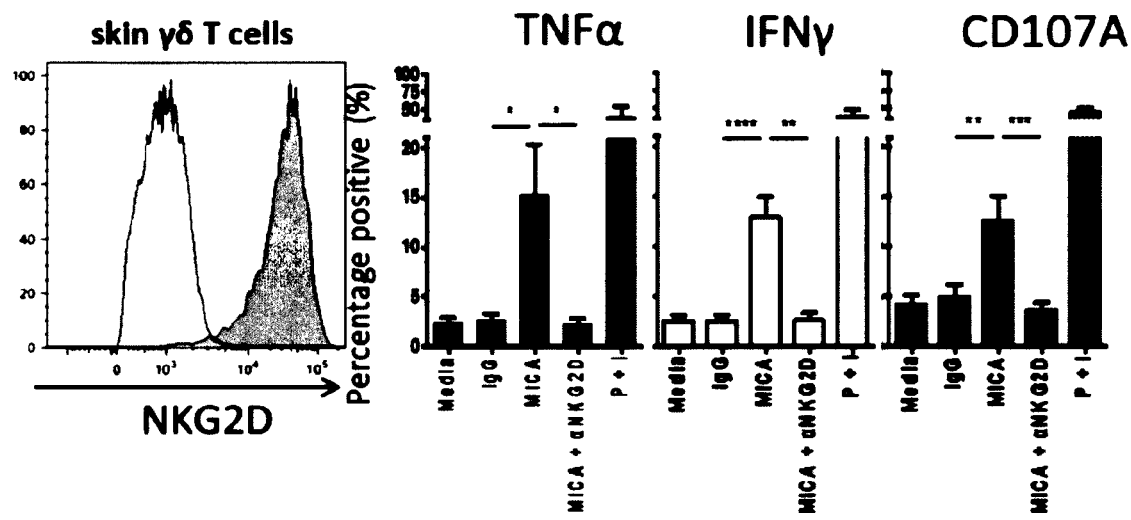
FIGS. 2A to 2D show that skin-resident γδ T cells derived directly from human skin via the Clark protocol display a Th1-biased response upon activation by conventional means for activating T cells and likewise display a Th1-biased response upon activation by NKG2D ligands alone.

Skin-resident γδ T cells grown in this fashion showed a non-terminally differentiated memory phenotype lacking expression of CD45RA and expressing variable levels of the co-stimulatory molecule CCR7. Relative to conventional systemic T cells, skin-resident γδ T cells exhibited high expression of the surface marker CD69 together with the expression of programmed death receptor 1 (PD-1), low to absent levels of IL-2 receptor α (CD25), and a lack of the co-stimulatory molecule CD28, suggesting previous or chronic activation (FIG. 1D). Consistent with their tissue localization, Vδ1 and DN cells show expression of skin and tissue homing markers, such as CCR4, CCR8 and integrin αE (CD103; FIG. 7). This tissue-homing marker-set might prove beneficial in an immunotherapy setting. Additionally, skin-resident γδ T cells show high levels of expression for the activatory receptor NKG2D (FIG. 2A), implying a possible role of these cells in the lymphoid stress surveillance response. NKG2D ligands, such as MICA, MICB, and ULBPs, respectively, are up-regulated by cells in response to DNA damage, EGF-receptor activation, and oxidative stress and may therefore allow T cells expressing NKG2D to identify and eradicate stressed or transformed cells, thereby maintaining tissue homeostasis. In line with this principle, we found that skin-resident γδ T cells expanded by the method of the invention are activated upon exposure to recombinant ligands for the NKG2D receptor (MICA, ULBP2), demonstrating degranulation as measured by the up-regulation of the lysosomal-associated membrane protein CD107a (FIG. 2A). This innate-like feature was exclusive to Vδ1+ and DN γδ T cells, as other tissue-resident T cells (FIG. 2C) and systemic γδ T cells lacked this response (FIG. 10B).

Figure 2B:
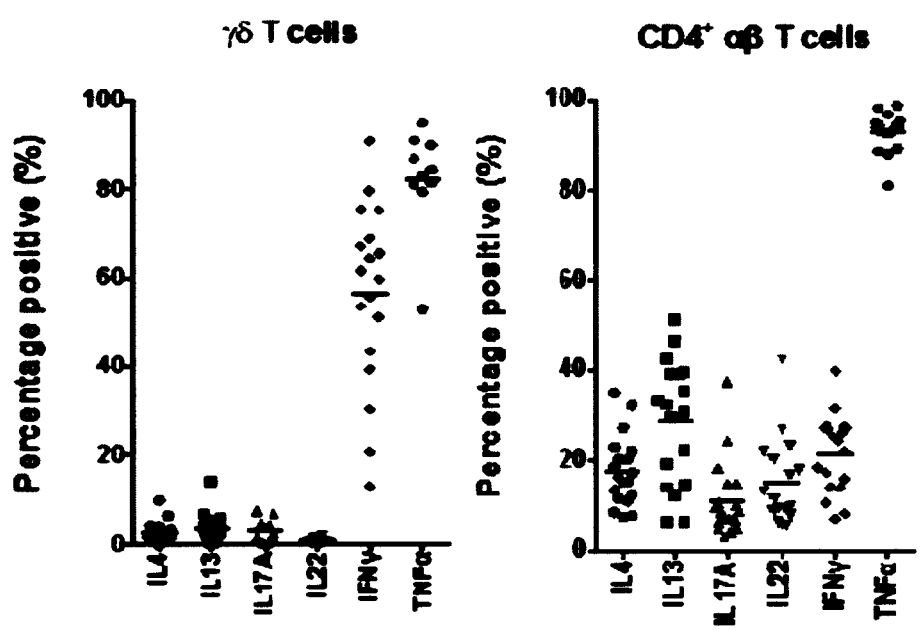
Figure 2C:
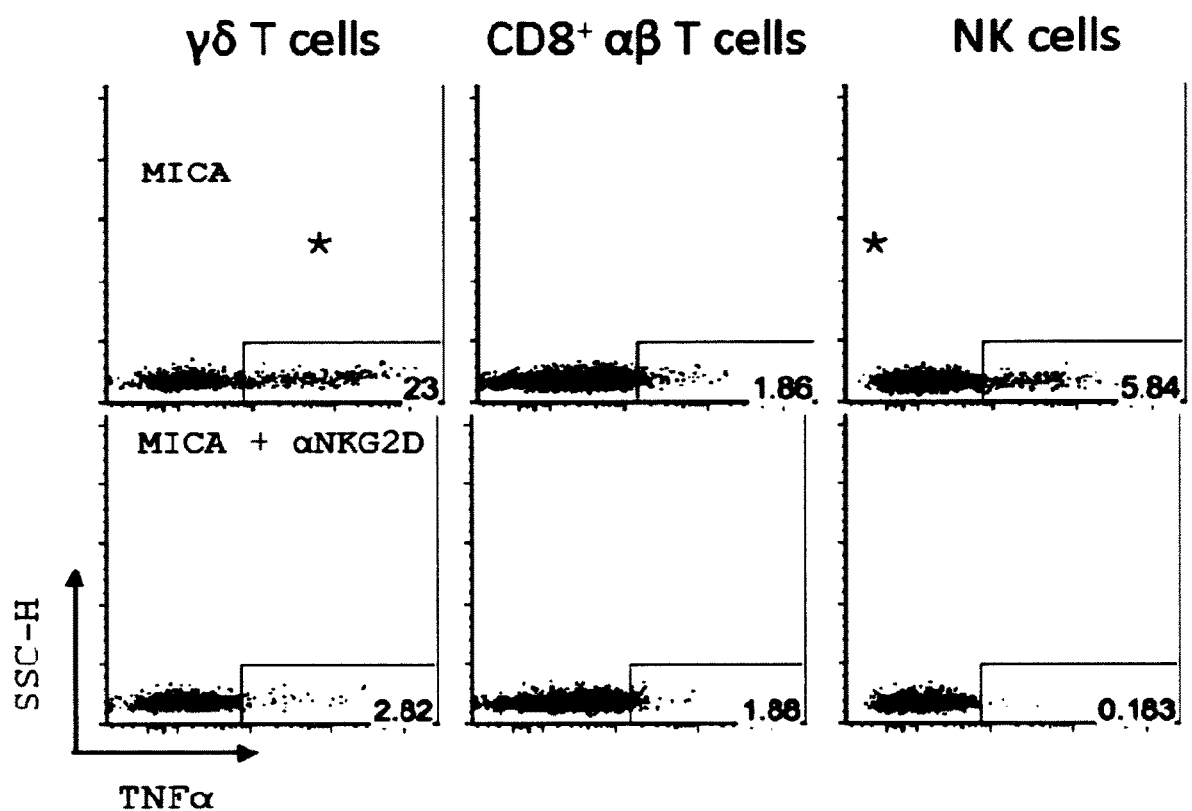
Figure 2D:
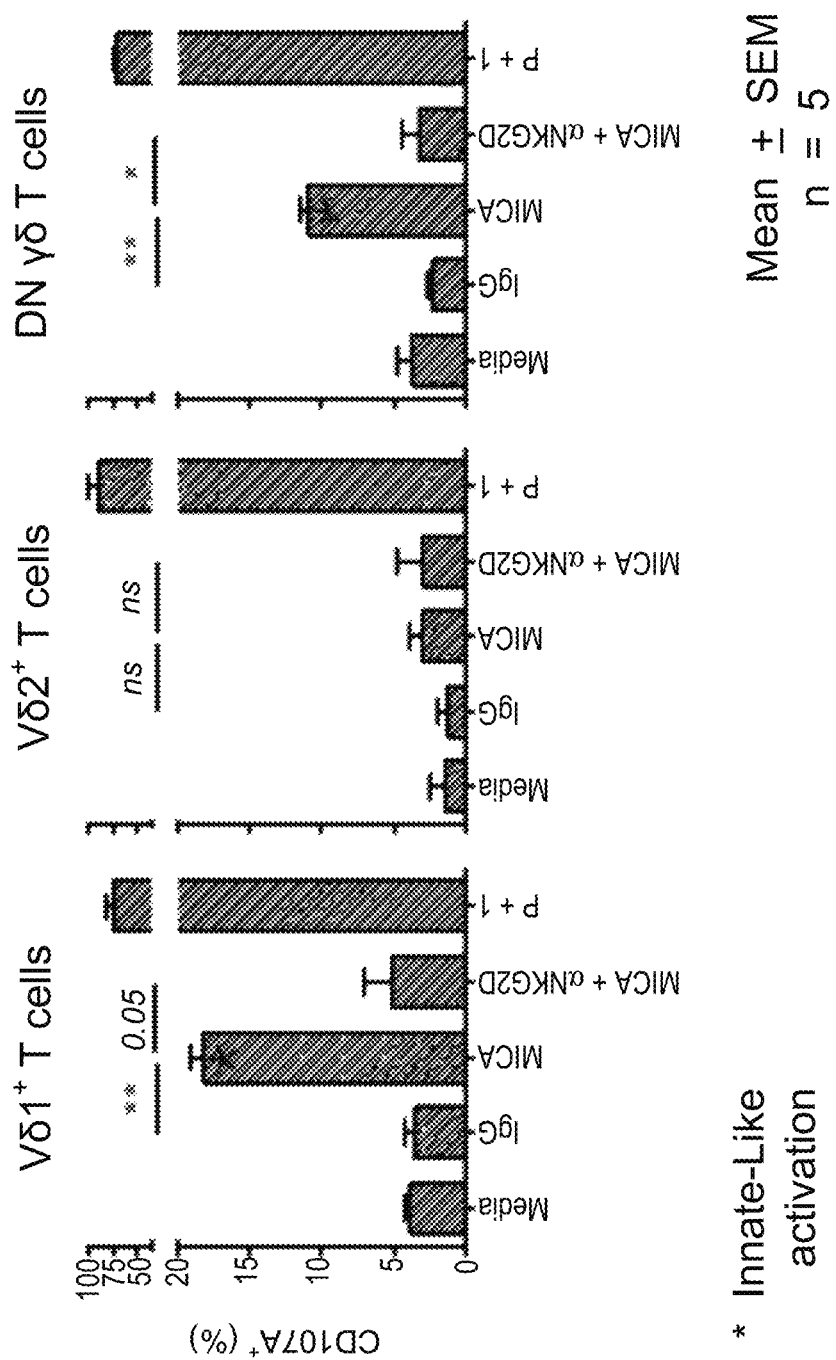
Figure 8:
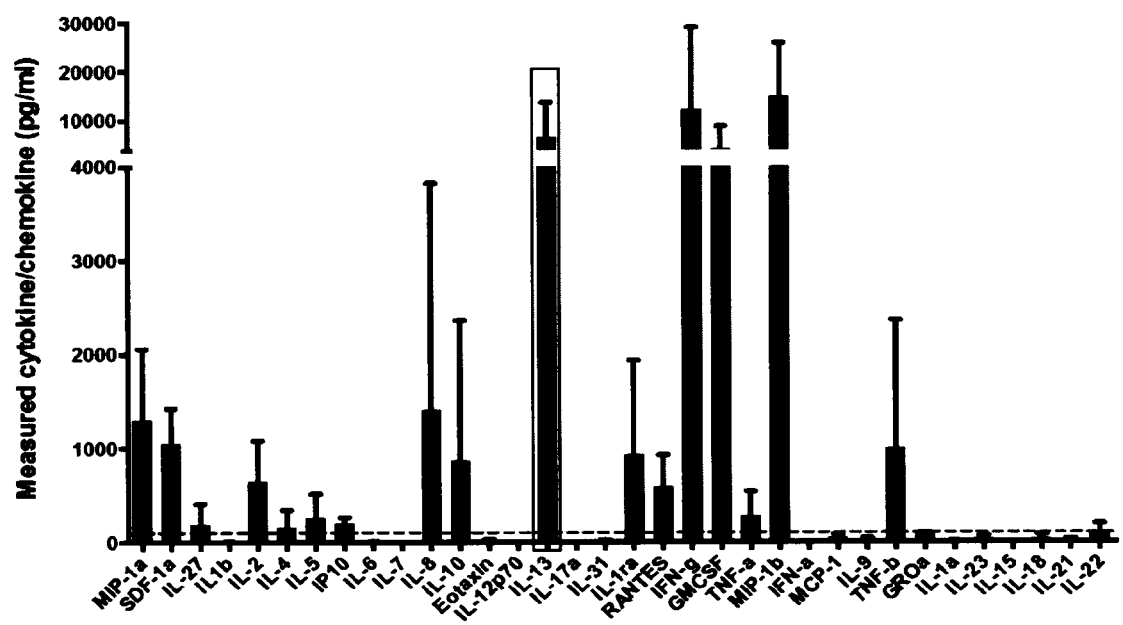
FIG. 8 shows that de-repression of skin-derived γδ T cells, without any stimulation of the TCR, results in spontaneous Th1 cytokine production and interestingly and in contrast with fresh, TCR activated γδ T cells, in the production of the atopic cytokine IL-13. Consistently with freshly derived γδ T cells, de repressed and expanding γδ T cells produce negligible amounts of Th-2-associated cytokines, e.g. IL-4 and IL-5. Skin-derived γδ T cells were allowed to expand for 14 days and sorted negatively by excluding conventional αβ T cells. 150,000 mixed γδ T cells were cultured at a density of 1 million cells/mL in a 96 plate flat well in duplicates for 4 donors without any stimulation or cytokine supplementation. Supernatants were collected after 24 h and analyzed using the LUMINEX®-based cytokine array by Affymetrix.

Overall, activated skin-resident Vδ1+ and DN γδ T cells executed a pro-inflammatory Th1 biased cytokine program (staining positive for IFN-γ, TNF-α and GM-CSF) when activated by either PMA/ionomycin or by NKG2D ligands, e.g. recombinant MICA protein (FIGS. 2A and 2B), thereby asserting the cells' innate-like responses. Indeed, the responses to MICA were almost completely abrogated by blocking the NKG2D receptor by means of an antibody (FIGS. 2B and 2C).

γδ T cells are known to secrete IL-17 under certain disease settings such as psoriasis and within some types of tumors. γδ T cells expanded by the method of the invention produce low levels or no IL-17, even upon extensive activation (FIGS. 2B and 8). Conversely, tissue-resident CD4-expressing αβ T cells did produce IL-17 upon TCR activation (FIG. 2B). In general, αβ T cells showed a much more diverse cytokine repertoire in response to PMA/ionomycin compared to Vδ1+ and DN γδ T cells, which were limited to a Th1 biased program associated with host-protection.

Figure 4A:
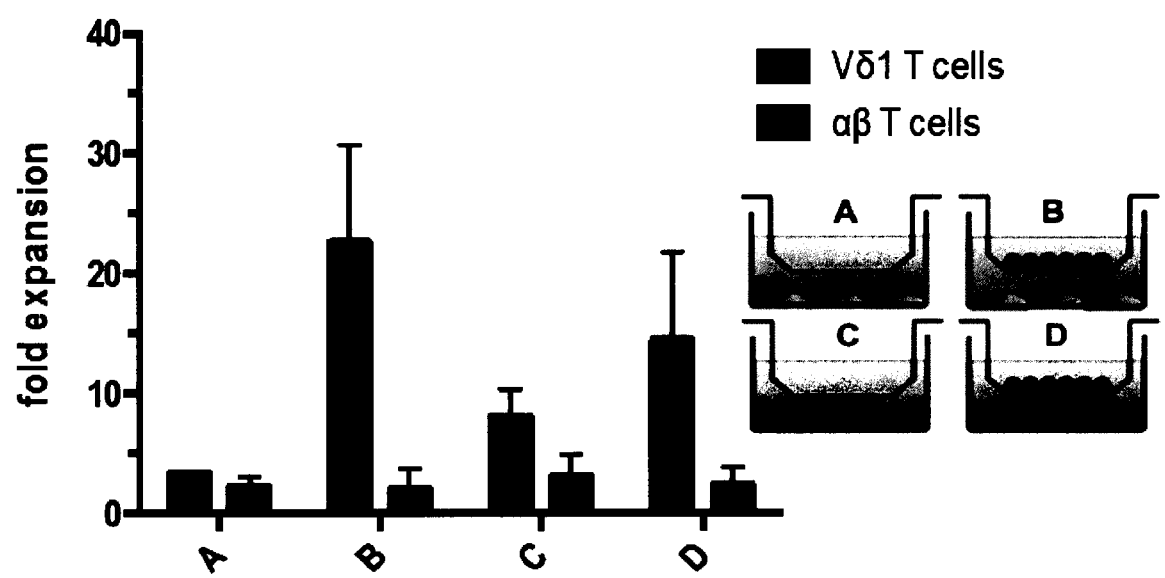
FIGS. 4A and 4B show that skin-resident γδ T cells respond to loss of tissue and are kept in check via a contact-dependent mechanism by dermal stroma cells, particularly fibroblasts.
Figure 4B:
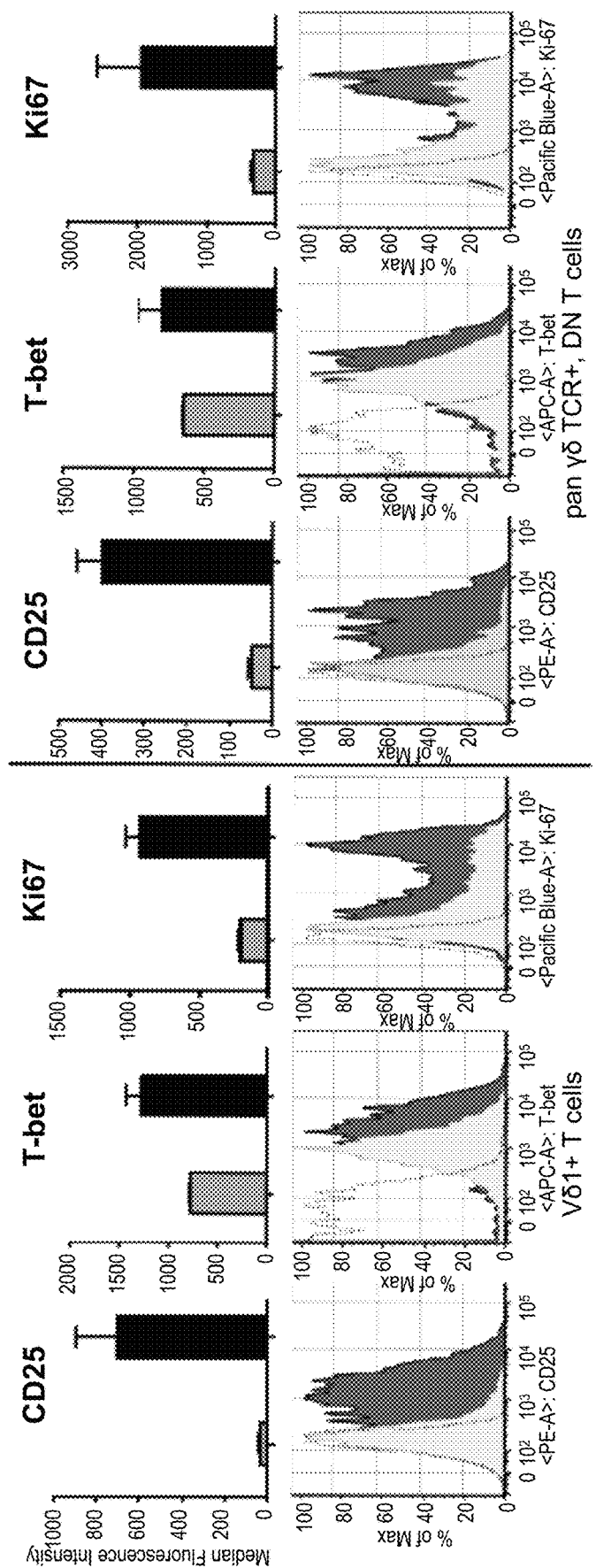

Separation from Tissue Causes Activation and Massive Proliferation of Human Tissue γδ T Cells To further study human tissue γδ T cells, mixed skin lymphocytes were transferred into cell culture wells and supplemented with IL-2 in order to maintain viability over time. Interestingly, by separation from stromal and epithelial cells present in the organotypic culture, Vδ1 T cells uniquely showed signs of activation and proliferation without any additional stimulus. Within 7 days, Vδ1+ and DN γδ T cells uniquely and massively up regulated the nuclear factor Ki-67 and increased surface expression of IL-2 receptor α (CD25; FIGS. 3B and 4B). Strikingly, over the course of three weeks, and solely in the presence of IL-2, tissue-derived Vδ1+ and DN γδ T cells outgrew all other T cell subsets, so as to represent up to 65% of all skin lymphocytes, increasing in number in average 127.18 fold, whilst αβ T cells only multiplied 5.21 times (p=0.0124) as measured by absolute cell numbers (FIG. 3A). MFI of the cell cycling-associated nuclear factor KI-67 increased from 2,664.5 (±1,876.1) to 8,457.7 (±4,574.2) in 14 days in Vδ1+ and DN γδ T cells, whereas in αβ T cells the MFI decreased from 592.8 (±390.5) to 284.7 (±140.1) over the same time course (FIG. 3C). This phenomenon of selective, skin-resident γδ T cell outgrowth could be further supported using additional recombinant IL-15, which increased the viability and total number of lymphocytes.

Skin γδ T Cells are Actively Suppressed by Fibroblasts in a Contact Dependent Manner The striking expansion of Vδ1+ and DN γδ T cells described supra never occurred in organotypic culture systems in which there was extensive fibroblast outgrowth. Autologous fibroblasts were grown out in order to test directly whether their co-culture with Vδ1+ and DN γδ T cells would inhibit the T cell expansion. After a three-week scaffold culture, mixed skin lymphocytes were seeded into wells that were either empty or that contained a previously-established confluent monolayer of fibroblasts, and in each case supplemented the medium with exogenous IL-2 to sustain T cell growth. Additionally, transwells were used to prevent the T cells from directly contacting the fibroblasts within the same wells, while permitting them to be influenced by soluble factors secreted by the fibroblasts. In 14 days of co-culture, Vδ1+ and DN γδ T cells started proliferating in wells in which there were no fibroblasts and in those in which the T cells were prevented from directly contacting the fibroblasts. As before, αβ T cell proliferation was low under all conditions. When T cells were permitted direct contact with fibroblasts, the growth rate over two weeks of Vδ1⁺ and DN γδ T cells was considerably reduced, from 22.6 (±8.07) fold in wells without fibroblast contact to 3.3 (±0.17) fold (FIG. 4A). This contact-mediated inhibition was further confirmed by the absence of up-regulation of CD25, Ki-67, and the transcription factor T-bet in Vδ1 T cells over the course of 7 days, as compared to the lymphocytes grown alone (FIG. 4B). Some form of tissue-mediated control of the immune system would appear to be fundamental to maintaining tissue homeostasis, since without this there would be the potential for persistent inflammation. The suppressive regulation of Vδ1⁺ and DN γδ T cells by stromal fibroblasts would seem to be an example of such control.

In sum, the phenotype of skin-resident Vδ1⁺ and DN γδ T cells and their striking functional potentials are reflective of pre-activated T cells that are ordinarily kept in check by their neighboring dermal fibroblasts via a contact-dependent mechanism. Inactivating that mechanism by releasing the T cells from contact with the fibroblasts selectively permits expansion of Vδ1⁺ and DN γδ T cells, whereas other T cells in the skin are unaffected.

Figure 5A:
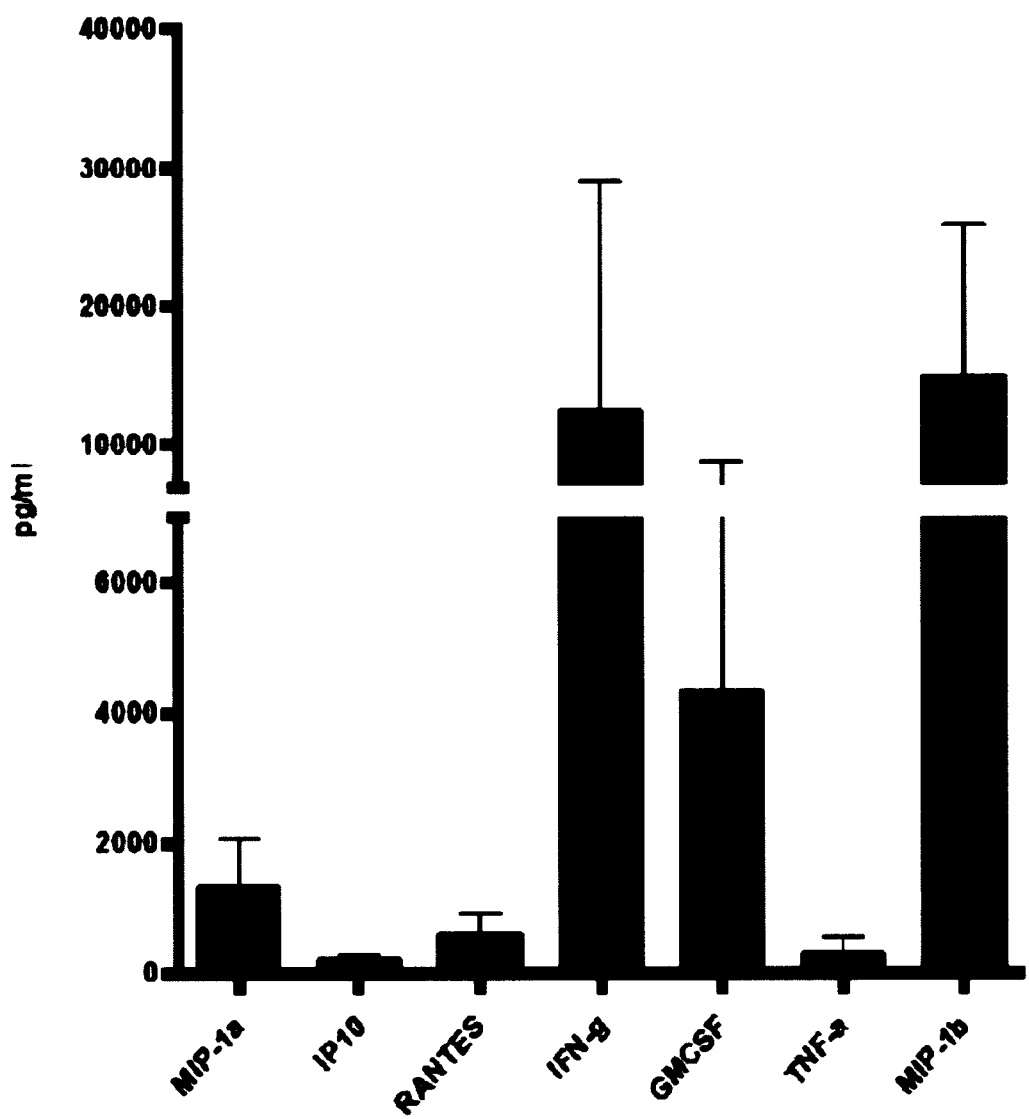
FIGS. 5A and 5B show that expanding skin γδ T cells display signs of de-repression and gain of strong cytotoxic potential.

Release of Contact Mediated Inhibition Prompts a Cytotoxic TH1 Biased Cytokine Response by Skin Vδ1 T Cells Mixed skin-derived lymphocytes were expanded for 14 days, and fluorescence associated cell sorting was used to remove αβ T cells from γδ T cells, enabling purities of up to 90%. Those highly enriched cells were deposited into cell culture wells at concentrations of 150,000 cells/well in RPMI medium containing 10% FCS. Supernatants were collected 24 hours later and assessed for a wide range of effector cytokines using a LUMINEX®-based array. Wholly unexpectedly, expanding γδ T cells (provoked only by their separation from fibroblasts) spontaneously produced large amounts of TH1 associated cytokines such as IFN-γ (12,383.46±16,618.90 µg/ml), GM-CSF (4,316.73±4,534.96 µg/ml) and the proinflammatory chemokines CCL4 (14,877.34±10,935.64 µg/ml) and CCL3 (1,303.07±757.23 µg/ml; FIG. 5A).

Figure 5B:
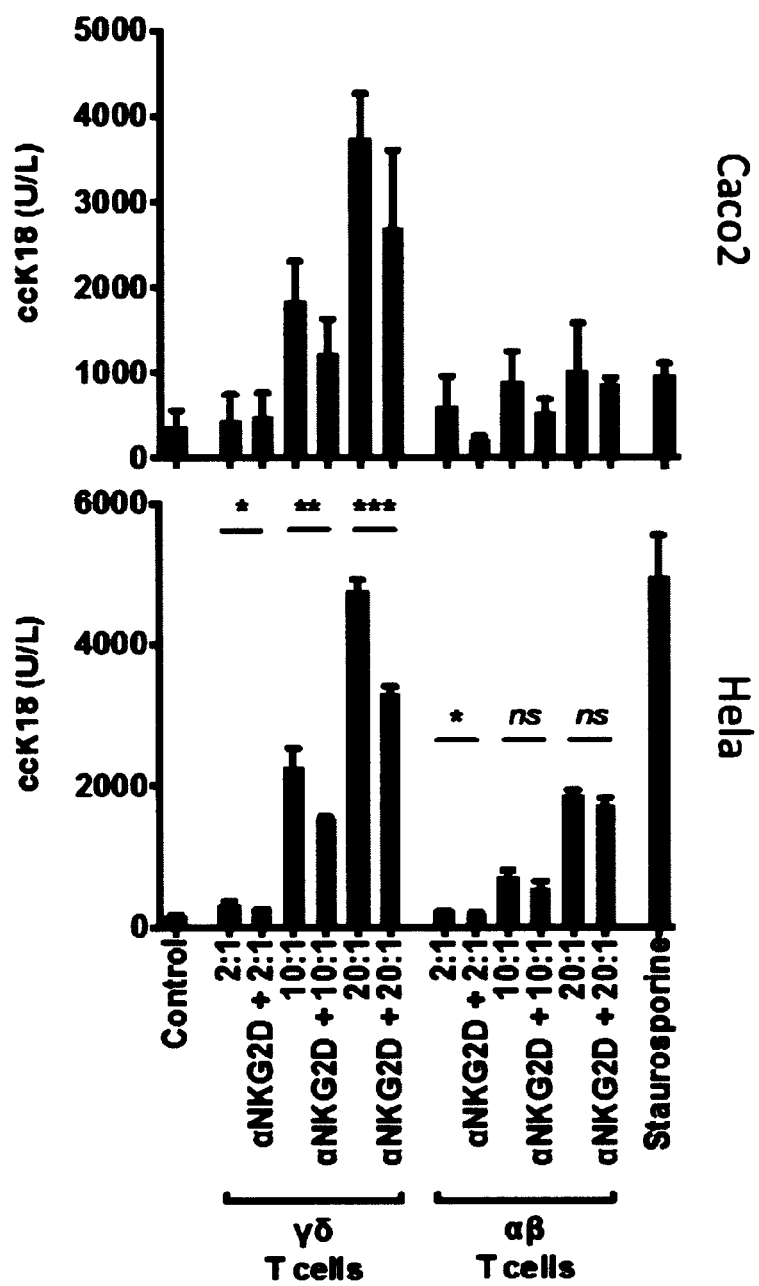
Figure 6A:
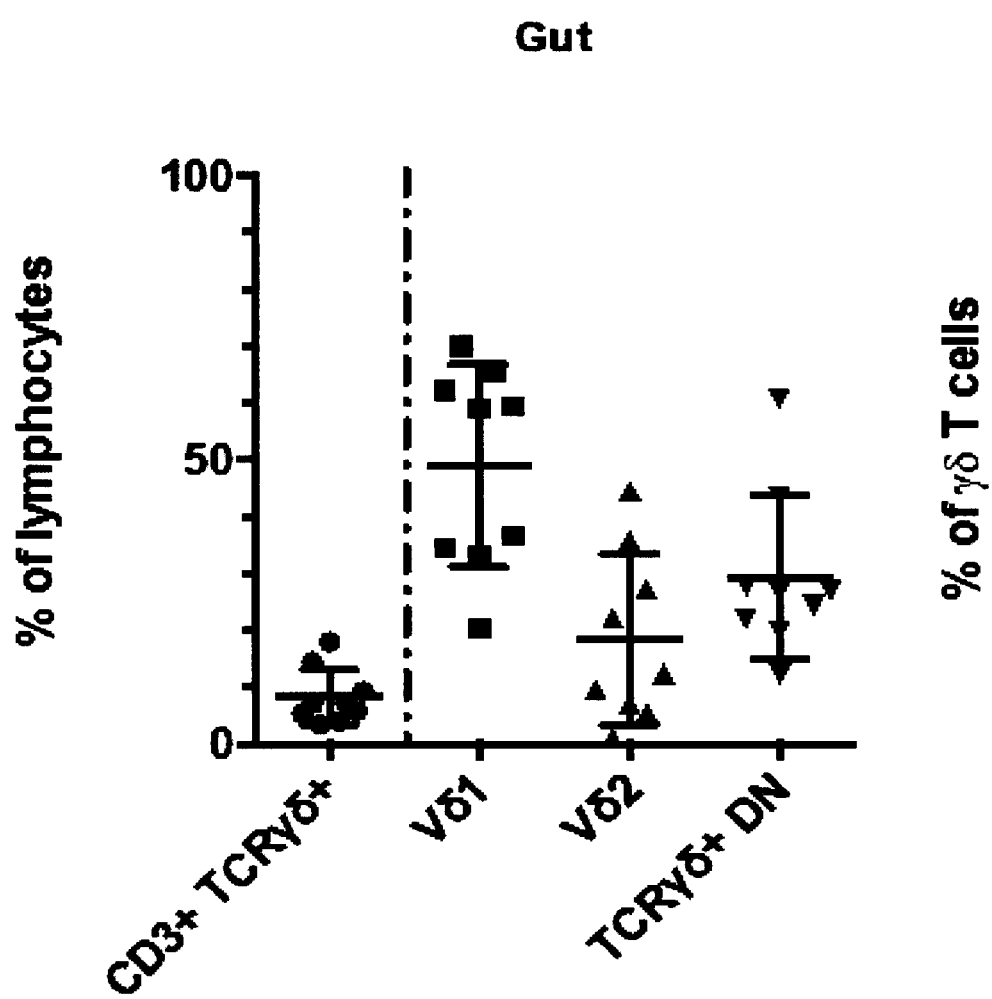
FIGS. 6A-6D show an analysis of tissue-resident γδ T cells in human gut.
Figure 6B:
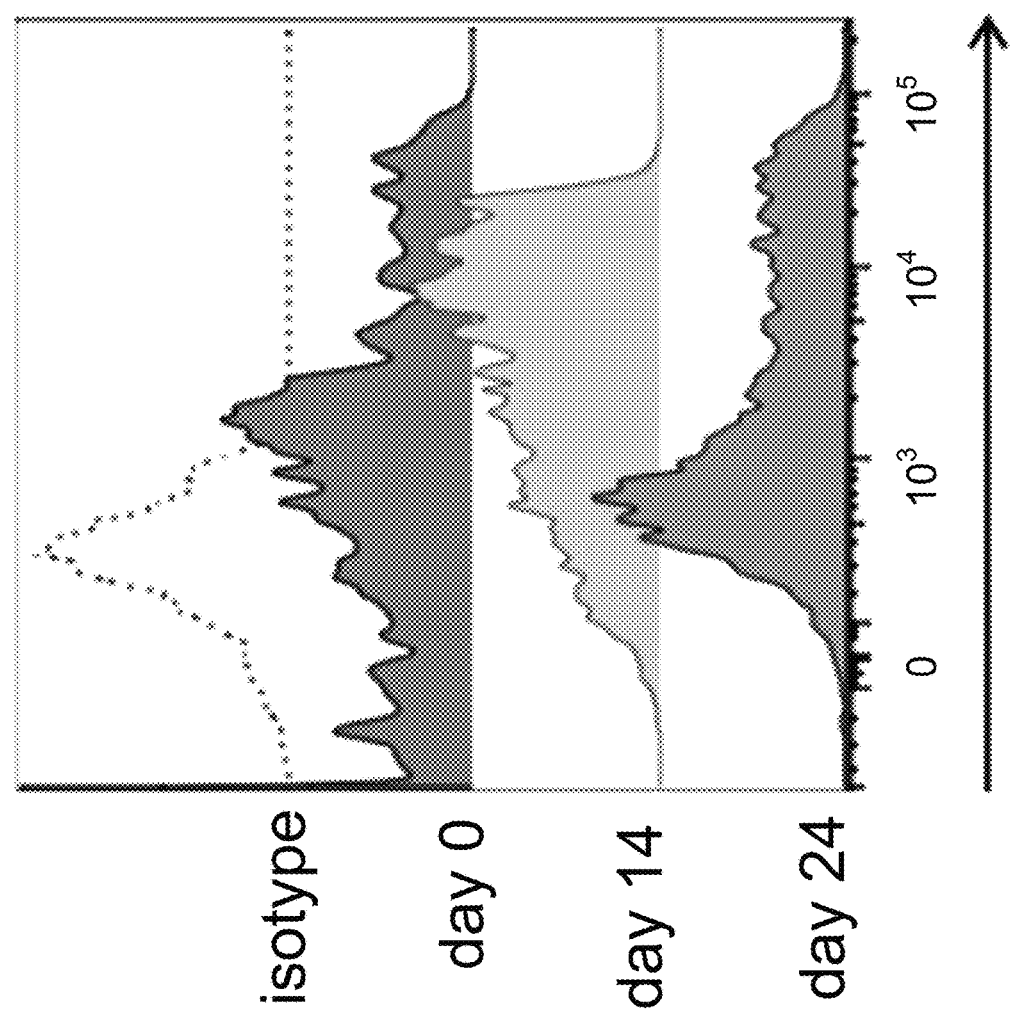
Figure 6C:
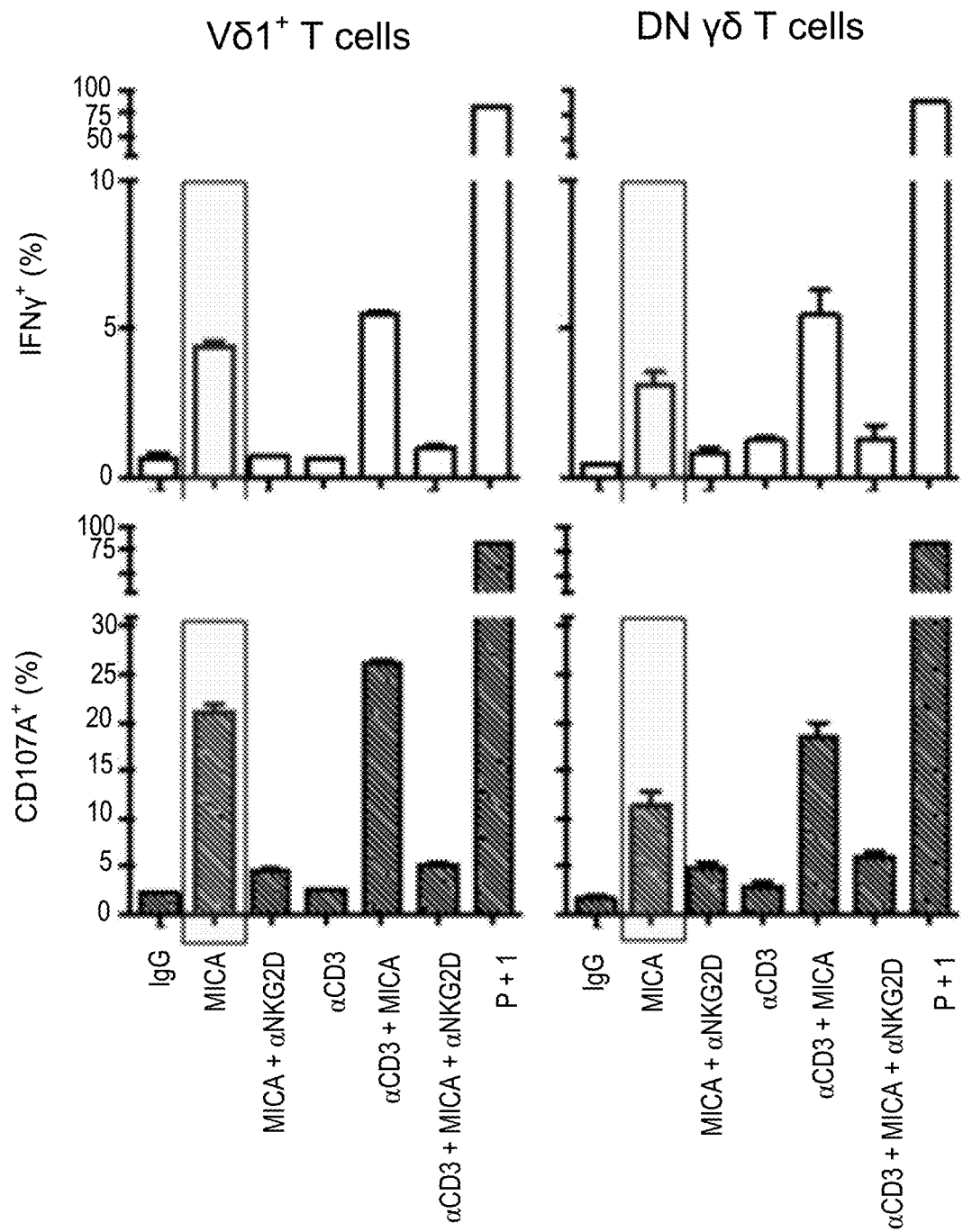
Figure 6D:
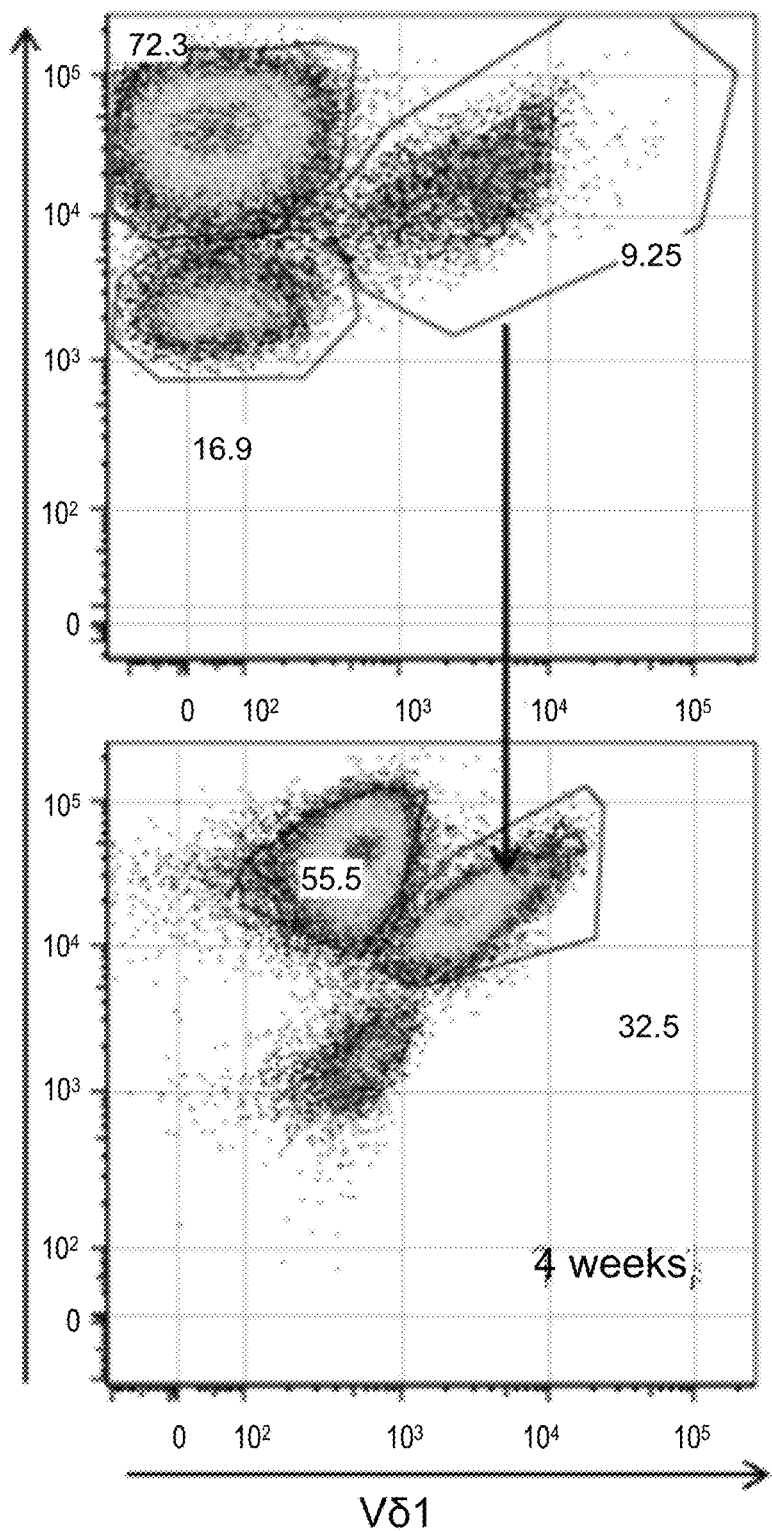
Figure 9A:
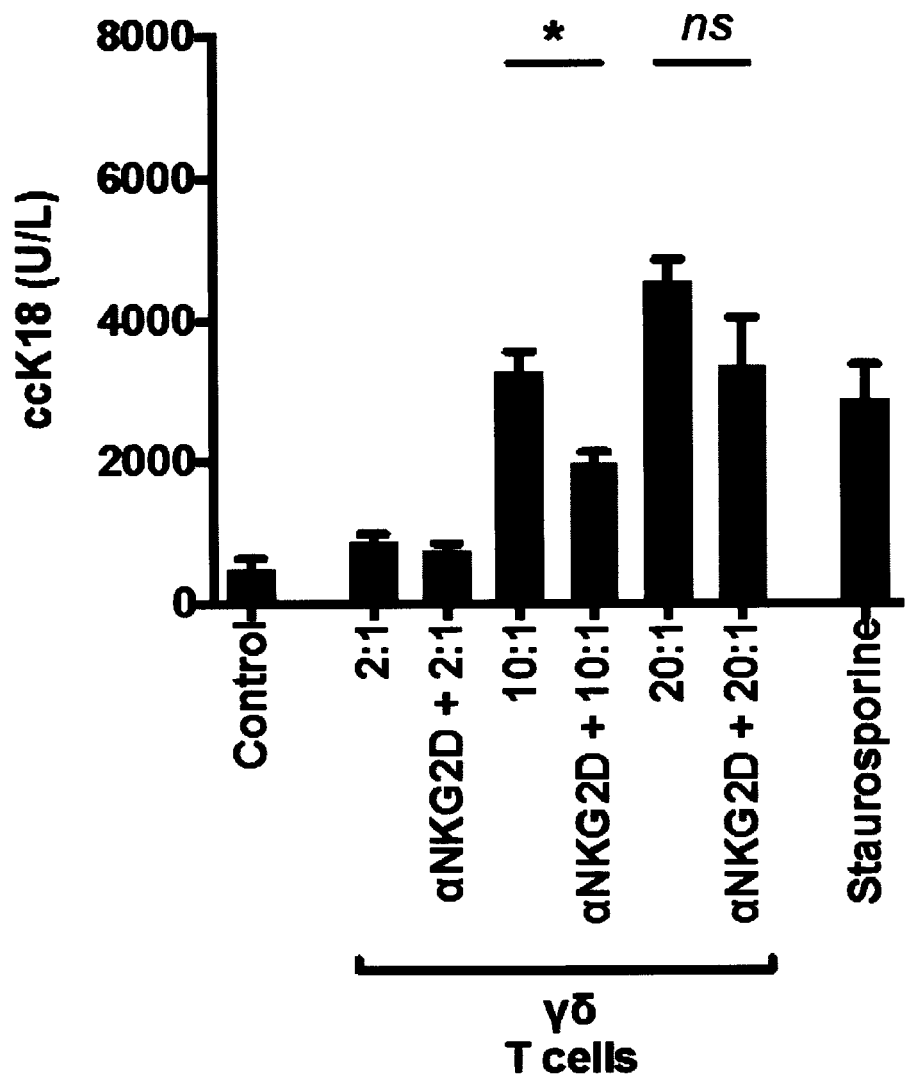
FIG. 9 shows that expanded and negatively sorted skin-derived γδ T cells display strong cytotoxicity against various human tumor cell lines with which they are co-cultured as measured by release of caspase-cleaved cytokeratin 18 by target cells, using ELISA.
Figure 9B:
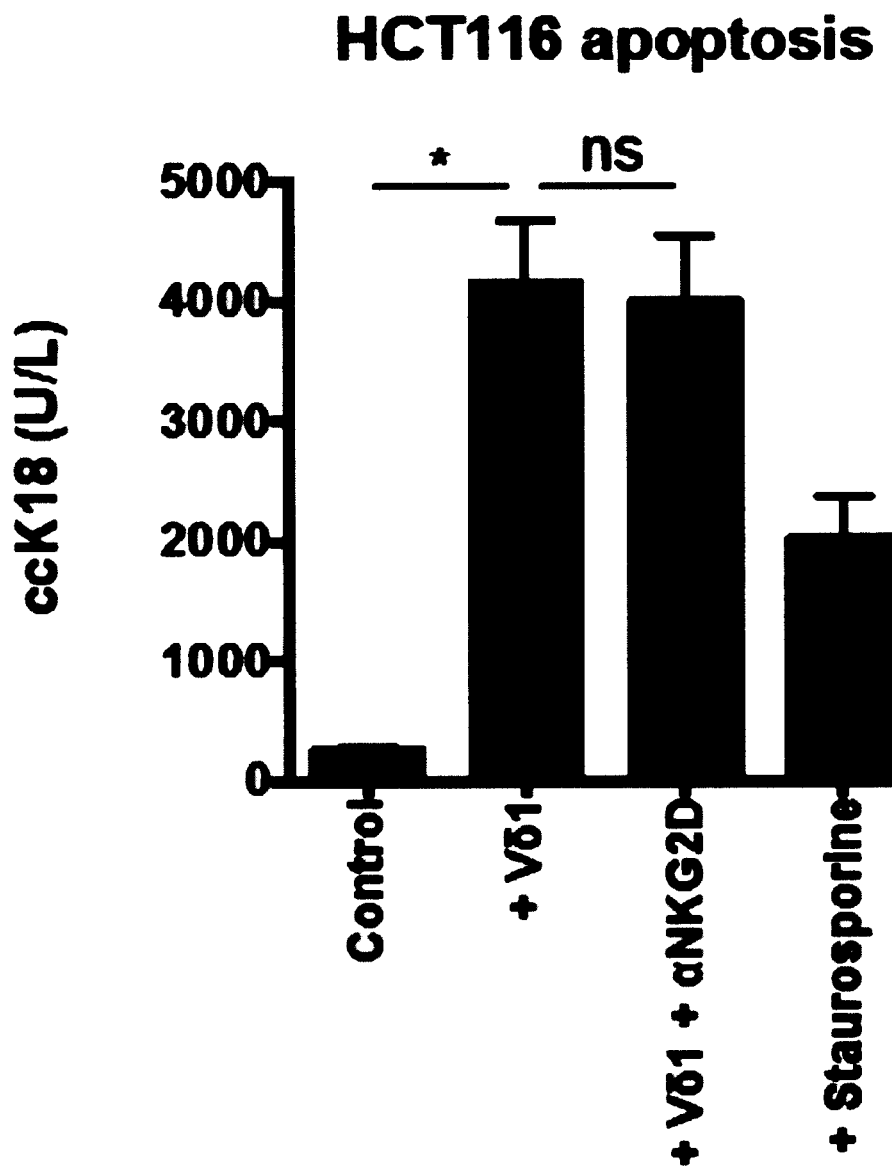
Figure 9C:
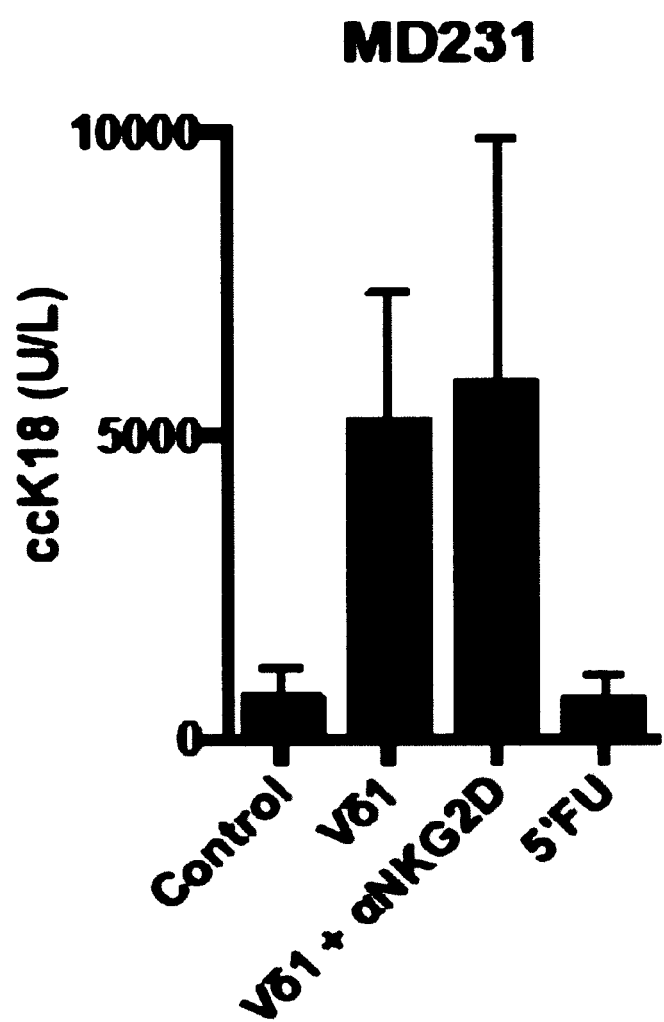

Furthermore, the cells produced large amounts of spontaneous IL-13, associated with atopic responses, during expansion and in contrast to freshly isolated skin-derived, TCR-activated γδ T cells. Other cytokines, such as IL-17A, were produced at much lower levels or not at all (FIG. 8). The high effector potentials of the cells could be increased further following stimulation with recombinant MICA (NKG2D ligand), anti-CD3, or PMA/ionomycin. To assess the cytotoxic potential of expanded γδ T cells against malignant target cells, we used established transformed cell lines in 24 hour co-culture experiments. Vδ1⁺ and DN γδ T cells showed very high cytotoxic activity towards Hela cells (cervix) and Caco2 (colon), in a dose-dependent fashion superior to conventional tissue αβ T cells (FIG. 5B). Furthermore, γδ-cell mediated cytotoxicity could be strongly inhibited by blocking the NKG2D receptor using soluble monoclonal antibodies indicating that this receptor is at least partly involved in tumor surveillance by de-repressed human skin-derived γδ T cells. The cytotoxic potential of these cells were further confirmed using other targets: HCT1954 (breast carcinoma), MDAMB231 (breast carcinoma), and HCT116 (colon) (FIG. 9).

Figure 7A:
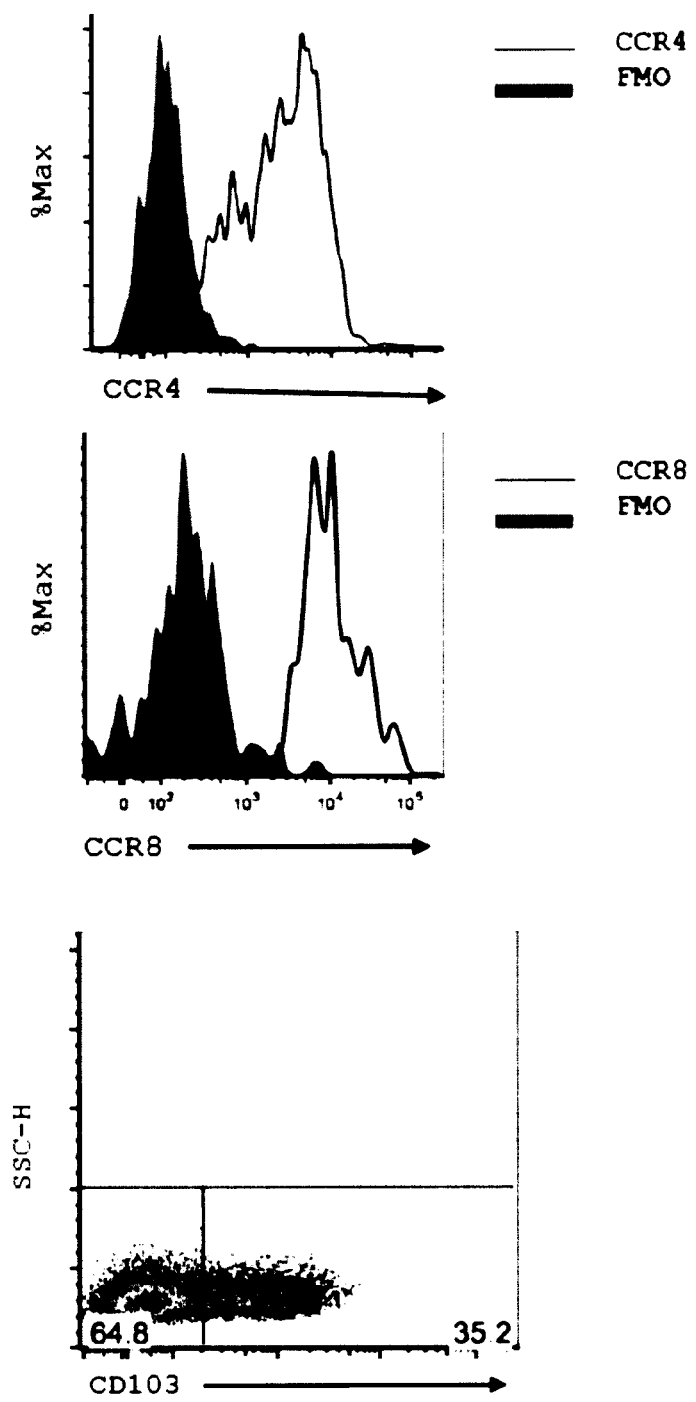
FIGS. 7A and 7B show the tissue phenotype of expanded skin-derived γδ T cells.
Figure 7B:
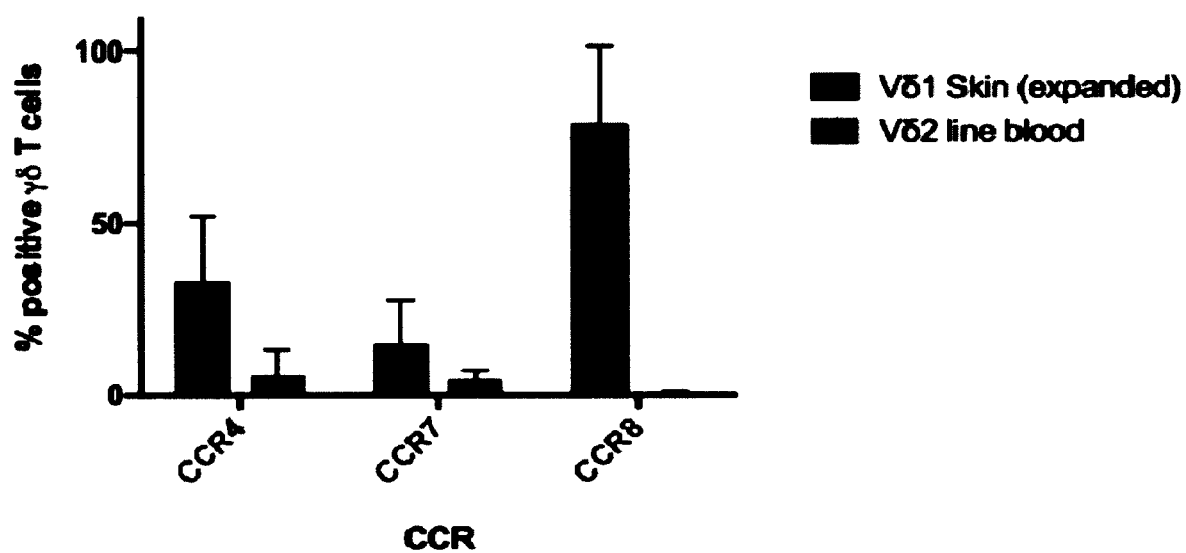
Figure 10A:
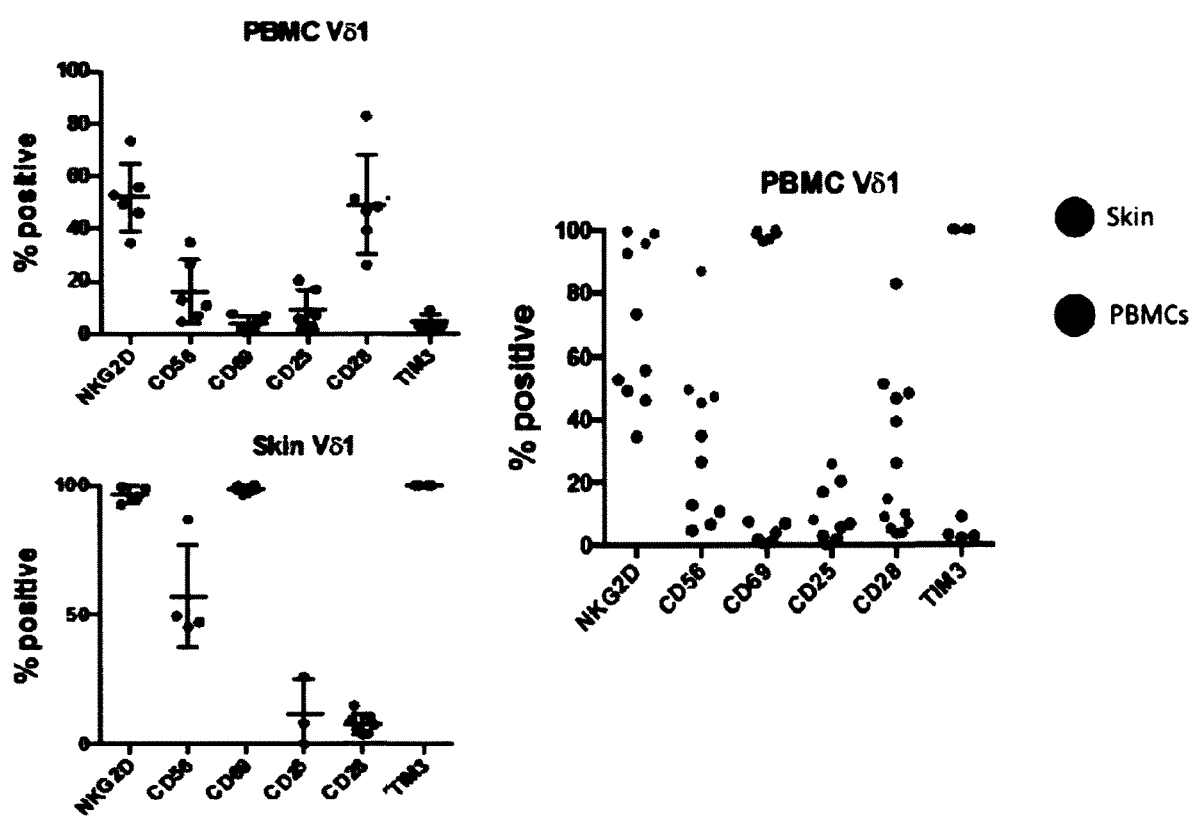
FIGS. 10A and 10B show that fresh, non-expanded skin-derived Vδ1 T cells show markers of prior T cell activation.
Figure 10B:
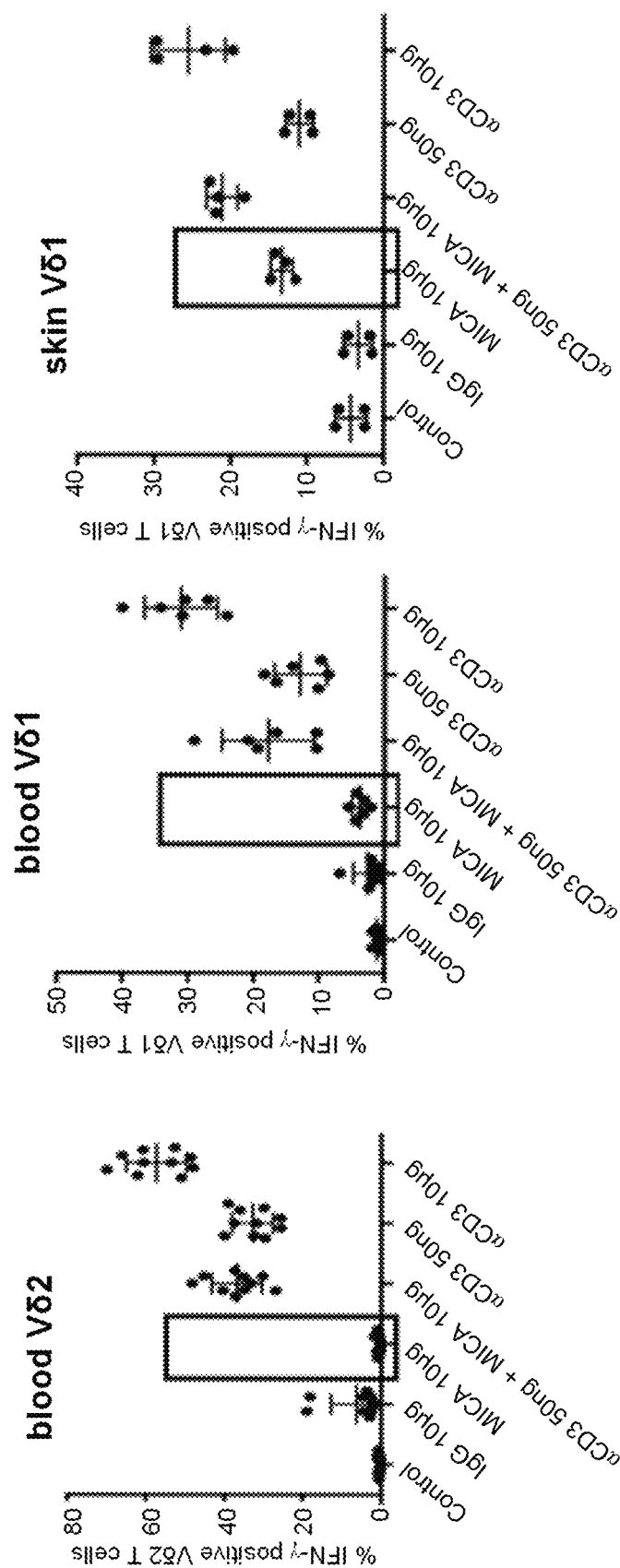

Non-haematopoietic tissue-resident γδ T cells produced by the method of the invention may further be distinguished from other blood-derived γδ T cells in that they respond to NKG2D ligand (MICA), which is strongly associated with malignancy, in the absence of any T cell receptor stimulating ligand, for example by increased production of TNFα, IFNγ, and CD107a (FIG. 2 and FIG. 10). They also execute a cytotoxic T cell response without undergoing any exogenous pharmacological or ligand mediated activation of the T cell receptor and are therefore cytotoxic in the absence of stimulation (FIG. 3 and FIG. 5). This means that compared with other γδ T cells, with αβ T cells or with NK cells, the non-haematopoietic tissue-resident γδ T cells produced by the method of the invention are unique in their ability to respond and proliferate in the absence of addition of any exogenous agents activating T cell receptor signaling (FIG. 3). The non-haematopoietic tissue-resident γδ T cells produced by the method of the invention also stained positive for CD69 and PD-1, lacked expression of CD28, and expressed only low levels of CD25 (see FIG. 1D). This combination of markers is not expressed by blood-derived γδ T cells. Furthermore, they showed higher expression of tissue homing receptors such as CCR4 and CCR8 compared to blood derived, expanded Vd2 γδ T cells (FIG. 7B).

Tissue-Resident γδ T Cells in Human Gut

Figure 11:
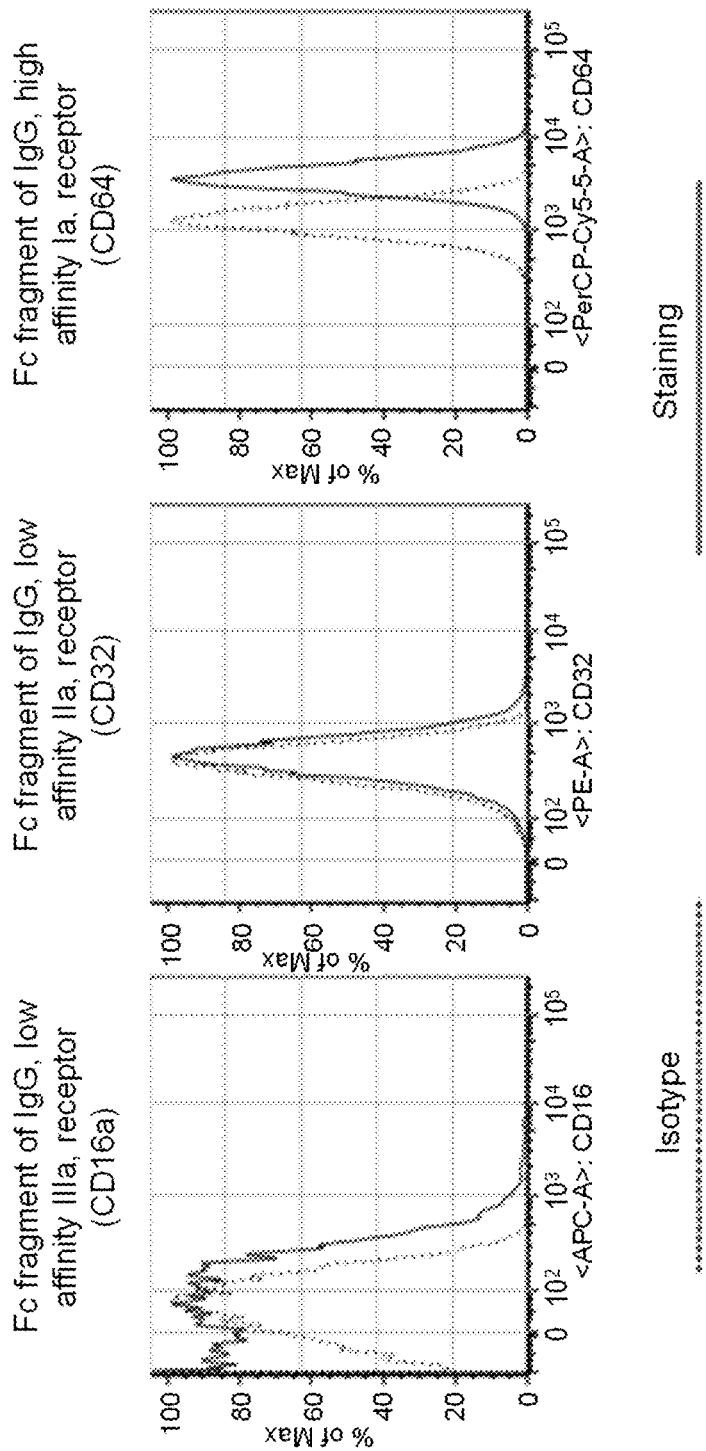
FIG. 11 shows that skin-derived Vδ1 T cells express minor levels of CD16 but show substantial surface expression of the high affinity IgG receptor CD64. Therefore in addition to direct cytotoxic activity, tissue-derived Vδ1 T cells could also be used to increase efficacy of monoclonal antibody therapies such as CD20 or Her2 therapies as they would be guided by the antibody to sites of malignancies and metastasis, recognize opsonized tumor cells and kill them via antibody-dependent cell-mediated cytotoxicity (ADCC). The results shown are from one representative donor (of four).
Figure 12:
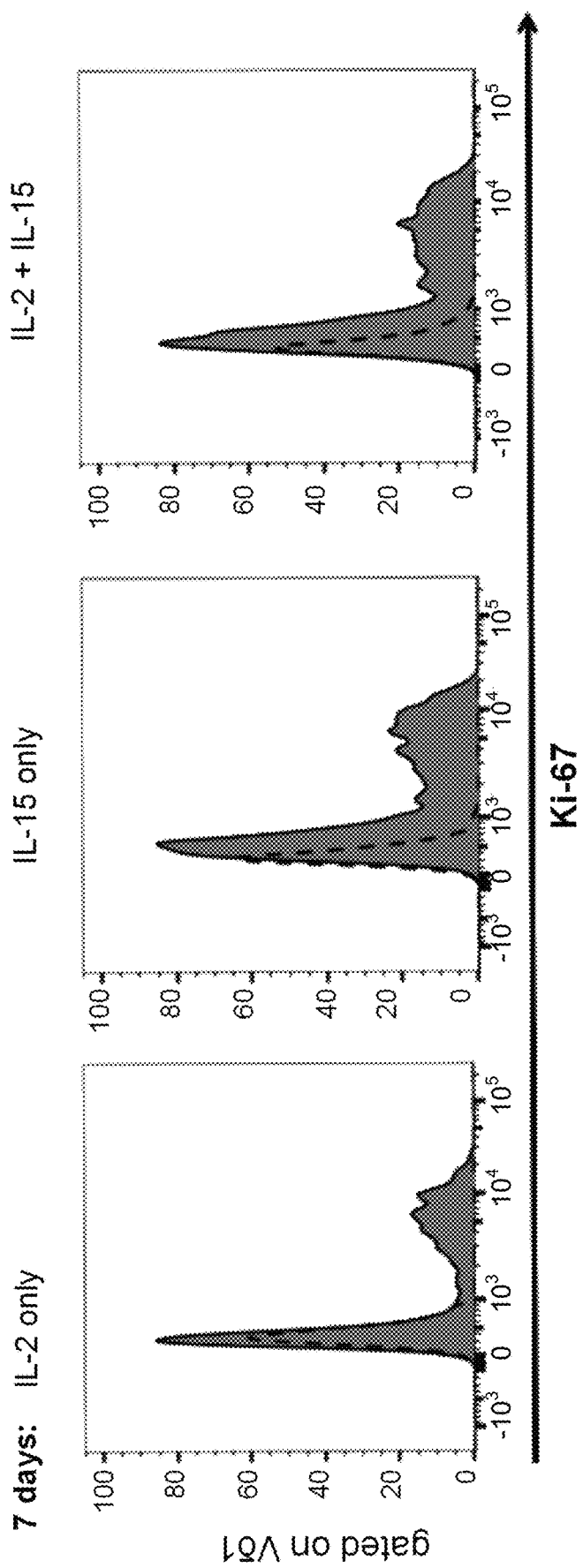
FIG. 12 shows the expansion of Vδ1 T cells in IL-2 (left panel), IL-15 (center panel), and IL-2+IL-15 (right panel). Freshly isolated skin derived lymphocytes were cultured in 96 well flat bottom plates in RPMI Medium containing 10% FCS and 1% Pen/Strep and were supplemented with IL-2, IL-15, or IL-2+IL-15 respectively for 7 days. Both IL-2 and IL-15 as, well as the combination of both cytokines, induced proliferation of Vb1 T cells as indicated by the shift in Ki-67 staining compared to isotype (true negative) staining in the absence of any stromal cells. Ki-67 specifically stains cells that have left G0 of the cell cycle and is commonly associated with proliferation.
Figure 13:
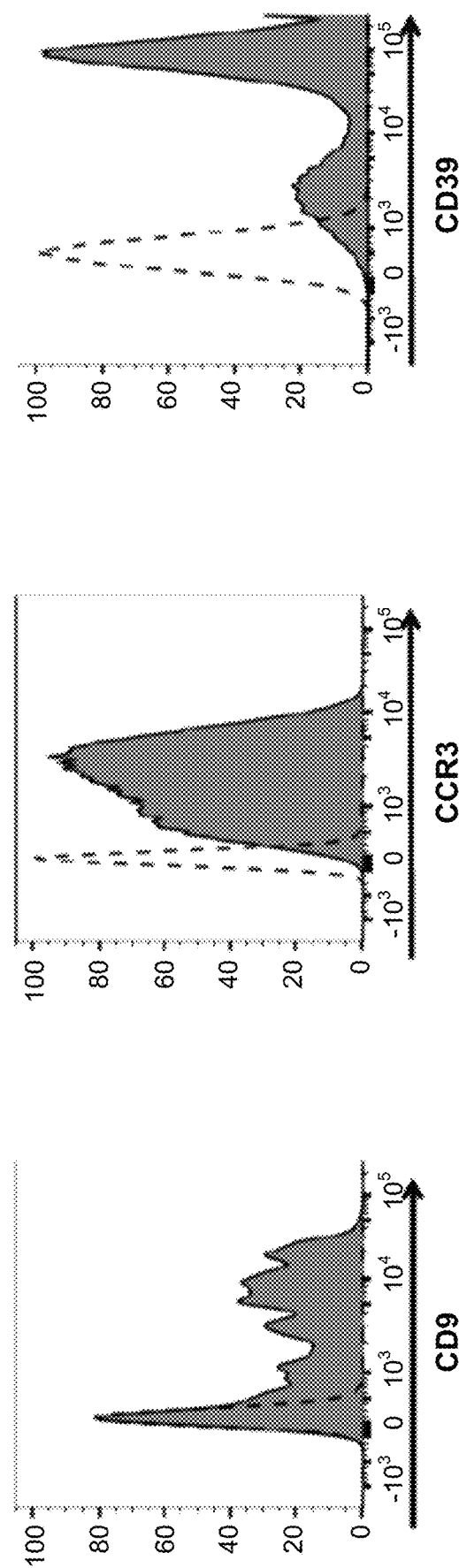
FIG. 13 shows flow cytometry results which indicate the expression of CD9, CCR3, and CD39 on the surface of expanded Vδ1 T cells on day 21. The expanded skin derived Vδ1 T cells maintained high levels of the cell surface markers, CCR3, CD39, and CD9 as indicated by (dark histogram) versus the equivalent isotype staining (true negative, open histogram).
Figure 14:
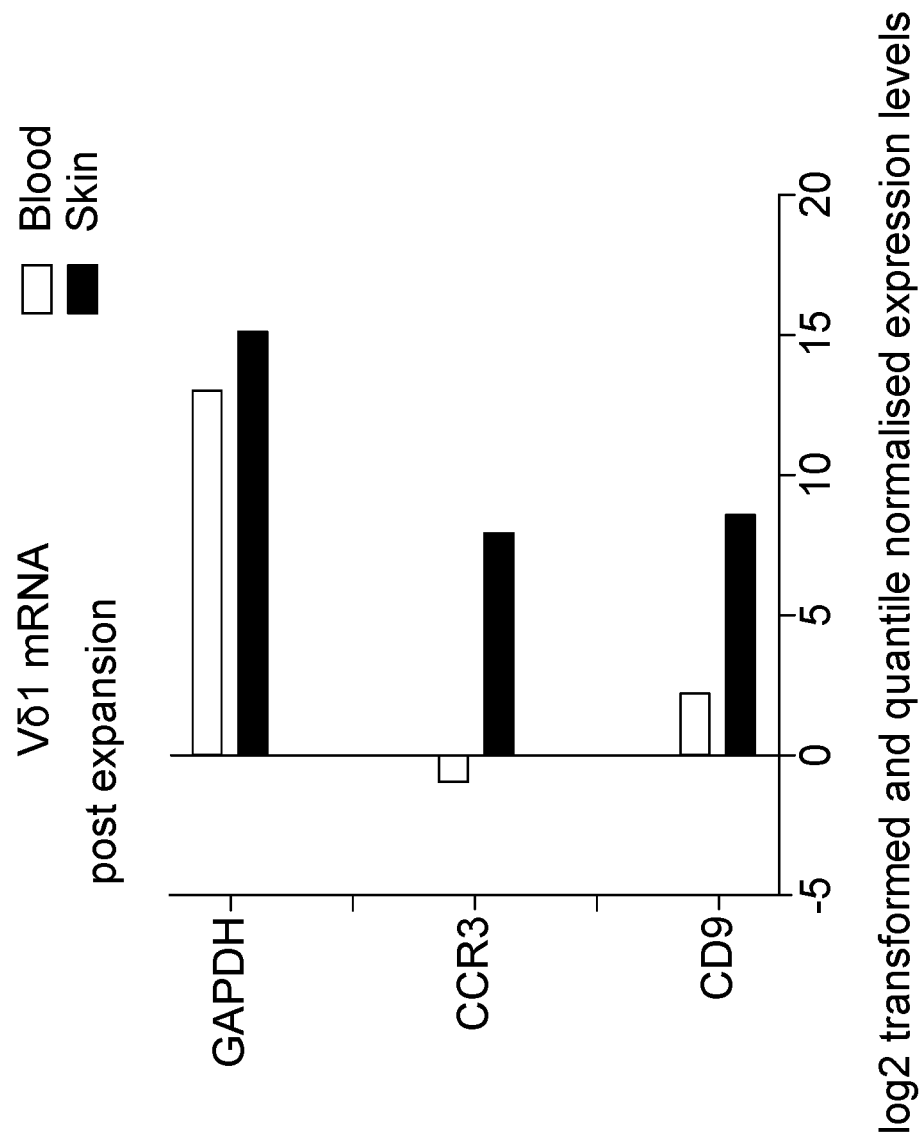
FIG. 14 shows the mRNA expression of CCR3 and CD9 in skin derived Vδ1 T cells (dark bars) and blood derived Vb1 T cells (light bars). Skin derived Vδ1 T cells were expanded as disclosed herein, and blood derived Vb1 T cells were expanded using plate bound antibodies for the Vδ T cell receptor (20 μg/mL). After expansion, Vb1 T cells were isolated using Fluorescence Activated Cell Sorting (FACS) and RNA was isolated from 3 donors for both groups (blood=grey vs. skin=black). Whole mRNA was sequenced and expression levels of indicated mRNAs normalized and log 2 transformed. All expression levels are shown in direct comparison, and in ratio to GAPDH, a common housekeeping gene expressed at high levels in most human cells.
Figure 15:
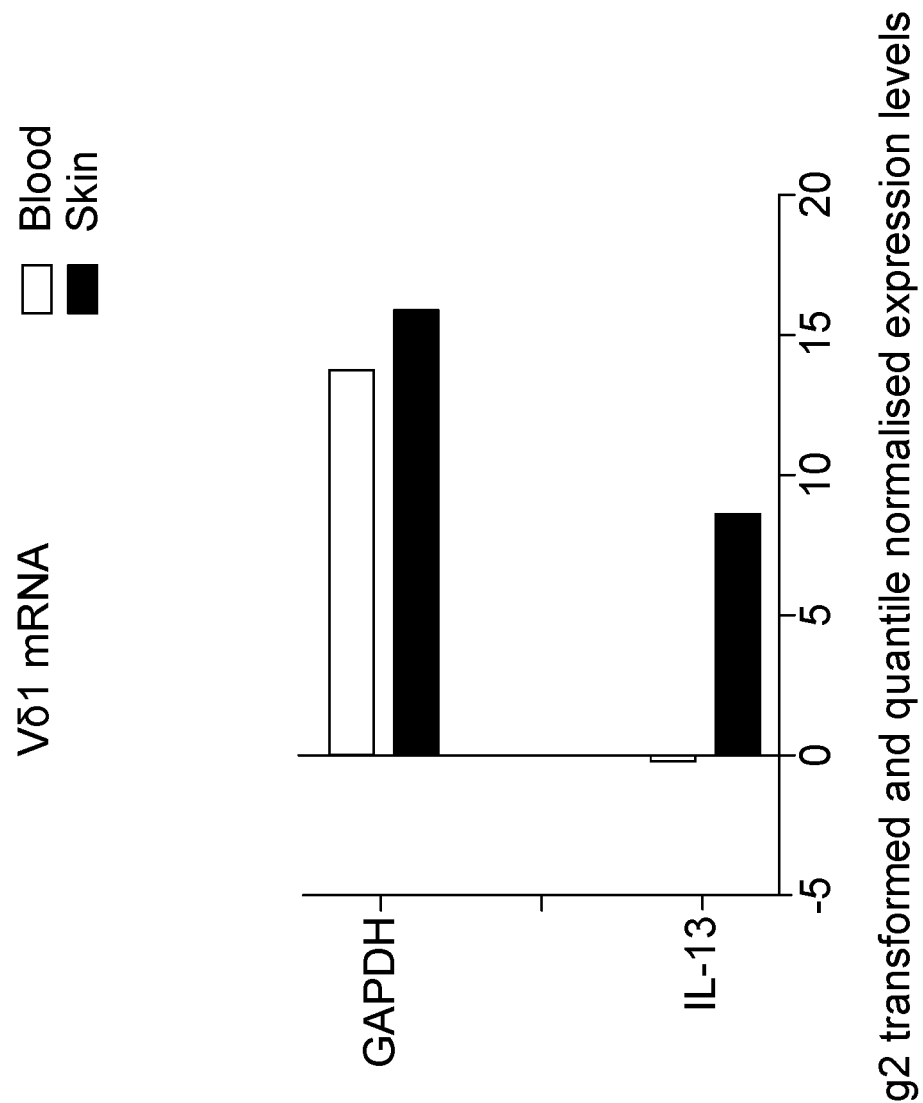
FIG. 15 shows the mRNA expression of IL-13 in skin derived Vδ1 T cells (dark bars) and blood derived Vδ1 T cells (light bars). Skin derived Vδ1 T cells were expanded as disclosed herein, and blood derived Vδ1 T cells were expanded using plate bound high dose antibodies for the Vδ T cell receptor (20 μg/ml). After expansion, Vδ1 T cells were isolated using FACS and RNA was isolated from 3 donors for both groups (blood=grey vs. skin=black). Whole mRNA was sequenced and expression levels of mRNAs for IL-13 were normalized and log 2 transformed. Expression levels are shown in direct comparison, and in ratio to GAPDH.
Figure 16A:
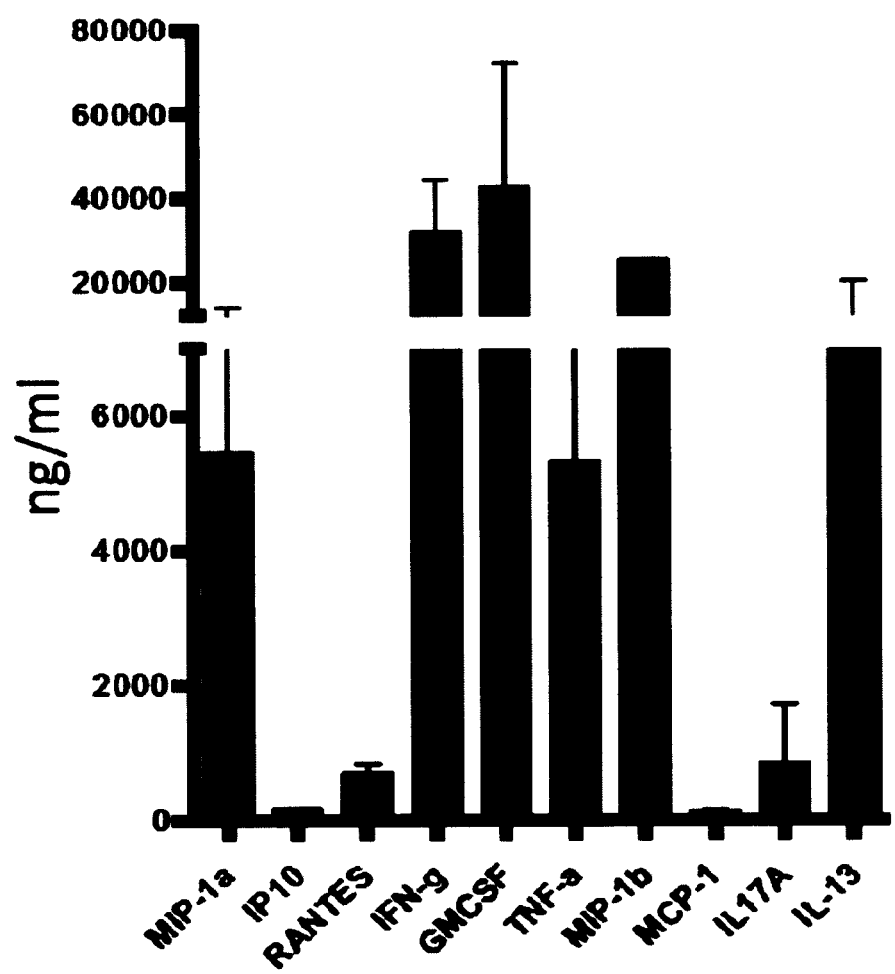

A human colon-derived population of non-haematopoietic tissue-resident population of γδ T cells expressing a Vδ1 T cell receptor was also identified (FIG. 6). In three donors, these cells were expanded using the same methods as were employed for skin cells, over a time course of 4 to 5 weeks. During expansion, colon-derived Vδ1⁺ and DN γδ T cells showed a similar pattern of Ki-67 up-regulation after their isolation from fibroblast-rich organotypic cell culture. Likewise, colon-resident Vδ1⁺ and DN γδ T cells were strongly stimulated by the provision of ligands for the NKG2D receptor. Blood-derived γδ T cells are well equipped to execute antibody dependent cell-mediated cytotoxicity via CD16 expression, proving enhanced cytotoxicity targeted against a CD20-positive B lineage lymphoma when combined with rituximab. Similarly, chronic lymphocytic leukemia (CLL) and HER2-positive breast cancer cells can be killed more effectively when targeted with monoclonal antibodies. In order to evaluate the potential of skin derived Vδ1 T cells to target antibody opsonized target cells, expression levels of the three IgG1 associated Fc receptors, CD16, CD32 and CD64, were quantified. Skin derived Vδ1 T cells express minor levels of the Fc receptor CD16, but show good expression levels for the high affinity IgG receptor CD64 (FIG. 11). Therefore, tissue-derived Vδ1 T cells may be well equipped to be used as an adjuvant to monoclonal antibody therapies such as CD20 or Her2 therapies, by guidance by the antibody to sites of malignancies and metastasis, recognizing opsonized tumor cells, and killing targets via ADCC.

Example 4. Optimization of Non-Haematopoietic Tissue-Resident γδ T Cell Expansion Conditions Expansion of Skin-Derived γδ T Cells Mixed lymphocytes were harvested after three to four weeks of scaffold culture, washed in PBS, spun down, and re-suspended in Roswell Park Memorial Institute 1640 medium (RPMI-1640; Life Technologies) with filtered 10% heat-inactivated fetal bovine serum (Life Technologies), L-glutamine (292 µg/ml; Life Technologies), penicillin (100 units/ml; Life Technologies), streptomycin (100 µg/ml; Life Technologies), N-2-hydroxyethylpiperazine-N-2-ethane sulfonic acid (HEPES; 0.01 M; Life Technologies), sodium pyruvate (1 mM; Life Technologies), minimal essential media (MEM) non-essential amino acids (1×; Life Technologies) and 50 M 2-mercaptoethanol (Life Technologies) at a concentration of $1\times10^6$ cells/ml. The initial population of Vδ1+ cells was 1.12% of lymphocytes. Cells were seeded at 2×10⁵ cells/well into 96 well flat bottom plates (Corning) or at 2×10⁶ cells/well into 24 well plates (Corning) for expansion and supplemented with factors as indicated at concentrations provided in Table 2.

TABLE 2

Concentrations of each factor included in expansion cultures

| Factor | Concentration |
|---|---|
| IL-1β | 10 ng/ml |
| IL-2 | 100 U/mL |
| IL-4 | 5 ng/ml |
| IL-6 | 10 ng/ml |
| IL-7 | 25 ng/ml |
| IL-8 | 5 ng/ml |
| IL-9 | 10 ng/ml |
| IL-12 | 2.5 ng/ml |
| IL-15 | 10 ng/ml |
| IL-18 | 50 ng/ml |
| IL-21 | 10 ng/ml |
| IL-23 | 10 ng/ml |
| IL-33 | 500 ng/ml |
| SDF1α | 10 ng/ml |
| IGF-1 | 100 ng/ml |

Figure 17A:
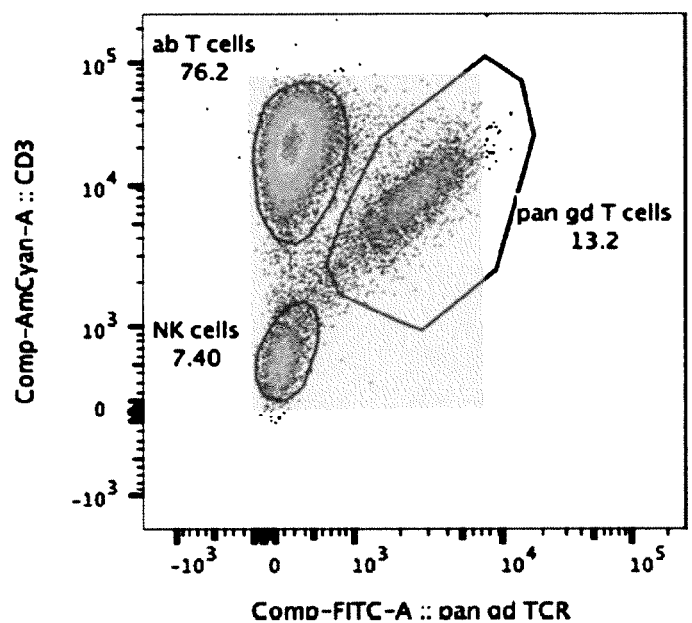
Figure 17B:
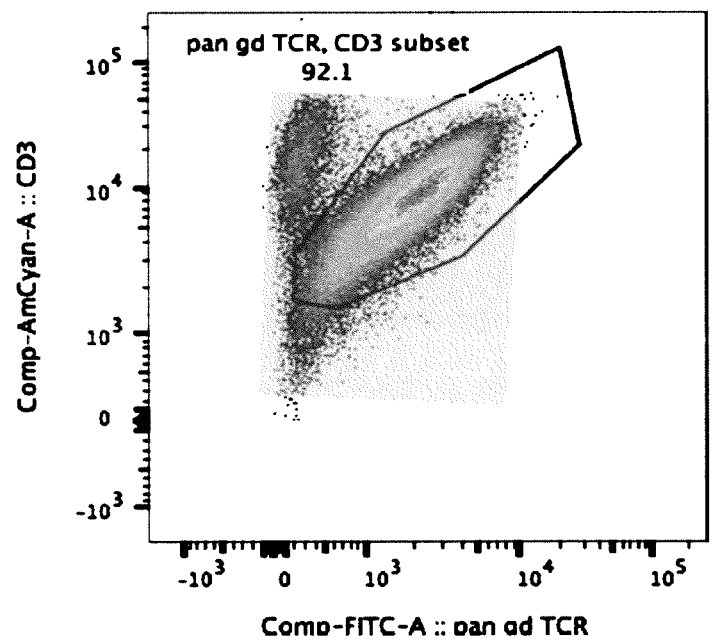

Cells were monitored daily by microscopy and provided with fresh media and cytokines three times per week. Upon full confluence and cell aggregation, cells were split 1:1 into additional wells and plates, as required. After 21 days, cells were harvested using ACCUTASE® (eBioscience), counted, and analyzed using flow cytometry. FIG. 17A and FIG. 17B show representative flow cytometry plots before and after expansion. Table 3 shows fold-expansion values corresponding to FIG. 17C in addition to relative CD27 and TIGIT expression on expanded cells of each treatment group. Final Vδ1 fold expansions were calculated using pre- and post-expansion Vδ1 total numbers (% CD3+ pan γδ+ Vδ1+ cells÷100)×(total cell number).

TABLE 3

Expansion of skin-resident Vδ1 T cells in the presence of various factors.

| Expansion Factor (IL-2 + IL-15)+ | Expansion of Vδ1 normalized to IL-2 + IL-15 | CD27 MFI on Vδ1 normalized to IL-2 + IL-15 | TIGIT MFI on Vδ1 normalized to IL-2 + IL-15 |
|---|---|---|---|
| IL-4 | 1.5 ± 0.5 | 1.4 ± 0.5 | NT |
| IL-6 | 1.9 ± 0.3 | 0.9 ± 0.4 | 1.0 ± 0.1 |
| IL-7 | 1.6 ± 0.3 | 0.5 ± 0.7 | 1.1 ± 0.2 |
| IL-8 | 1.6 ± 0.2 | 1.0 ± 0.3 | NT |
| IL-21 | 2.9 ± 1.6 | 2.8 ± 0.8 | NT |
| IL-23 | 1.3 ± 0.5 | 0.7 ± 0.5 | NT |
| SDF-1 | 3.9 ± 1.9 | 0.9 ± 0.4 | NT |
| IL-4 + IL-21 | 7.4 ± 5.0 | 7.3 ± 2.5 | 0.4 ± 0.1 |
| IL1b | 3.0 ± 1.4 | 1.0 ± 0.4 | 1.1 ± 0.3 |
| IL-12 | 6.8 ± 4.3 | 0.7 ± 0.8 | NT |
| IL-18 | 3.3 ± 1.0 | 0.8 ± 0.5 | 0.9 ± 0.2 |
| IL-33 | 2.5 ± 1.3 | 1.1 ± 0.4 | 0.9 ± 0.2 |
| IL-33 + IL-4 + IL-21 | 2.0 ± 1.3 | 0.7 ± 3.5 | 0.4 ± 0.2 |
| IGF-1 | 1.1 ± 0.1 | 0.9 ± 0.1 | 1.2 ± 0.1 |
| IL-9 | 0.9 ± 0.4 | 1.2 ± 0.0 | 1.3 ± 0.2 |
| IL-9 + IL-4 + IL-21 | 1.8 ± 1.3 | 7.4 ± 3.9 | 0.3 ± 0.1 |
| IL-4 + IL-21 + 1% HPL | 5.3 ± 0.5 | 5.4 ± 1.0 | 0.3 ± 0.1 |
| IL-4 + IL-21 + 5% HPL | 4.7 ± 0.9 | 4.8 ± 2.9 | 0.4 ± 0.1 |

Figure 17C:
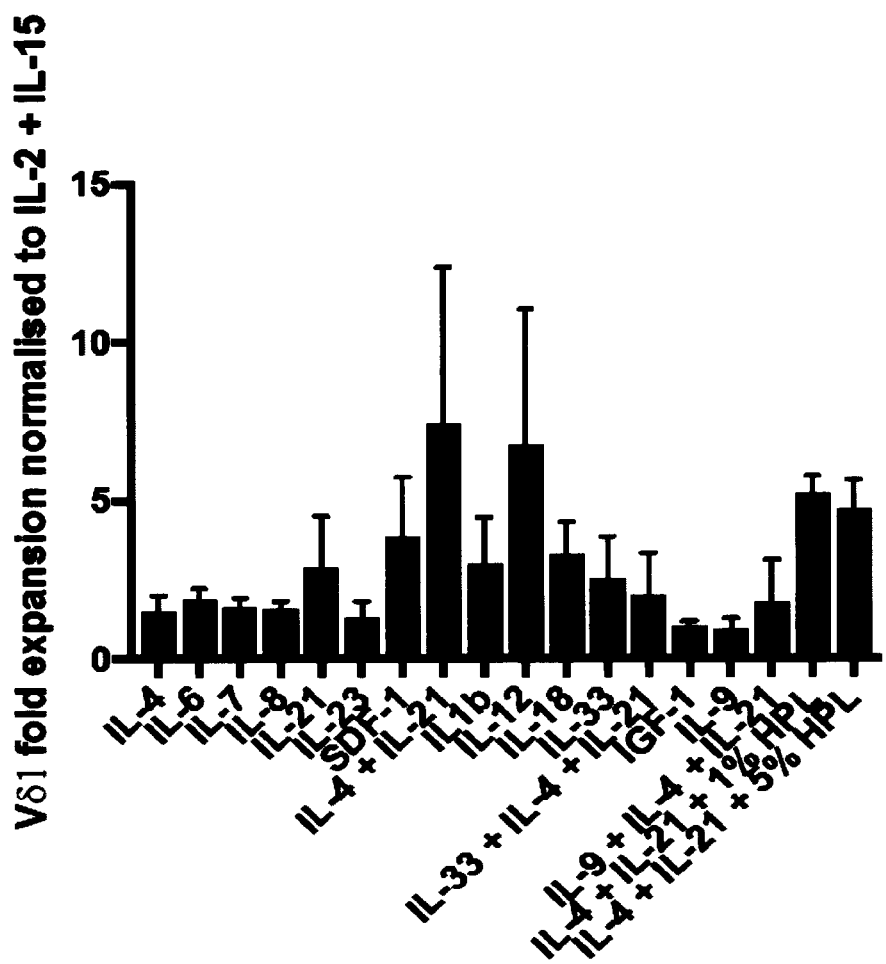
Figure 17D:
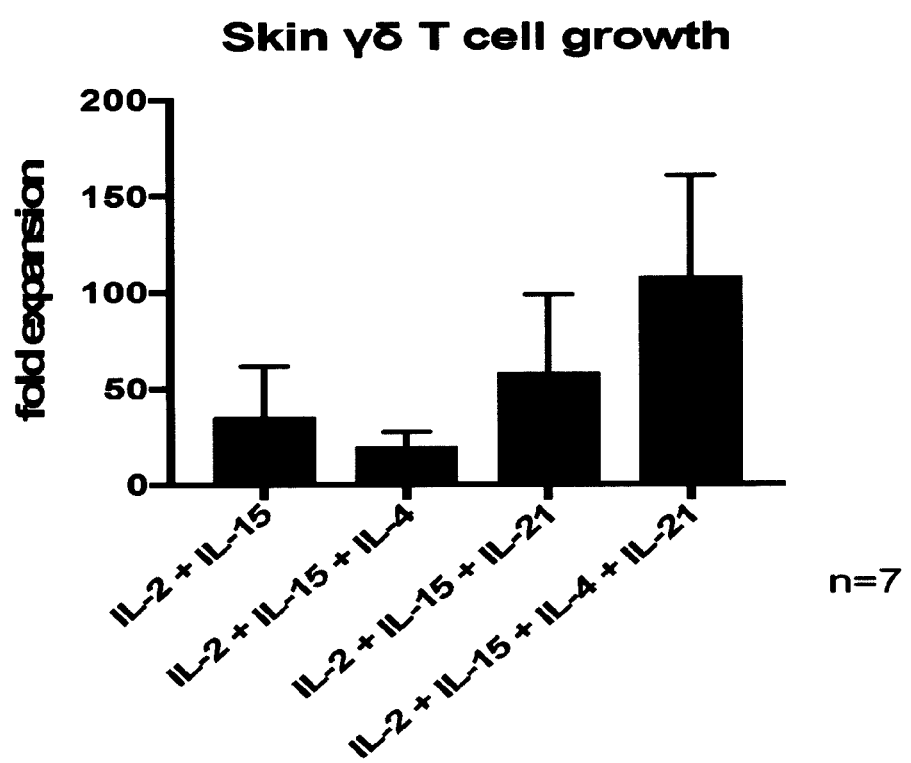
Figure 17F:
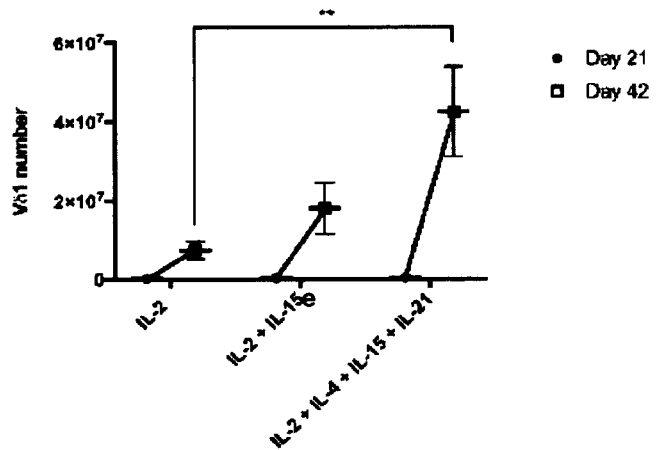
Figure 17G:
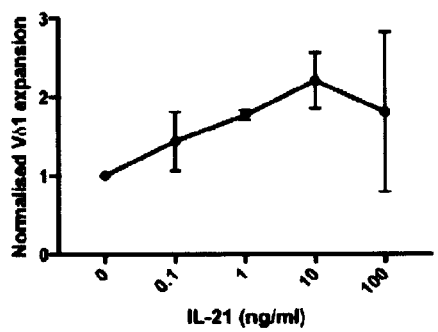
Figure 17H:
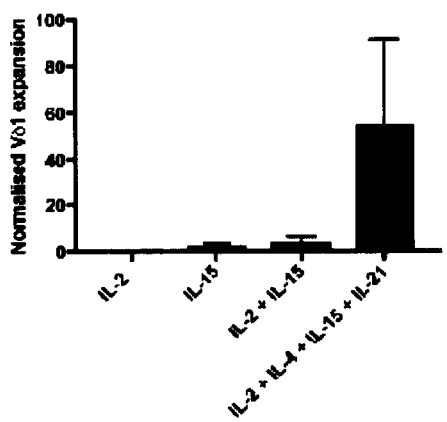

In comparison to expansion in IL-2 and IL-15 alone, addition of other factors increased expansion of Vδ1 T cells, as shown in FIG. 17C. Given the high yield of Vδ1 T cells in response to IL-2, IL-15, IL-4, and IL-21, combinations of these factors were further investigated, as shown in FIG. 17D-17H.

Initial and final phenotypes of each Vδ1 T cell population, including expression of CD27 and TIGIT, was determined using mean fluorescence intensity (MFI), and samples within each group were averaged by taking the median MFI. Expression of CD27 and TIGIT by Vδ1+ T cells under each expansion condition is shown in Table 4.

TABLE 4

Phenotype of skin-resident Vδ1 T cells expanded in the presence of various factors.

| Expansion Factor | CD27 MFI | TIGIT MFI |
|---|---|---|
| IL-2 | 113 ± 5 | 7919 ± 179 |
| IL-2, IL-15 | 226 ± 33 | 4788 ± 679 |
| IL-2, IL-15, IL-6 | 140 ± 91 | 6663 ± 767 |
| IL-2, IL-15, IL-7 | 128 ± 115 | 6083 ± 1813 |
| IL-1, IL-15, IL-4, IL-21 | 1284 ± 1048 | 1721 ± 308 |
| IL-2, IL-15, IL1β | −136 ± 3.5 | 9453 ± 390 |
| IL-2, IL-15, IL-18 | 121 ± 75 | 4396 ± 2782 |
| IL-2, IL-15, IL-9 | 260 ± 21 | 5247 ± 2333 |
| IL-2, IL-15, IGF-1 | 193 ± 94 | 6584 ± 1127 |
| IL-2, IL-15, IL-4, IL-21, IL-9 | 790 ± 61 | 1389 ± 803 |
| IL-2, IL-15, IL-4, IL-21, 1% HPL | 990 ± 258 | 1203 ± 222 |
| IL-2, IL-15, IL-4, IL-21, 5% HPL | 421 ± 76 | 1045 ± 798 |

Figure 18A:
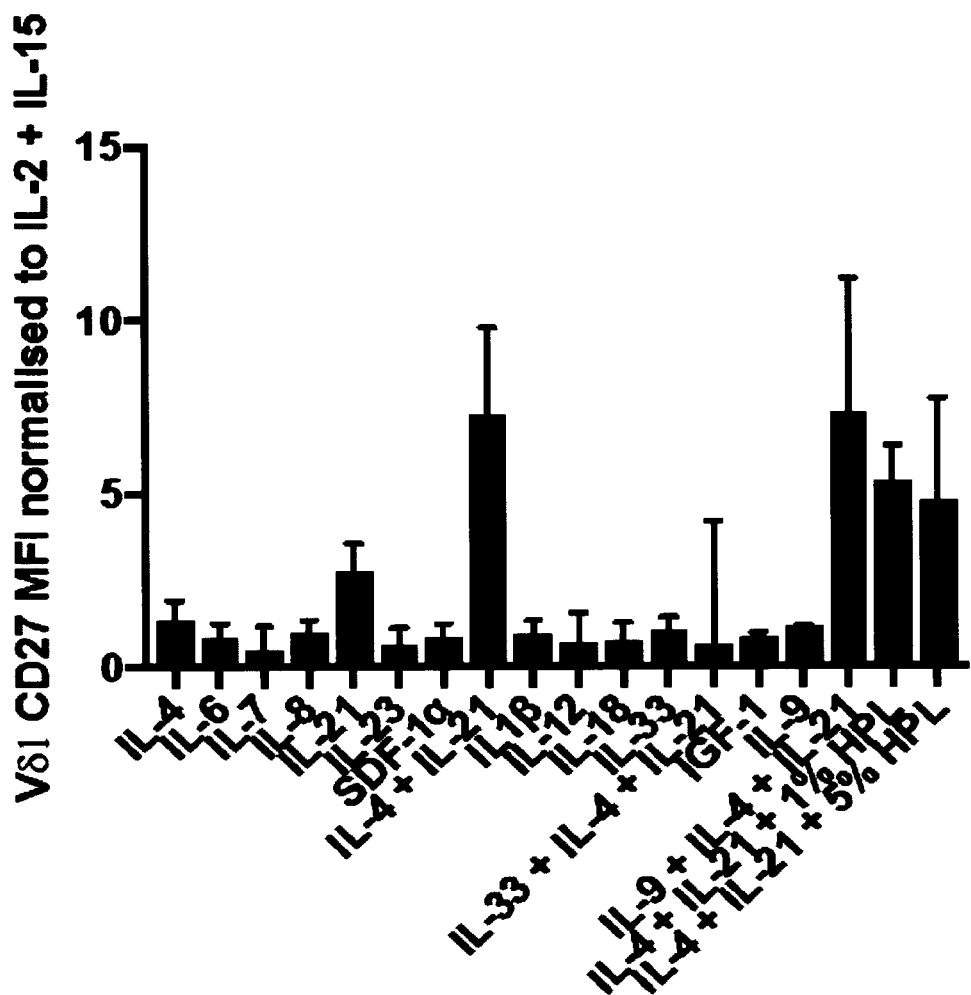
FIGS. 18A-18D characterize expression of CD27 by expanded Vδ1 T cells.
Figure 18B:
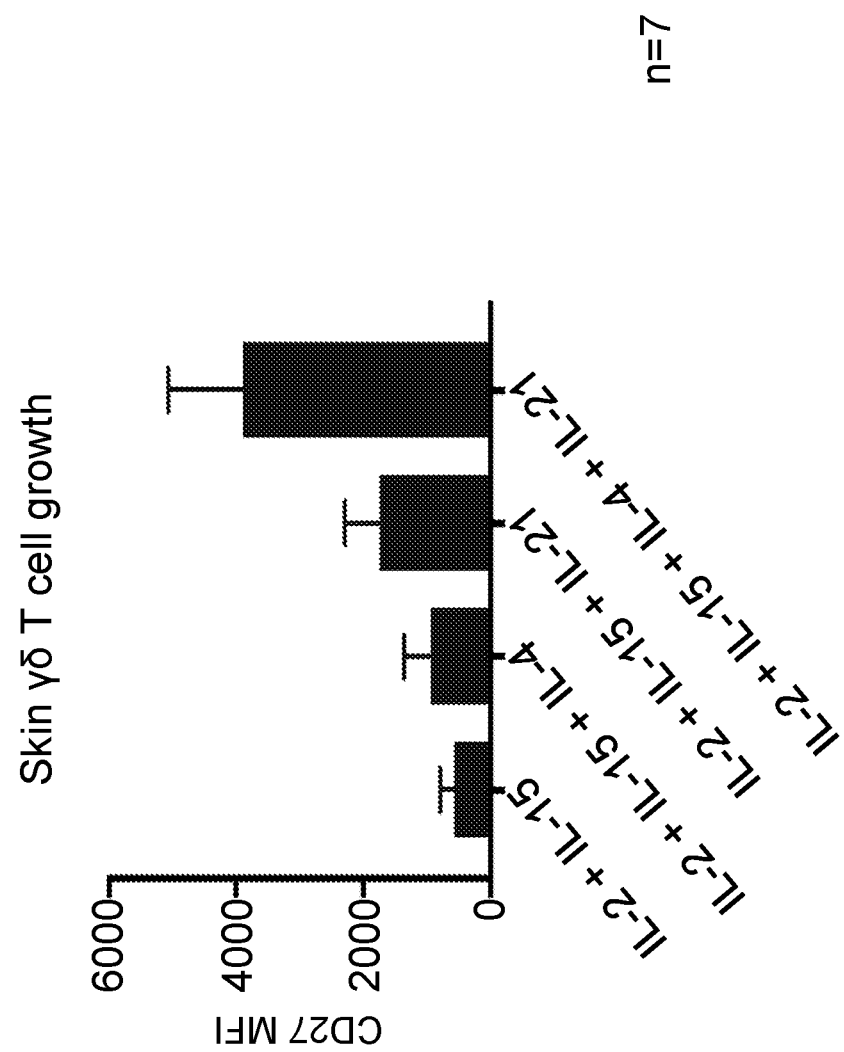
Figure 18C:
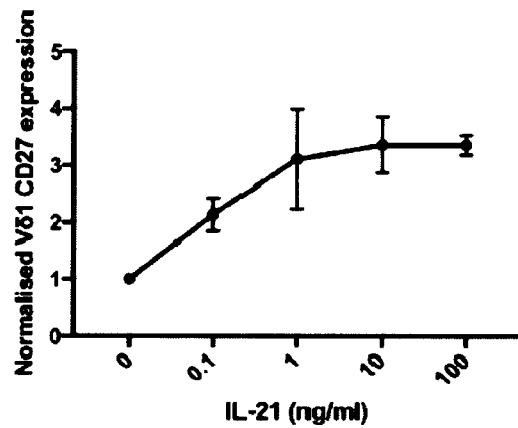
Figure 18D:
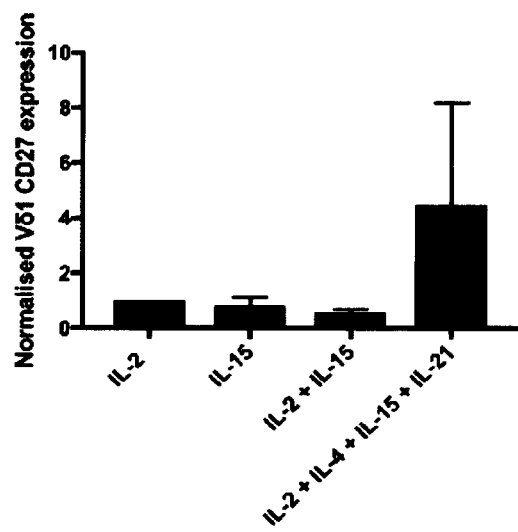

Relative to IL-2 and IL-15 alone, addition of other factors increased expression of CD27, as measured by mean fluorescence intensity, as shown in FIG. 18A. Of note, the addition of IL-4 and IL-21 raised CD27 MFI to about 8-fold relative to IL-2 and IL-15 alone. Again, the four-way combination of IL-2, IL-15, IL-4, and IL-21 yielded the highest expression of CD27, relative to other combinations thereof (FIGS. 18B and 18D). Of note, low expression of CD27 on T cells is often associated with an exhausted, terminally differentiated phenotype with little potential for further, long-term proliferation.

Figure 19:
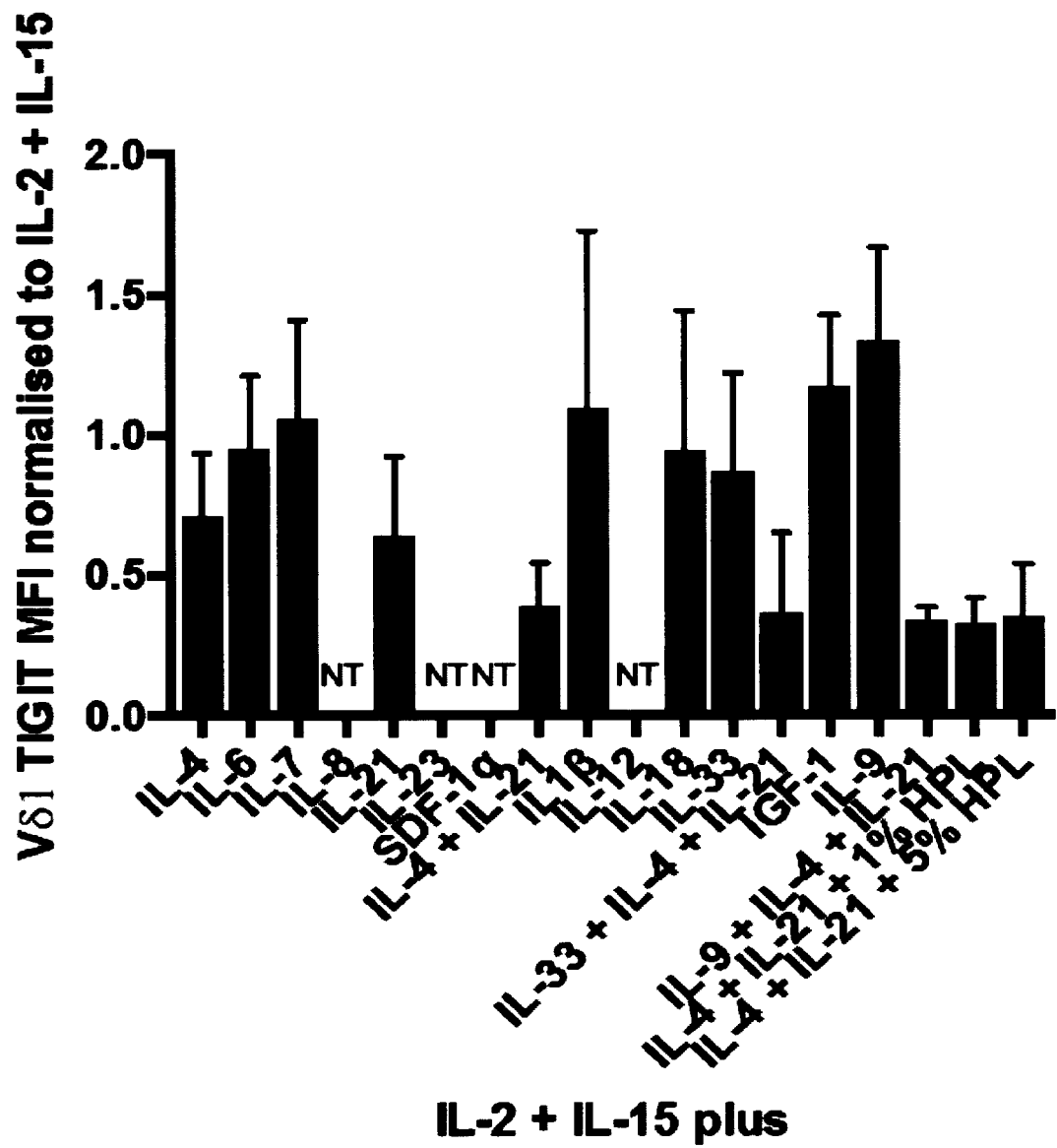
FIG. 19 characterize surface expression of TIGIT by expanded Vδ1 T cells.
Figure 20:
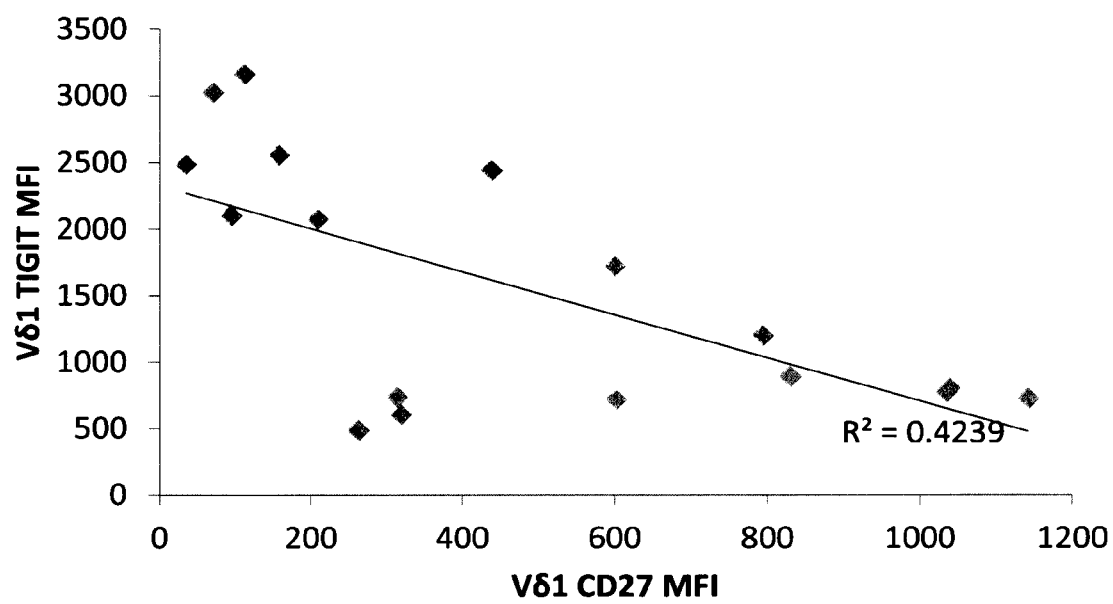
FIG. 20 is a plot showing surface TIGIT expression of individual cells as a function of CD27 expression.

A different trend was observed with respect to TIGIT expression by expanded Vδ1+ T cells (FIG. 19). In particular, TIGIT expression decreased in response to IL-4 and IL-21, in conjunction with IL-2 and IL-15. To further explore this trend, TIGIT expression was plotted as a function of CD27 expression (FIG. 20). A negative correlation between TIGIT and CD27 was observed. High TIGIT expression can render T cells susceptible to inhibition by a tumor microenvironment, where expression of its ligand poliovirus receptor (PVR; CD155), can be high.

Example 5. Four Cytokine Culture is Sufficient to Replace Cell Culture Serum

Figure 21:
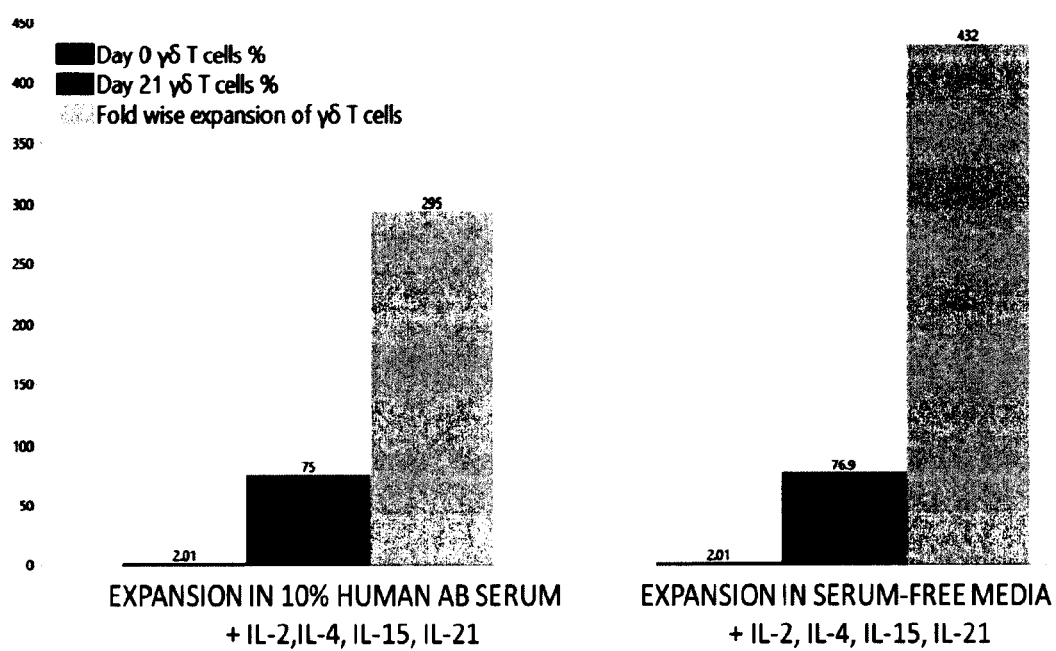
FIG. 21 is a graph showing the use of cytokines to support the expansion and enrichment of tissue-derived γδ T cells in the presence or absence of blood-derived serum or plasma fractions. Mixed lymphocyte populations isolated from a tissue sample containing 2% γδ T cells were expanded in the media containing IL-2, IL-4, IL-15 and IL-21 with or without 10% human AB serum. Data highlights successful and equivalent expansion (432 fold) and enrichment (from 2% to 77%) without human serum versus with serum (295 fold expansion, enrichment from 2% to 75%).
Figures 22A, 22B, 22C, 22D:
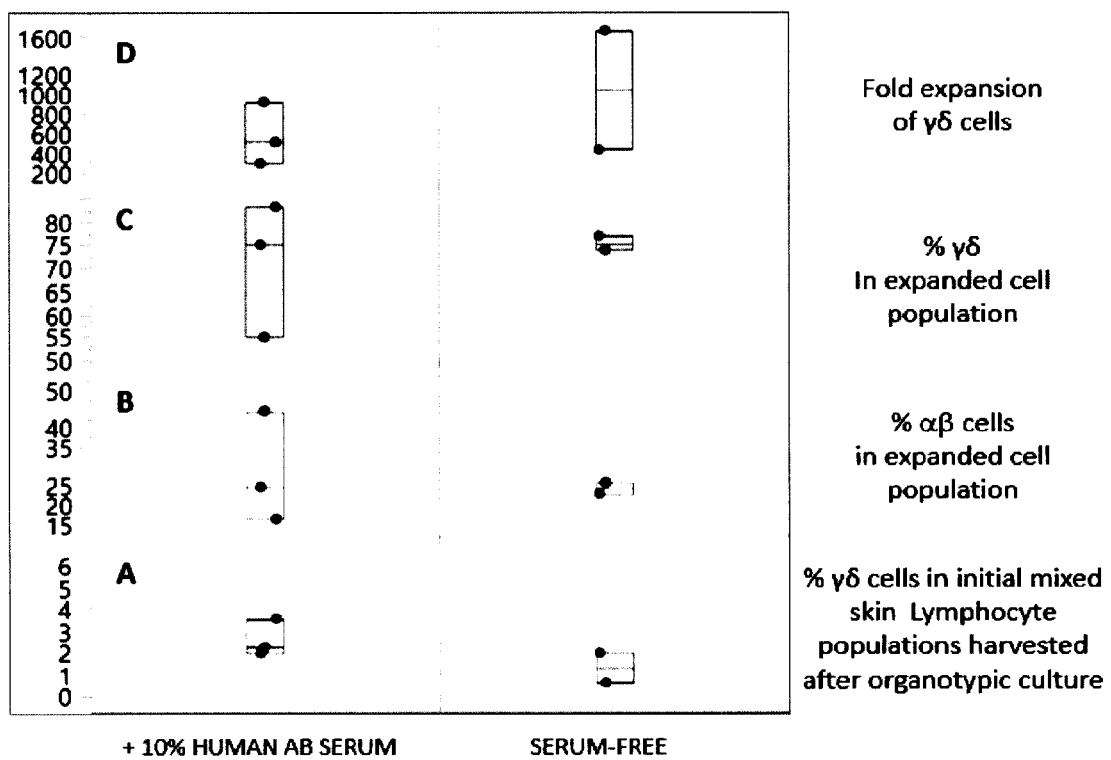
FIGS. 22A-22D are graphs showing example enrichment of tissue-derived γδ cells from isolated mixed lymphocyte populations. Cells were isolated from a single human tissue sample and replicates and then expanded in TexMACS media plus IL-2, IL-4, IL-15 and IL-21 containing either 10% serum (left-hand columns) or 5% cell therapy system serum (CTS™) (right-hand columns). The profiles of isolated and expanded cell cultures are presented as indicated.

Currently, the addition of complex blood-derived sera and plasma to media when manufacturing tissue or tumour resident derived T cells is commonplace. However, the use of these sera or plasma components can be undesirable because of the inherent batch to batch variation of such components, the high cost of such components, the limited supply given the high demand across the advanced therapy medicinal products (ATMP) industry, and the increased risk of adventitious agent cross-contamination from such components. Consequently, after successfully identifying cytokines that supported the expansion and enrichment of desired γδ T cells as described herein, it was tested whether the use of such cytokines could negate any requirement of complex serum/plasma components typically employed to expand tissue-derived γδ T cells. To test this further, immune cells were egressed from a skin sample and tested for whether plasmas/sera were still required to support the expansion and enrichment of γδ T cells +/−serum. Accordingly, the egressed cells were then harvested and seeded into two media on "day 0." The first medium comprised an animal derived component free (ADCF) media (TexMACS, Miltenyi) with 10% human derived serum and cytokines. The second media comprised the same ADCF media/cytokine mix, a standard defined supplement (CTS™, containing purified human serum albumin, recombinant insulin and transferrin) but without any serum addition. The results of this study are shown in FIG. 21. Surprisingly, equivalent enrichment and equivalent fold expansions were observed with or without the human serum. This shows that it is possible to expand and enrich tissue-derived γδ T cells without any animal derived components or human serum.

Next, this approach was assessed for preferential expansion of γδ T cells from starting mixed lymphocyte populations harvested from standard organotypic cultures. If achievable, such preferential expansion would be highly desirable, particularly if the protocols resulted in a final expanded lymphocyte population comprising >50% γδ T cells. Indeed, to date, conventional enrichment protocols require use of depletion or enrichment technologies such as magnetic immunodepleting technologies (e.g., from Miltenyi or Dynal) or flow cytometry sorting technologies (e.g., from BD Biosciences) to physically separate a minority of γδ cells or physically deplete a majority αβ cells. Instead, the present study assessed whether the present methods could enrich for γδ cells present in any given starting mixed lymphocyte population without the need for such physical separation or depletion protocols. Surprisingly, and due to the selectivity of the protocols for the expansion of γδ cell over and above other cell types also present in the starting population, such enrichment was achieved using these expansion methods. This resulted in a more enriched, purer γδ T cell population representing more than 50% of all cells present in the culture. This enrichment was achieved in the presence and/or absence of serum and is further shown in FIG. 21 and FIGS. 22A-22D wherein γδ T cells were expanded >100 fold, enhancing the purity of γδ T cells from <50% to >50% on all occasions for this tissue sample.

Isolation and Expansion Methods

Mixed lymphocytes were harvested from tissue after three weeks of scaffold culture using the equivalent approach as previously described by the Clark protocol as well as in Example 2. The resulting profile of the harvested cells were similar to those described in Example 3. These harvested cells were washed in HBSS+HEPES, spun down and resuspended in TexMACS media (Miltenyi) containing either (i) 10% human AB serum (Life Science Production) in addition to IL-2 (100 IU/L), IL4 (Biolegend, 5 ng/ml), IL-15 (Biolegend, 20 ng/ml), and IL-21 (Biolegend, 5 ng/ml) or (ii) 5% CTS™ (Thermo Fisher Scientific) in addition to IL-2 (100 IU/L), IL-4 (Biolegend, 5 ng/ml), IL-15 (Biolegend, 20 ng/ml), and IL-21 (Biolegend, 5 ng/ml). Both serum containing and serum-free media also contained pen/strep antibiotics (100 units/ml, 100 ug/ml respectively, Life Technologies). The cells were then seeded at 2 million cells/well in 24 well plates (Corning). Once cells became confluent, they were then expanded/passaged by splitting between 1-in-2 to 1-in-4 into new wells containing the same media. On day 21, the cells were harvested with aid of ACCUTASE® cell detachment solution (Thermo-Fisher) and analyzed by flow cytometry to determine final cell profiles as presented in FIG. 21 and FIGS. 22A-22D.

Example 6. Functional Relevance of TIGIT Expression

Figure 23:
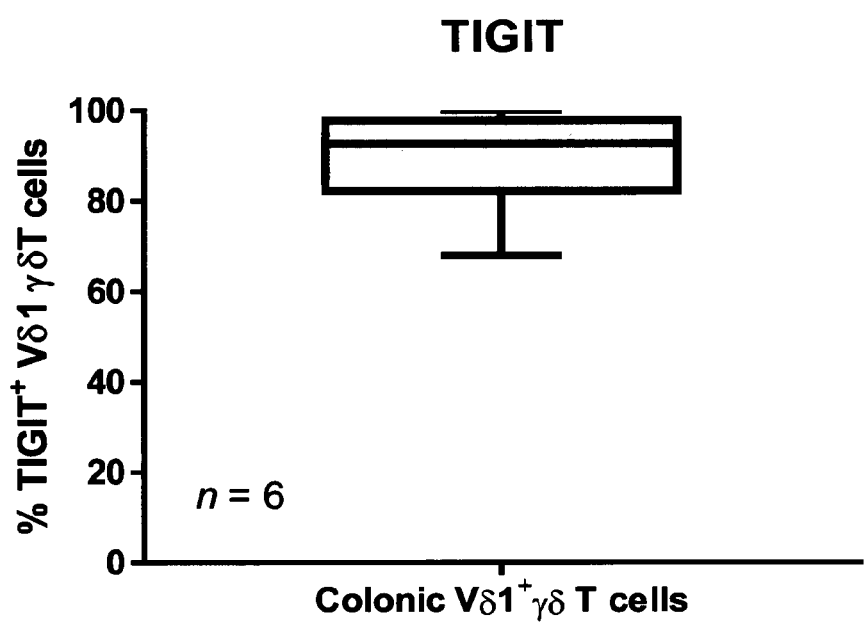
FIG. 23 is a graph showing constitutive TIGIT expression on gut resident Vδ1 cells. The data was generated using Vδ1 cells isolated from gut epithelium using a standard isolation protocol for the release of colonic intra-epithelial lymphocytes.

TIGIT was constitutively expressed on gut resident Vδ1 cells, as shown in FIG. 23. Data was generated using Vδ1 cells isolated from gut by conventional tissue digestion. Constitutive TIGIT expression of tissue resident γδ T cell is not only related to skin-derived Vδ1 cells, and TIGIT expression was not an artifact of the Clark protocol (grid-based isolation procedure).

Figure 24A:
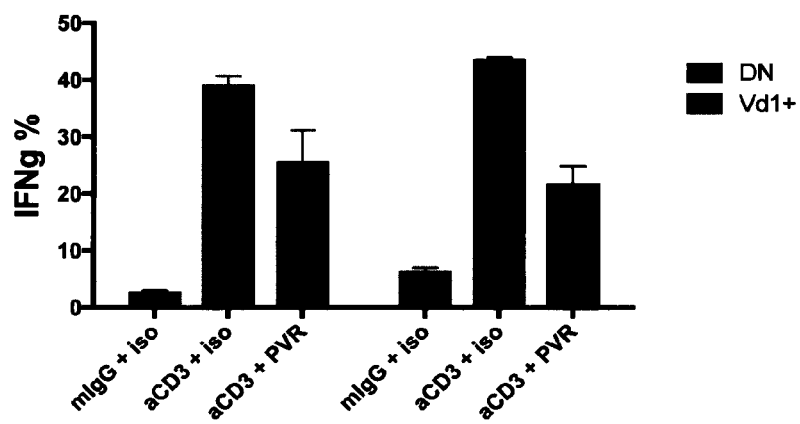
FIGS. 24A and 24B are graphs graph showing that Poliovirus receptor (PVR) specifically inhibits TCR signaling as measured by IFNγ (FIG. 24A) and TNFα (FIG. 24B) expression. Cells were incubated with IL-2 and IL-15 and activated with anti-CD3 antibody.
Figure 24B:
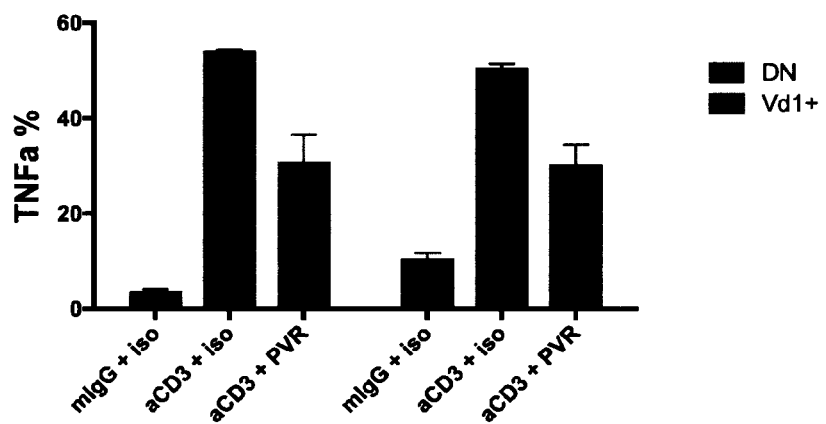
Figure 25A:
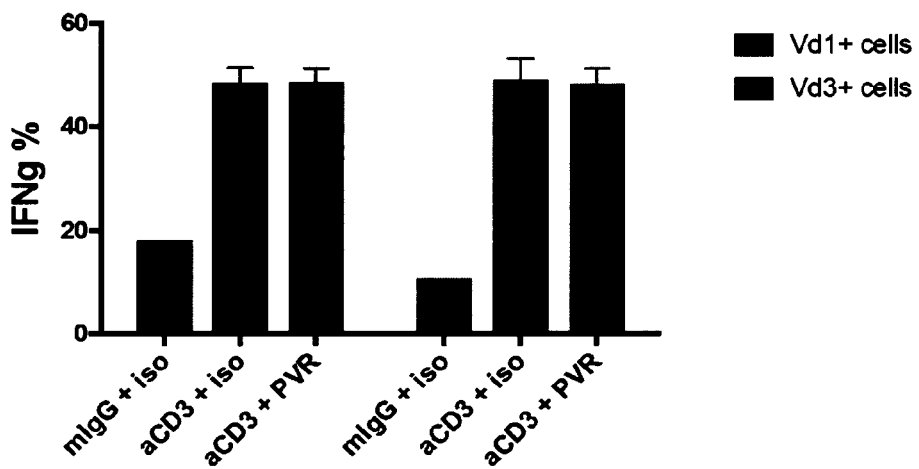
FIGS. 25A and 25B are graphs showing that the PVR inhibitory effect is lost on TIGIT-negative Vδ1+/Vδ3+ cells as measured by IFNγ (FIG. 25A) or TNFα (FIG. 25B). The cells were incubated with IL-2, IL-15, IL-4, and IL-21 and activated with anti-CD3 antibody.
Figure 25B:
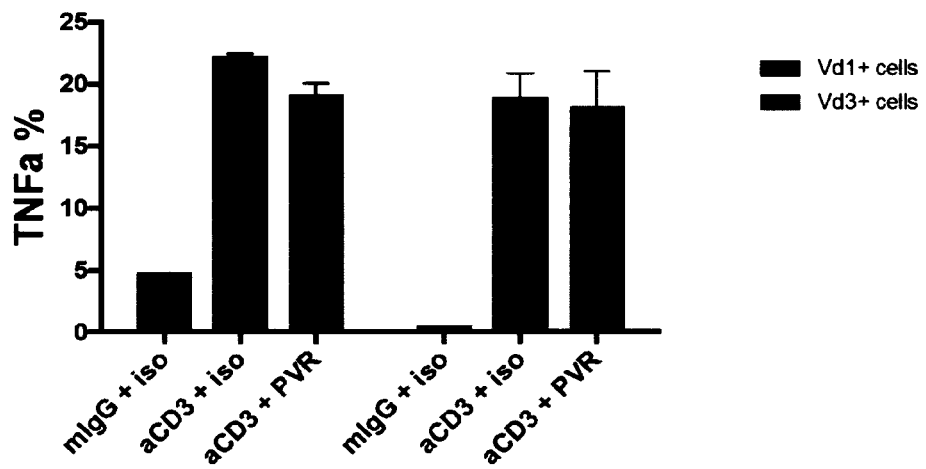

Furthermore, in cells incubated with IL-2 and IL-15 only, Poliovirus receptor (PVR) specifically inhibited TCR signaling, as measured by IFNγ expression (FIG. 24A) and TNFα (FIG. 24B). In cells incubated with IL-2, IL-15, IL-4, and IL-21, the PVR inhibitory effect was lost on TIGIT-negative Vδ1+/Vδ3+, cells as measured by IFNγ (FIG. 25A) or TNFα (FIG. 25B), indicating that TIGIT-negativity resulting from the four cytokine mix preferentially prevents inhibition of TIGIT-mediated activation of Vδ1+/Vδ3+ T cells.

Example 7. IL-9 Substitution for IL-2 in Expansion Cultures

Figure 26A:
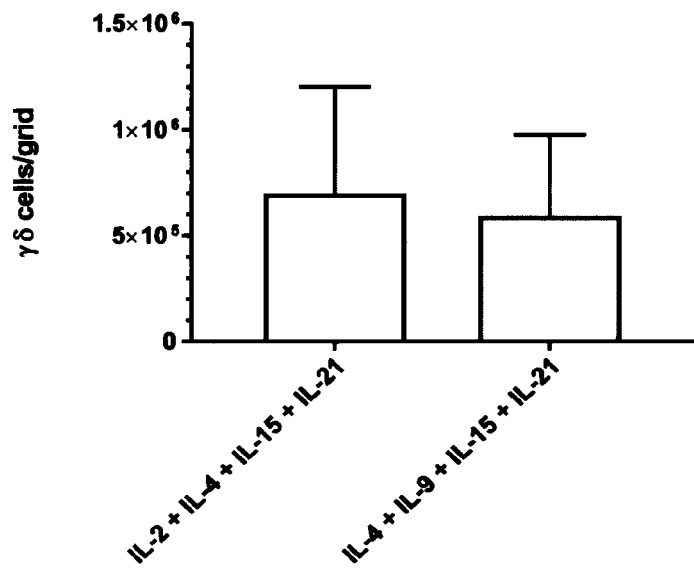
FIGS. 26A and 26B are graphs showing that IL-9 can replace the function of IL-2 in expansion of skin-derived γδ T cells. Skin tissues from three donors (TS052, TS056, and SK073) were placed on 9 mm grids and cultured for three weeks in medium supplemented with IL-2 and IL-15. Next, isolated lymphocytes were expanded in medium supplemented with either IL-2, IL-4-IL-15, and IL-21 (left bars) or IL-4, IL-9, IL-15 and IL-21 (right bars). The final yield of γδ T cells/grid (FIG. 26A) and Vδ1 cells/grid (FIG. 26B) were calculated after 3 weeks of expansion. Replacing IL-2 with IL-9 in expansion of skin-derived γδ T cells resulted in equivalent expansion efficiency. The histograms represent mean+/−SEM.
Figure 26B:
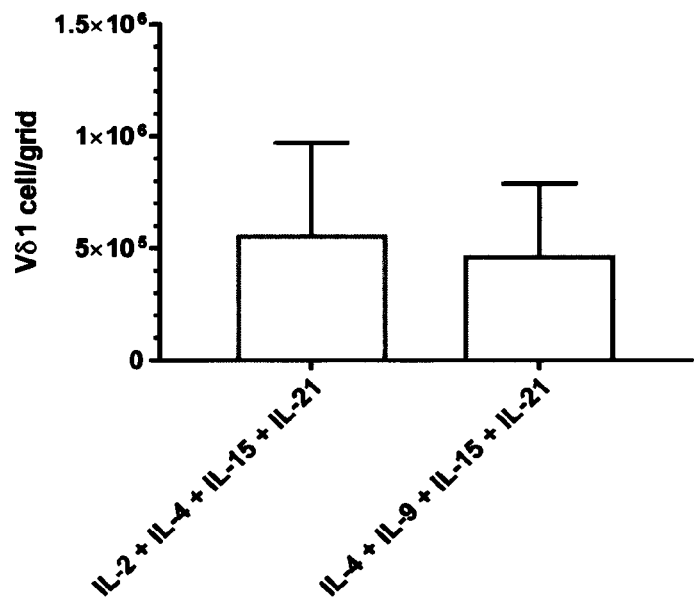

Skin tissues from three donors (TS052, TS056, and SK073) were placed on 9 mm grids and cultured for three weeks in medium supplemented with IL-2 and IL-15. Isolated lymphocytes were incubated in media supplemented with IL-2, IL-4-IL-15, and IL-21 (FIGS. 26A and 26B left bars) or IL-4, IL-9, IL-15 and IL-21 (FIGS. 26A and 26B right bars). The final yield of γδ T cells/grid (FIG. 26A) and Vδ1 cells/grid (FIG. 26B) were calculated after three weeks of expansion.

Figure 27A:
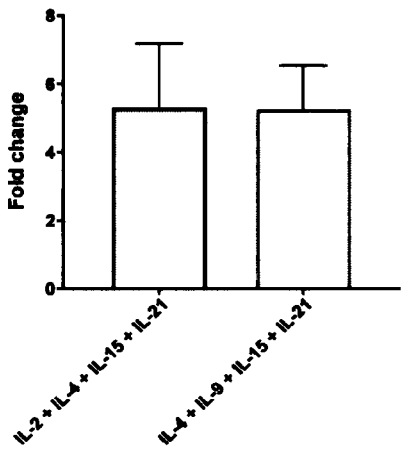
FIGS. 27A-27C are graphs showing that IL-9 can replace the function of IL-2 in expansion of skin-derived γδ T cells as measured by fold change (FIG. 27A), % of γδTCR+ T cells (FIG. 27B), and % of Vδ1+ T cells (FIG. 27C). Skin tissues were from six donors (SK073, SK075, SK077, TS052, TS053, and TS056). 2CK=2 cytokines (IL-2+IL-15) and 4CK=4 cytokines (IL-2+IL-15+IL-21+IL-4).
Figure 27B:
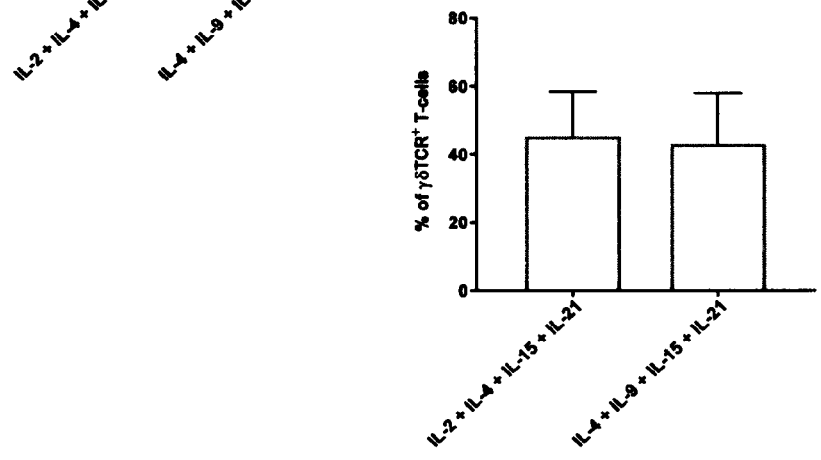
Figure 27C:
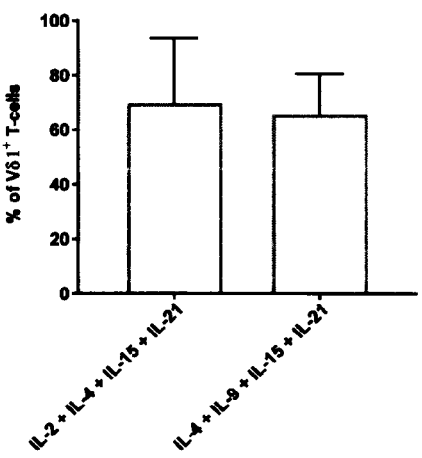

As shown in FIGS. 27A-27C, IL-9 was sufficient to replace the function of IL-2 in expansion of skin γδ T cells as measured by fold change (FIG. 27A), % of γδTCR+ T cells (FIG. 27B), and % of Vδ1+ T cells (FIG. 27C). Skin tissues were from six donors (SK073, SK075, SK077, TS052, TS053, and TS056). The two-cytokine cocktail included IL-2 and IL-15, and the four-cytokine cocktail included IL-2, IL-15, IL-21, and IL-4.

As shown in FIGS. 28A and 28B, IL-9 was sufficient to replace the function of IL-2 in expansion of skin γδ T cells as measured by mean fluorescence intensity (MFI) of CD27 expression on Vδ1+ T cells (FIG. 28A) and normalized MFI of CD27 expression on Vδ1+ T cells (FIG. 28B). No difference in CD27 expression compared to standard culture conditions was observed. Skin tissues were from four donors (SK073, TS052, TS053, and TS056). The two-cytokine cocktail consisted of IL-2 and IL-15, and the four-cytokine cocktail consisted of IL-2, IL-15, IL-21, and IL-4.

Expansion of Skin-Derived γδ T Cells

Mixed lymphocytes were harvested after three weeks of scaffold culture, washed in phosphate-buffered saline (PBS), spun down, and re-suspended in RPMI-1640 with filtered 10% heat-inactivated FBS (Life Technologies), L-glutamine (292 µg/ml; Life Technologies), penicillin (100 units/ml; Life Technologies), streptomycin (100 µg/ml; Life Technologies), N-2-hydroxyethylpiperazine-N-2-ethane sulfonic acid (HEPES; 0.01 M; Life Technologies), sodium pyruvate (1 mM; Life Technologies), minimal essential media (MEM) non-essential amino acids (1×; Life Technologies) and 50 mM 2-mercaptoethanol (Life Technologies) at a concentration of $1 \times 10^6$ cells/ml. Cells were seeded at $2 \times 10^6$ cells/well into 24-well plates (Corning) for expansion with medium supplemented with cytokines as indicated at the following final concentrations: IL-2: 100 U/mL, IL-4: 5 ng/mL, IL-9: 10 ng/mL, IL-15: 20 ng/mL, and IL-21: 10 ng/mL.

Cells were monitored daily by microscopy and provided with fresh media and cytokines three times per week by replacing 1 mL culture medium with 1 mL fresh culture medium containing cytokines at double strength, i.e., IL-2: 200 U/mL, IL-4: 10 ng/mL, IL-9: 20 ng/mL, IL-15: 40 ng/mL, and IL-21: 20 ng/mL.

Upon full confluence and cell aggregation, cells were split 1:1 into additional wells and plates, as required. After 21 days, cells were harvested using ACCUTASE® (eBioscience), counted, and analyzed using flow cytometry. Final γδ T cell and Vδ1 cell numbers were calculated using pre- and post-expansion numbers and the data shows final cell yield per grid after expansion.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of expanding γδ T cells, the method comprising the steps of:
   (i) providing a population of γδ T cells obtained from a non-haematopoietic tissue; and
   (ii) culturing the γδ T cells in the presence of:
       (a) IL-2 or IL-9;
       (b) IL-15; and
       (c) IL-21
   for at least 5 days in amounts effective to produce an expanded population of γδ T cells,
   wherein the method further comprises, after step (i), separating the γδ T cells from non-haematopoietic cells to produce a separated population of γδ T cells, and step (ii) comprises culturing the γδ T cells in the absence of substantial stromal cell contact; and
   wherein step (ii) comprises culturing the γδ T cells in the absence of exogenous TCR pathway agonists.

2. The method of claim 1, wherein step (ii) further comprises culturing the γδ T cells in the presence of IL-4.

3. The method of claim 1 wherein step (ii) further comprises:
   culturing the γδ T cells in the presence of IL-2, IL-15, and a factor selected from the group consisting of IL-21, stromal cell-derived factor (SDF), IL-1β, IL-12, IL-18, and IL-33 for at least 5 days to produce an expanded population of γδ T cells.

4. The method of claim 1, wherein step (ii) comprises culturing the γδ T cells in serum-free medium.

5. The method of claim 1, wherein the method further comprises, after step (i), separating the γδ T cells from non-haematopoietic cells to produce a separated population of γδ T cells, and step (ii) comprises:
   (a) culturing the γδ T cells in the absence of substantial tumor cell contact; and/or
   (b) culturing the γδ T cells in the absence of substantial feeder cell contact.

6. The method of claim 5, wherein the step of separating the γδ T cells from non-haematopoietic cells comprises culturing the γδ T cells and the non-haematopoietic cells on a synthetic scaffold configured to facilitate cell egress from the non-haematopoietic tissue.

7. The method of claim 5, wherein the step of separating the γδ T cells from non-haematopoietic cells comprises culturing the γδ T cells and the non-haematopoietic cells in the presence of IL-2 and/or IL-15.

8. The method of claim 5 wherein a separated population of lymphocytes comprises the separated population of γδ T cells, and the separated population of γδ T cells comprises a separated population of Vδ1 T cells.

9. The method of claim 5, wherein at least 80% of the separated population of γδ T cells are Vδ1 T cells prior to expansion.

10. The method of claim 5, wherein αβ T cells and/or NK cells are removed from the separated population of γδ T cells.

11. The method of claim 1, wherein within 14 days of culture, the expanded population of γδ T cells comprises at least 20-fold the number of γδ T cells relative to the separated population of γδ T cells prior to expansion.

12. The method of claim 1, wherein within 21 days of culture, the expanded population of γδ T cells comprises at least 50-fold the number of γδ T cells relative to the separated population of γδ T cells prior to expansion.

13. The method of claim 1, wherein the expanded population of γδ T cells comprises an expanded population of Vδ1 T cells.

14. The method of claim 13, wherein within 14 days of culture, the expanded population of Vδ1 T cells comprises at least 20-fold the number of Vδ1 T cells relative to the separated population of Vδ1 T cells prior to expansion.

15. The method of claim 13, wherein within 21 days of culture, the expanded population of Vδ1 T cells comprises at least 50-fold the number of Vδ1 T cells relative to the separated population of Vδ1 T cells prior to expansion.

16. The method of claim 14, wherein within 21 days of culture, the expanded population of Vδ1 T cells comprises at least 50-fold the number of Vδ1 T cells relative to the separated population of Vδ1 T cells prior to expansion.

17. The method of claim 1, wherein the non-haematopoietic tissue is skin.

* * * * *